US010810736B2

(12) United States Patent
Fuchs et al.

(10) Patent No.: US 10,810,736 B2
(45) Date of Patent: *Oct. 20, 2020

(54) SYSTEMS AND METHODS FOR MULTIPLE INSTANCE LEARNING FOR CLASSIFICATION AND LOCALIZATION IN BIOMEDICAL IMAGING

(71) Applicant: MEMORIAL SLOAN KETTERING CANCER CENTER, New York, NY (US)

(72) Inventors: Thomas Fuchs, New York, NY (US); Gabriele Campanella, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/599,992

(22) Filed: Oct. 11, 2019

(65) Prior Publication Data

US 2020/0043164 A1 Feb. 6, 2020

Related U.S. Application Data

(63) Continuation of application No. 16/362,470, filed on Mar. 22, 2019, now Pat. No. 10,445,879.

(Continued)

(51) Int. Cl.
*G06T 7/00* (2017.01)
*G06K 9/62* (2006.01)
(Continued)

(52) U.S. Cl.
CPC ............. *G06T 7/0012* (2013.01); *G06K 9/03* (2013.01); *G06K 9/623* (2013.01); *G06K 9/628* (2013.01);
(Continued)

(58) Field of Classification Search
CPC ......... G06T 7/0012; G06T 2207/20084; G06T 2207/20076; G06T 2207/20081;
(Continued)

(56) References Cited

U.S. PATENT DOCUMENTS 10,007,982 B2 * 6/2018 Heine .................... G06K 9/527
10,037,601 B1 * 7/2018 Ben-Ari ............... G06K 9/4604
(Continued)

OTHER PUBLICATIONS

Courtiol et al., "Classification and disease localization in histopathology using only global labels: a weakly-supervised approach," Cornell University/Computer Science/Computer Vision and Pattern Recognition (Feb. 1, 2018).
(Continued)

*Primary Examiner* — Bobbak Safaipour
(74) *Attorney, Agent, or Firm* — Foley & Lardner LLP

(57) ABSTRACT

The present disclosure is directed to systems and methods for classifying biomedical images. A feature classifier may generate a plurality of tiles from a biomedical image. Each tile may correspond to a portion of the biomedical image. The feature classifier may select a subset of tiles from the plurality of tiles by applying an inference model. The subset of tiles may have highest scores. Each score may indicate a likelihood that the corresponding tile includes a feature indicative of the presence of the condition. The feature classifier may determine a classification result for the biomedical image by applying an aggregation model. The classification result may indicate whether the biomedical includes the presence or lack of the condition.

20 Claims, 51 Drawing Sheets

Related U.S. Application Data

(60) Provisional application No. 62/647,002, filed on Mar. 23, 2018, provisional application No. 62/670,432, filed on May 11, 2018.

(51) Int. Cl.
| | |
|---|---|
| *G06K 9/03* | (2006.01) |
| *G16H 30/40* | (2018.01) |
| *G16H 50/70* | (2018.01) |
| *G06N 20/00* | (2019.01) |

(52) U.S. Cl.
CPC ......... *G06K 9/6262* (2013.01); *G06K 9/6277* (2013.01); *G06N 20/00* (2019.01); *G16H 30/40* (2018.01); *G16H 50/70* (2018.01); *G06K 2209/05* (2013.01); *G06T 2207/10056* (2013.01); *G06T 2207/20076* (2013.01); *G06T 2207/20081* (2013.01); *G06T 2207/20084* (2013.01); *G06T 2207/30096* (2013.01)

(58) Field of Classification Search
CPC .......... G06T 2207/10056; G06T 2207/30096; G06K 9/6277; G06K 9/623; G06K 9/628; G06K 9/03; G06K 9/6262; G06K 2209/05; G06N 20/00; G16H 50/70; G16H 30/40
See application file for complete search history.

(56) References Cited

U.S. PATENT DOCUMENTS

| | | | |
|---|---|---|---|
| 2014/0233826 A1 | 8/2014 | Agaian et al. | |
| 2016/0098589 A1* | 4/2016 | Brieu | G06K 9/4652 |
| | | | 382/128 |
| 2016/0110863 A1* | 4/2016 | Heine | G06K 9/0051 |
| | | | 382/132 |
| 2016/0335478 A1* | 11/2016 | Bredno | A61B 17/3423 |
| 2017/0161891 A1 | 6/2017 | Madabhushi et al. | |
| 2018/0253589 A1* | 9/2018 | Wu | G06T 7/0012 |
| 2018/0374210 A1* | 12/2018 | Barker | G06T 7/0012 |
| 2019/0073569 A1* | 3/2019 | Ben-Ari | G16H 50/20 |

OTHER PUBLICATIONS

Guan et al., "Diagnose like a radiologist: attention guided convolutional neural network for thorax disease classification," Cornell University/Computer Science/Computer Vision and Pattern Recognition (Jan. 30, 2018).

International Search Report and Written Opinion, PCT/US2019/023748, Memorial Sloan Kettering Cancer Center, dated Jun. 11, 2019, 10 pages.

* cited by examiner

|  | FPR | FNR | Error |
|---|---|---|---|
| 5x | 11.3 | 21.1 | 16.3 |
| 10x | 8.1 | 16.5 | 12.4 |
| 20x | 14.5 | 9.3 | 12.0 |
| max(5,10,20) | 26.1 | 5.1 | 15.3 |
| avg(5,10,20) | 6.8 | 13.5 | 10.2 |
| max(5,20) | 23.4 | 5.5 | 14.2 |
| avg(5,20) | 11.3 | 11.4 | 11.3 |

FIG. 9

SYSTEMS AND METHODS FOR MULTIPLE INSTANCE LEARNING FOR CLASSIFICATION AND LOCALIZATION IN BIOMEDICAL IMAGING

CROSS-REFERENCES TO RELATED APPLICATIONS

The present application claims the benefit of priority under 35 U.S.C. § 120 as a continuation of U.S. patent application Ser. No. 16/362,470, titled "SYSTEMS AND METHODS FOR MULTIPLE INSTANCE LEARNING FOR CLASSIFICATION AND LOCALIZATION IN BIOMEDICAL IMAGING," filed on Mar. 22, 2019, which claims the benefit of priority under 35 U.S.C. § 119(e) to U.S. Provisional Patent Application No. 62/647,002, titled "TERABYTE-SCALE DEEP MULTIPLE INSTANCE LEARNING FOR CLASSIFICATION AND LOCALIZATION IN PATHOLOGY," filed Mar. 23, 2018, and to U.S. Provisional Patent Application No. 62/670,432, titled "TERABYTE-SCALE DEEP MULTIPLE INSTANCE LEARNING FOR CLASSIFICATION AND LOCALIZATION IN PATHOLOGY," filed May 11, 2018, each of which are incorporated in their entireties.

BACKGROUND

Computer vision algorithms may be used to recognize and detect various features on digital images. Detection of features on a biomedical image may consume a significant amount of computing resources and time, due to the potentially enormous resolution and size of biomedical images.

SUMMARY

At least one aspect is directed to a method of training models for classifying biomedical images. An image classifier executing on one or more processors may generate a plurality of tiles from each biomedical image of a plurality of biomedical images. The plurality of biomedical images may include a first biomedical image and a second biomedical image. The first biomedical image may have a first label indicating a presence of a first condition and the second biomedical image may have a second label indicating a lack of presence of the first condition or a presence of a second condition. The image classifier may establish an inference system to determine, for each tile of the plurality of tiles in each biomedical image of the plurality of biomedical images, a score indicating a likelihood that the tile includes a feature indicative of the presence of the first condition. For the first biomedical image, the image classifier may select a first subset of tiles from the plurality of tiles having the highest scores. The image classifier may compare the scores of the tiles in the first subset to a first threshold value corresponding to the presence of the first condition. The image classifier may modify the inference system responsive to determining that the scores of at least one tile of the first subset of tiles is below the first threshold value. For the second biomedical image, the image classifier may select a second subset of tiles from the plurality of tiles having the highest scores. The image classifier may compare the scores of the tiles in the second subset to a second threshold value corresponding to the lack of the presence of the first condition or the presence of the second condition. The image classifier may modify the inference system responsive to determining that the scores of at least one tile of the second subset of tiles is above the second threshold value.

In some embodiments, the image classifier may determine, for the at least one tile of the first subset, a first error metric between the score of the at least one tile to a first value corresponding to the presence of the first condition. In some embodiments, modifying the inference system may include modifying the inference system based on the first error metric of the at least one tile of the first subset. In some embodiments, the image classifier may determine, for the at least one tile of the second subset, a second error metric between the score of the at least one tile to a second value corresponding to the lack of the presence of the first condition. In some embodiments, modifying the inference system may include modifying the inference system based on the second error metric of the at least one tile of the second subset.

In some embodiments, the image classifier may maintain the inference system responsive to determining that scores of none of a plurality of tiles for a third biomedical image of the plurality of biomedical images is below the first threshold. The third biomedical image may have the first label indicating the presence of the first condition. In some embodiments, the image classifier may maintain the inference system responsive to determining that scores of none of a plurality of tiles for a fourth biomedical image of the plurality of biomedical images is below the second threshold. The fourth biomedical image may have the first label indicating the lack of the presence of the first condition.

In some embodiments, selecting the first subset of tiles may include selecting a predefined first number of tiles from the plurality of tiles for the first biomedical image having the highest scores. In some embodiments, selecting the second subset of tiles may include selecting a predefined second number of tiles from the plurality of tiles for the second biomedical image having the highest scores.

In some embodiments, establishing the inference system may include initializing the inference system comprising a convolutional neural network. The convolutional neural network may have one or more parameters. Each parameter of the one or more parameters may be set to a random value. In some embodiments, the image classifier may apply a third subset of tiles from a plurality of tiles for a third biomedical image of the plurality of biomedical images to an aggregation system to train the aggregation system based on a comparison on a label of the third biomedical image with a classification result from applying the aggregation system to third subset.

At least one aspect is directed to a method of training models for classifying biomedical images. An image classifier executing on one or more processors may identify a subset of tiles from a plurality of tiles of a biomedical image of a plurality of biomedical images, the biomedical image having a label indicating a presence of a condition. The image classifier may establish an aggregation system to determine classifications of biomedical images to indicate whether the corresponding biomedical image contains a feature indicative of the presence of the condition. The image classifier may determine a classification result for the biomedical image by applying the aggregation system to the subset of tiles identified from the biomedical image. The classification result may indicate one of the biomedical image as containing at least one feature corresponding to the presence of the condition or the biomedical image as lacking any features corresponding to the lack the of the condition. The image classifier may compare the classification result determined for the biomedical image with the label indicating the presence of the condition on the biomedical image. The image classifier may modify the aggregation system responsive to determining that the classification result from the aggregation system does not match the label for the biomedical image.

In some embodiments, the image classifier may determine an error metric between the classification result and the label, responsive to determining that the classification result does not match the label for the biomedical image. In some embodiments, modifying the aggregation system may include modifying at least one parameter of the aggregation system based on the error metric.

In some embodiments, establishing the aggregation system may include initializing the aggregation system comprising a recurrent neural network. The recurrent neural network may have one or more parameters. Each parameter of the one or more parameters may be set to a random value. In some embodiments, the image classifier may maintain the aggregation system responsive to determining that a second classification result from the aggregation system for a second subset of tiles from a second biomedical image matches a second label for the second biomedical image.

In some embodiments, applying the aggregation system to the subset of tiles may include applying the subset of tiles in one of a sequential order or random order from the plurality of tiles for the biomedical image. In some embodiments, identifying the subset of tiles may include identifying the subset of tiles from the plurality of tiles for the biomedical image selected by an inference system based on scores. Each score for a corresponding tile of the subset may indicate a likelihood that the corresponding tile includes a feature indicative of the presence of the condition.

At least one aspect is directed to a system for classifying biomedical images. The system may include a plurality of biomedical images maintainable on a database. The system may include an inference system maintainable on one or more processors. The inference system may select subsets of tiles from the plurality of biomedical images including features indicative of a presence of a first condition. The system may include an aggregation system maintainable on the one or more processors. The aggregation system may determine whether biomedical images are classified as one of including the presence of the first condition or a lack of the first condition or a presence of a second condition. The system may include a feature classifier executable on the one or more processors. The feature classifier may generate a plurality of tiles from at least one biomedical image of the plurality of biomedical images. Each tile may correspond to a portion of the biomedical image. The feature classifier may select a subset of tiles from the plurality of tiles for the biomedical image by applying the inference system to the plurality of tiles. The subset of tiles may have highest scores. Each score may indicate a likelihood that the corresponding tile includes a feature indicative of the presence of the first condition. The feature classifier may determine a classification result for the biomedical image by applying the aggregation system to the selected subset of tiles. The classification result may indicate whether the biomedical includes the presence of the first condition or the lack of the first condition or the presence of the second condition.

In some embodiments, the feature classifier may generate the plurality of tiles by using one of a plurality of defined magnification factors onto the biomedical image. In some embodiments, the feature classifier may determine, for each tile of the plurality of tiles of the biomedical image, by applying the inference system to the tile, a score indicating the likelihood that the tile includes features indicative of the presence of the first condition. In some embodiments, the feature classifier may select a predefined number of tiles from the plurality of tiles having the highest scores to form the subset of tiles. In some embodiments, the feature classifier may input the selected subset of tiles in sequential order or in random order in to the aggregation system to determine the classification result for the biomedical image.

In some embodiments, the system may include a model trainer executable on the one or more processors. The model trainer may generate a plurality of tiles from each biomedical image of the plurality of biomedical images. The plurality of biomedical images may include a first biomedical image having a first label indicating the presence of the first condition and a second biomedical image having a second label indicating a lack of the presence of the first condition or the presence of the second condition. The model trainer may select a first subset of tiles from the plurality of tiles of the first biomedical image having the highest scores among the plurality of tiles from the first biomedical image. The model trainer may select a second subset of tiles from the plurality of tiles of the second biomedical image having the highest scores among the plurality of tiles from the second biomedical image. The model trainer may modify the inference system based on a first comparison between the scores of the first subset of tiles and a first value corresponding to the presence of the first condition and a second comparison between the scores of the second subset of tiles and a second value corresponding to the lack of the presence of the first condition or the presence of the second condition.

In some embodiments, the system may include a model trainer executable on the one or more processors. The model trainer may determine a first error metric based on the first comparison between the scores of the first subset of tiles and a first value corresponding to the presence of the first condition. The model trainer may determine a second error metric based on the second comparison between the scores of the second subset of tiles and a second value corresponding to the lack of the presence of the first condition or the presence of the second condition. The model trainer may modify at least one parameter of the inference system based on the first error metric and the second error metric.

In some embodiments, the system may include a model trainer executable on the one or more processors. The model trainer may identify a subset of tiles from the plurality of tiles of a second biomedical image of the plurality of biomedical images, the second biomedical image having a label indicating the presence of a first condition. The model trainer may determine a second classification result for the second biomedical image by applying the aggregation system to the subset of tiles identified from the second biomedical image. The classification result may indicate one of the second biomedical image as containing at least one feature corresponding to the presence of the first condition or the second biomedical image as lacking any features corresponding to the lack the presence of the first condition or the presence of the second condition. The model trainer may modify the aggregation system based on a comparison between the second classification result and the label for the second biomedical image.

In some embodiments, the system may include a model trainer executable on the one or more processors. The model trainer may determine, subsequent to modifying the inference system, that one or more parameters of the inference system have converged relative the one or more parameters prior to the modification of the inference system. The model trainer may initiate training of the aggregation mode, responsive to the determination that the one or more parameters of the inference has converged.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 9 depicts a table listing a performance comparison between models;

DETAILED DESCRIPTION

Figure 1:
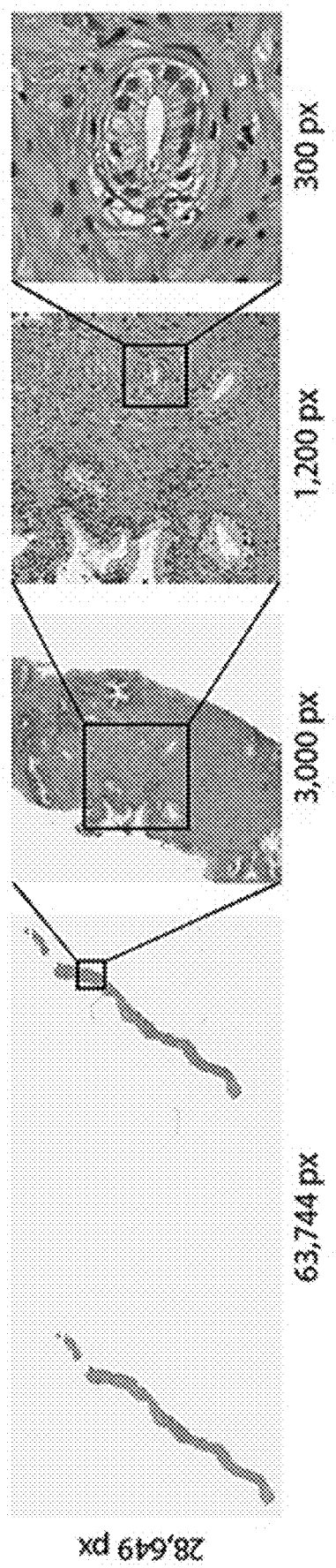
FIG. 1 depicts an example of a whole slide image (WSI) at various magnification factors.

Following below are more detailed descriptions of various concepts related to, and embodiments of, inventive systems and methods for processing immobilization molds. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes Terabyte-Scale Deep Multiple Instance Learning for Classification and Localization in Pathology.

Section B describes systems and methods of using two-dimensional slicing in training an encoder-decoder model for reconstructing biomedical images and applying the encoder-decoder model to reconstruct biomedical images.

Section C describes systems and methods of classifying biomedical images and training models for classifying biomedical images using multiple-instance learning.

Section D describes a network environment and computing environment which may be useful for practicing various computing related embodiments described herein.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Terabyte-Scale Deep Multiple Instance Learning for Classification and Localization in Pathology 1. Introduction For some years there has been a strong push towards the digitization of pathology. The increasing size of available digital pathology data, coupled with the impressive advances that the fields of computer vision and machine learning have made in recent years, make for the perfect combination to deploy decision support systems in the clinic.

Despite few success stories, translating the achievements of computer vision to the medical domain is still far from solved. The lack of large datasets which are indispensable to learn high capacity classification models has set back the advance of computational pathology. The "CAMELYON16" challenge for metastasis detection contains one of the largest labeled datasets in the field with a total of 400 Whole Slide Images (WSIs). Such an amount of cases is extremely small compared to the millions of instances present in the ImageNet dataset. One widely adopted solution to face the scarcity of labeled examples in pathology is to take advantage of the size of each example. Pathology slides scanned at 20× magnification produce image files of several Gigapixels. About 470 WSIs contain roughly the same number of pixels as the entire ImageNet dataset. By breaking the WSIs into small tiles it is possible to obtain thousands of instances per slide, enough to learn high-capacity models from a few hundred slides. Pixel-level annotations for supervised learning are prohibitively expensive and time consuming, especially in pathology. Some efforts along these lines have achieved state-of-the-art results on CAMELYON16. Despite the success on these carefully crafted datasets, the performance of these models hardly transfers to the real life scenario in the clinic because of the huge variance in real-world samples that is not captured by these small datasets.

2. Summary

In summary, until now it was not possible to train high-capacity models at scale due to the lack of large WSI datasets. A dataset of unprecedented size in the field of computational pathology has been gathered. The data set includes over 12,000 slides from prostate needle biopsies, two orders of magnitude larger than most datasets in the field and with roughly the same number of pixels of 25 ImageNet datasets. Whole slide prostate cancer classification was chosen as a representative one in computational pathology due to its medical relevance and its computational difficulty. Prostate cancer is expected to be the leading source of new cancer cases for men and the second most frequent cause of death behind only the cancers of the lung and multiple studies have shown that prostate cancer diagnosis has a high inter- and intra-observer variability. It is important to note that the classification is frequently based on the presence of very small lesions that can comprise just a fraction of 1% of the tissue surface. Referring now to FIG. 1, depicted are whole slide images (WSI) at various magnification factors. Prostate cancer diagnosis is a difficult task. The diagnosis can be based on very small lesions. In the slide above, only about 6 small tumor glands are present. The right most image shows an example tumor gland. Its relation to the entire slide is put in evidence to reiterate the complexity of the task. The figure depicts the difficulty of the task, where only a few tumor glands concentrated in a small region of the slide determine the diagnosis.

Since the introduction of the Multiple Instance Learning (MIL) framework in 1997 there have been many efforts from both the theory and application of MIL in the computer vision literature. It has been determined that the MIL framework is very applicable to the case of WSI diagnosis and despite its success with classic computer vision algorithms, MIL has never been applied in computational pathology due, in part, to the lack of large WSI datasets. In the present disclosure, advantage is taken of a large prostate needle biopsy dataset. The present disclosure relates to a Deep Multiple Instance Learning (MIL) framework where only the whole slide class is needed to train a convolutional neural network capable of classifying digital slides on a large scale.

It is the first time pathology digital slide classification is formalized as a weakly supervised learning task under the MIL framework. Few other studies have applied MIL to the medical domain, but none in pathology. For instance, in comparison to pathology, CT slides and mammograms are much smaller and usually each image is used directly in a fully supervised approach. In previous studies applying MIL, MIL is used to enhance the classification accuracy and provide localization of the most characteristic regions in each image.

Diagnosis prediction of Whole Slide Images (WSI) can be seen as a weakly supervised task where the location of the disease within a positive slide is unknown. In this study the Multiple Instance Learning (MIL) paradigm is used to tackle the weakly supervised task of diagnosis prediction. In MTh, each WSI is a collection of small tiles. Each tile has a certain probability of being of class positive. Only if all tiles in a WSI are negative, the probability of being positive is lower than 0.5, the WSI is negative. According to MIL, learning can be achieved from the top-1 most positive tile in each WSI via a simple cross-entropy loss function and gradient descent optimization.

3. Dataset

A dataset including 12,160 needle biopsies slides scanned at 20× magnification, of which 2,424 are positive and 9,736 are negative is used. The diagnosis was retrieved from the original pathology reports in the Laboratory Information System (LIS) of a medical institution. Exploratory experiments were run on a subset of the full dataset including 1,759 slides split among a training set of 1,300 slides and a validation set of 459 slides. Both splits had a balanced number of positive and negative cases. The large-scale experiments were run on the entire dataset on a 70%-15%-15% random split for training, validation and testing respectively. During training, tiles are augmented on the fly with random horizontal flips and 90° rotations.

Figure 2:
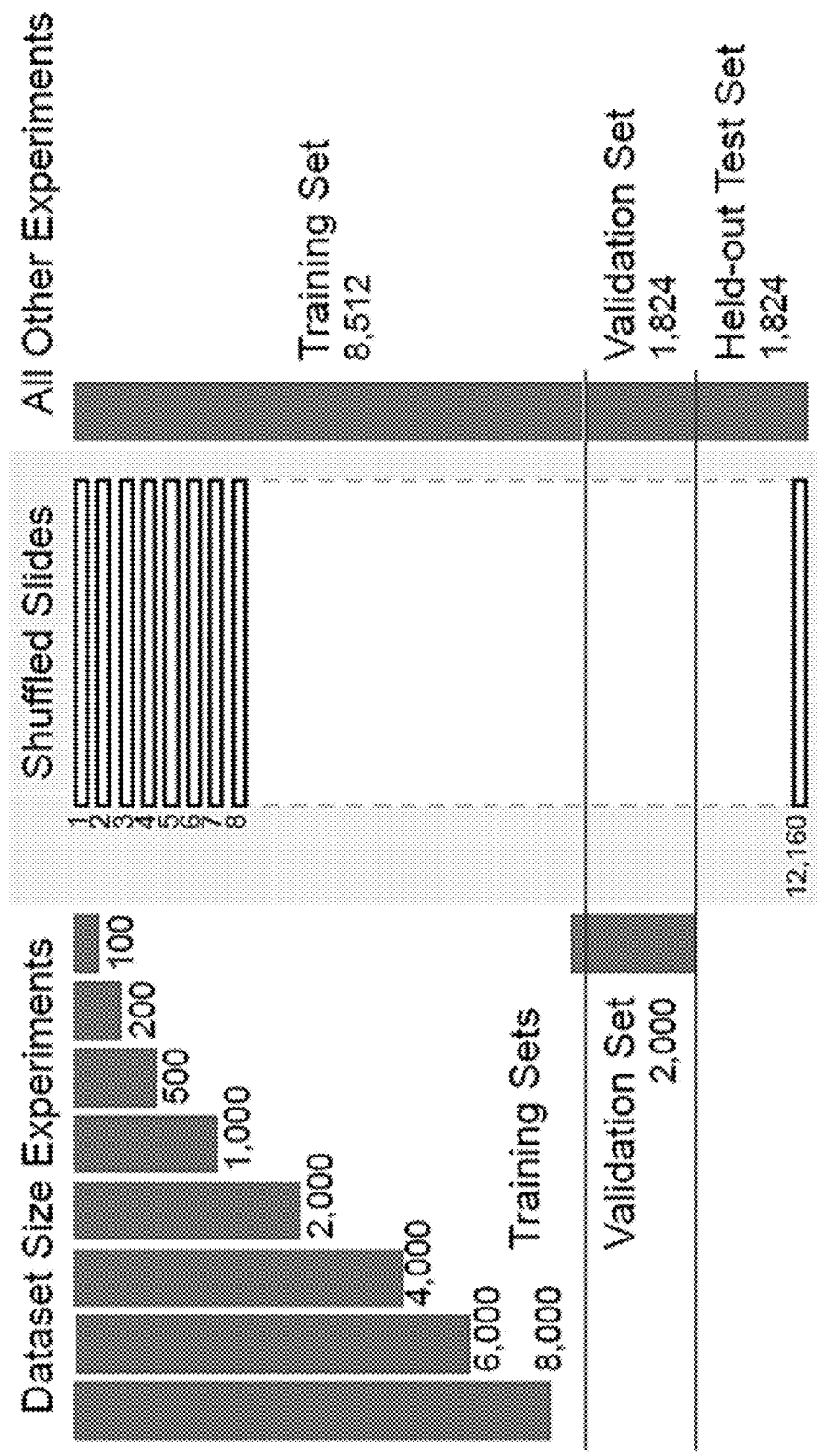
FIG. 2 depicts a bar graph of splitting of a biopsy dataset.

Referring now to FIG. 2, depicted are bar graphs of splitting of a biopsy dataset. The full dataset was divided into 70-15-15% splits for training, validation, and test for all experiments except the ones investigating dataset size importance. For those, out of the 85% training/validation split of the full dataset, training sets of increasing size were generated along with a common validation set. As visualized, the dataset was randomly split in training (70%), validation (15%) and testing (15%). No augmentation was performed during training. For the "dataset size importance" experiments, explained further in the Experiments section, a set of slides from the above mentioned training set were drawn to create training sets of different sizes.

4. Methods

Classification of a whole digital slide based on a tile-level classifier can be formalized under the classic MIL paradigm when only the slide-level class is known and the classes of each tile in the slide are unknown. Each slide $s_i$ from the slide pool $S = \{s_i: i=1, 2, \ldots, n\}$ can be considered as a bag consisting of a multitude of instances (tiles). For positive bags, it must exist at least one instance that is classified as positive by some classifier. For negative bags instead, all instances must be classified as negative. Given a bag, all instances are exhaustively classified and ranked according to their probability of being positive. If the bag is positive, the top-ranked instance should have a probability of being positive that approaches one, while if it is negative, the probability should approach zero. The complete pipeline of the method comprises the following steps: (i) tiling of each slide in the dataset; for each epoch, which consists of an entire pass through the training data, (ii) a complete inference pass through all the data; (iii) intra-slide ranking of instances; (iv) model learning based on the top-1 ranked instance for each slide.

Figure 3:
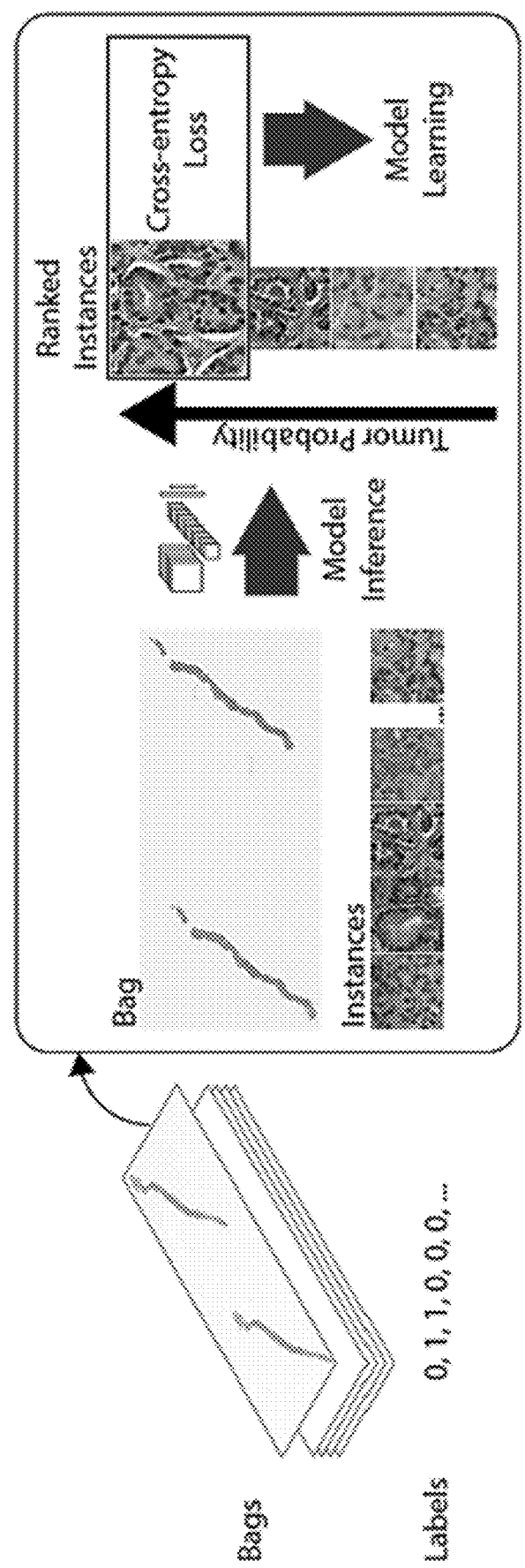
FIG. 3 depicts a schema of performing multiple instance learning for classification of tumorous features on whole slide images.

Referring to FIG. 3, depicted is a schema of performing multiple instance learning for classification of tumorous features on whole slide images. The slide or bag consists of multiple instances. Given the current model, all the instances in the bag are used for inference. They are then ranked according to the probability of being of class positive (tumor probability). The top ranked instance is used for model learning via the standard cross-entropy loss. Unless otherwise noted a gradient step is taken every 100 randomly sampled slides and the models used in experiments is an AlexNet and VGG11 pretrained on ImageNet allowing all layers to be optimized.

Slide Tiling: The instances are generated by tiling the slide on a grid. All the background tiles are efficiently discarded by an algorithm, reducing drastically the amount of computation per slide, since quite a big portion of it is not covered by tissue. Furthermore, tiling can be performed at different magnification levels and with various levels of overlap between adjacent tiles. In this work three magnification levels (5×, 10× and 20×) were investigated, with no overlap for 10× and 20× magnification and with 50% overlap for 5× magnification. On average each slide contains about 100 non overlapping tissue tiles at 5× magnification and 1,000 at 20× magnification. More detailed information on the composition of the bags is given in FIGS. 6A-C. Given a tiling strategy and sampled slide $s_i$, bags B={$B_{s_i}$: i=1, 2, ..., n} where $B_{s_i}$={$b_{i,1}$, $b_{i,2}$, ..., $b_{i,m}$} is the bag for slide $s_i$ containing m total tiles. An example of tiling can be seen in FIG. 5.

Model Training: The model is a function $f_\theta$ with current parameters $\theta$ that maps input tiles $b_{i,j}$ to class probabilities for "negative" and "positive" classes. Given bags B a list of vectors O={$\overline{o_i}$: i=1, 2, ..., n} was obtained, one for each slide $s_i$ containing the probabilities of class "positive" for each tile $b_{i,j}$: j=1, 2, ..., m in $B_{s_i}$. The index $k_i$ of the tile was obtained within each slide which shows the highest probability of being "positive" $k_i$=argmax($\overline{o_i}$). The highest ranking tile in bag $B_{s_i}$ is then $b_{i,k}$. The output of the network $\tilde{y}_i$=$f_\theta(b_{i,k})$ can be compared to $y_i$, the target of slide $s_i$, thorough the cross-entropy loss 1 as in Equation 1.

$$l=-w_1[y_i \log(\tilde{y}_i)]-w_0[(1-y_i) \log(1\tilde{y}_i)] \quad (1)$$

Given the unbalanced frequency of classes, weights w0 and w1, for negative and positive classes respectively, can be used to give more importance to the underrepresented examples. The final loss is the weighted average of the losses over a mini-batch. Minimization of the loss is achieved via stochastic gradient descent using the Adam optimizer and learning rate 0.0001. Mini-batches of size 512 for AlexNet, 256 for ResNets and 128 for VGGs were used.

Model Testing: At test time all the instances of each slide are fed through the network. Given a threshold (usually 0.5), if at least one instance is positive then the entire slide is called positive; if all the instances are negative then the slide is negative. Accuracy, confusion matrix and ROC curve are calculated to analyze performance.

5. Exploratory Experiments

Experiments in were performed on a HPC cluster. In particular, seven NVIDIA DGX-1 workstations each containing 8 V100 Volta GPUs were used. OpenSlide was used to access on-the-fly the WSI files and PyTorch for data loading, building models, and training. Further data manipulation of results was performed in R.

Figure 4:
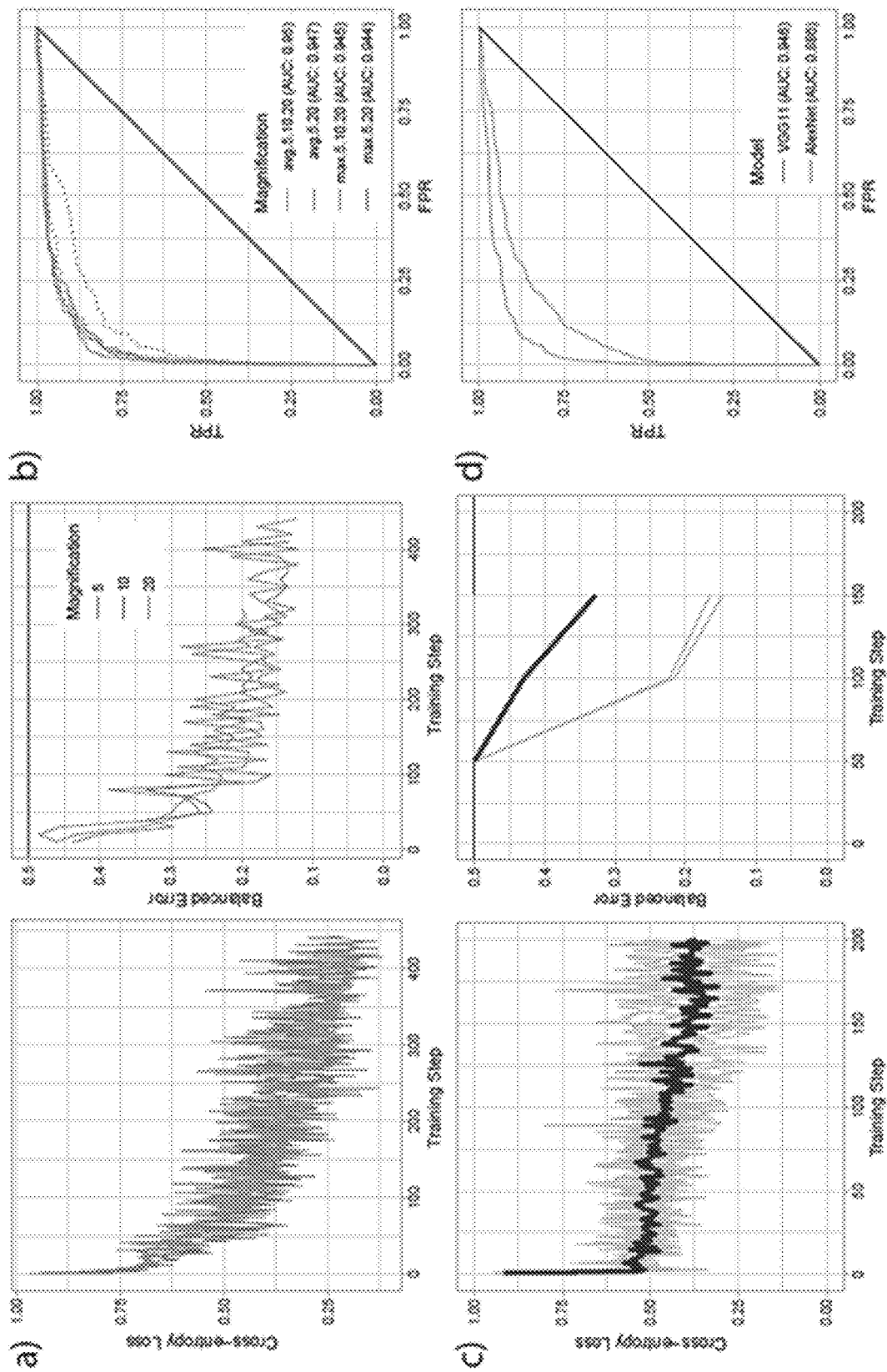
FIG. 4 depicts line graphs indicating losses and validation errors.

Classic MIL: Various standard image classification models pre-trained on Imagenet under the MIL setup at 20× magnification and no overlap were tested. Each experiment was run 100 steps 5 times with different random initializations of the classification layers. Referring to FIG. 4, depicted are Training loss and validation error (a) and best model performance with the naive multi-scale approach (b) on the exploratory dataset. The colored ROC curves are different multi-scale modalities, which are compared to the single magnification models (dotted lines). c) Training and validation balanced error for the large-scale experiment with VGG11. d) Test set ROC curve of the best VGG11 model trained on large-scale. It was observed that not all the architectures are able to lower the loss under this optimization scheme. In particular, AlexNet was able to reduce the loss 4/5 of the time, while VGG11, which has an architecture very similar to AlexNet but contains 11 convolutional layers instead of 5, run successfully 2/5 of the time. Interestingly, adding batch normalization to VGG11 completely erases the performance seen in the standard VGG11. Finally, ResNet18 similarly to VGG11BN also gets stuck on a suboptimal minimum. Different optimizers and learning rates were also tested with similar results.

AlexNet gave the best and most reliable results and its performance was further tested under different magnifications. The MIL setup requires an exhaustive pass through every slide and thus it is quite time consuming. The experiments shown next were run for 160 hours and then stopped. FIG. 4(a) shows the training loss for the AlexNet model trained at different magnifications; to note how after 400 steps convergence has not been reached yet. FIG. 4(b) shows the overall misclassification error, the false negative rate and false positive rate for the validation set. As expected, the model originally assigns a positive label to every slide. As training proceeds, the false positive rate decreases while the false negative rate tends to increase. The best performing models on the validation set achieved 83.7, 87.6 and 88.0% accuracy for 5×, 10× and 20× magnification respectively as seen in FIG. 4(a). 20× magnification seem to produce overall more false positives, while 5× s produces more false negatives. Finally, the models achieve 0.943, 0.935 and 0.895 AUC for 5×, 10× and 20× magnification respectively in the ROC curves in FIG. 4(d). There seems to be quite a drop in performance at 5× magnification, but this may be due to the 10-fold decrease in number of patches present at 5× with respect to 20× magnification.

Error Analysis: Detailed analysis of the true positive cases (Referring to FIGS. 8A(a) and (b)) substantiates the hypothesis that irrespective of magnification, the attention is focused on malignant glands but based on different features which indicates that a multi-scale approach could be beneficial. Investigation of the 43 false positive slides (FIG. 8B) reveal known mimickers of prostate cancer like atrophy, adenosis and inflammation as well as seminal vesicles and colorectal tissue. The 29 false negative slides (FIG. 8C) were cases with very little tumor surface with predominant errors at 5×. Arguably, more training data containing more examples of mimickers would be useful to push the false positive rate down which reemphasizes the usefulness of real-world studies over curated toy datasets.

Naive multi-scale MIL. Previous results showed that many errors were not shared among the models learned at different magnifications. In addition, 5× and 20× magnifications showed complementary performance with respect to error modes. This suggests that a possible boost in performance may be possible by integrating information at different magnifications. The easiest approach is to combine the responses of the models trained at different magnifications. Here the probability of positive class of the models was combined from the previous section in four ways: (i) max(5, 10, 20), (ii) max(5, 20), (iii) average(5, 10, 20), (iv) average (5, 20). Taking the maximum probability tends to increase the false positive rate, while drastically reducing the false negative rate. Whereas taking the average response leads to an overall lower error rate. The results shown in Table 1 and in the ROC curves in FIGS. 4(b) and 10A demonstrate the improved performance of the multi-scale approach.

Other MIL Extensions. Further experiments were performed to analyze the effect of tiling the slides with 50% overlap. The results showed only a minor improvement over the basic non overlapping approach. Given the encouraging results of the naive multi-scale approach, learning a multi-scale model was also tried with three different architectures. The experiments didn't show improved performance over previous results.

6. Large-Scale MIL

Figure 13:
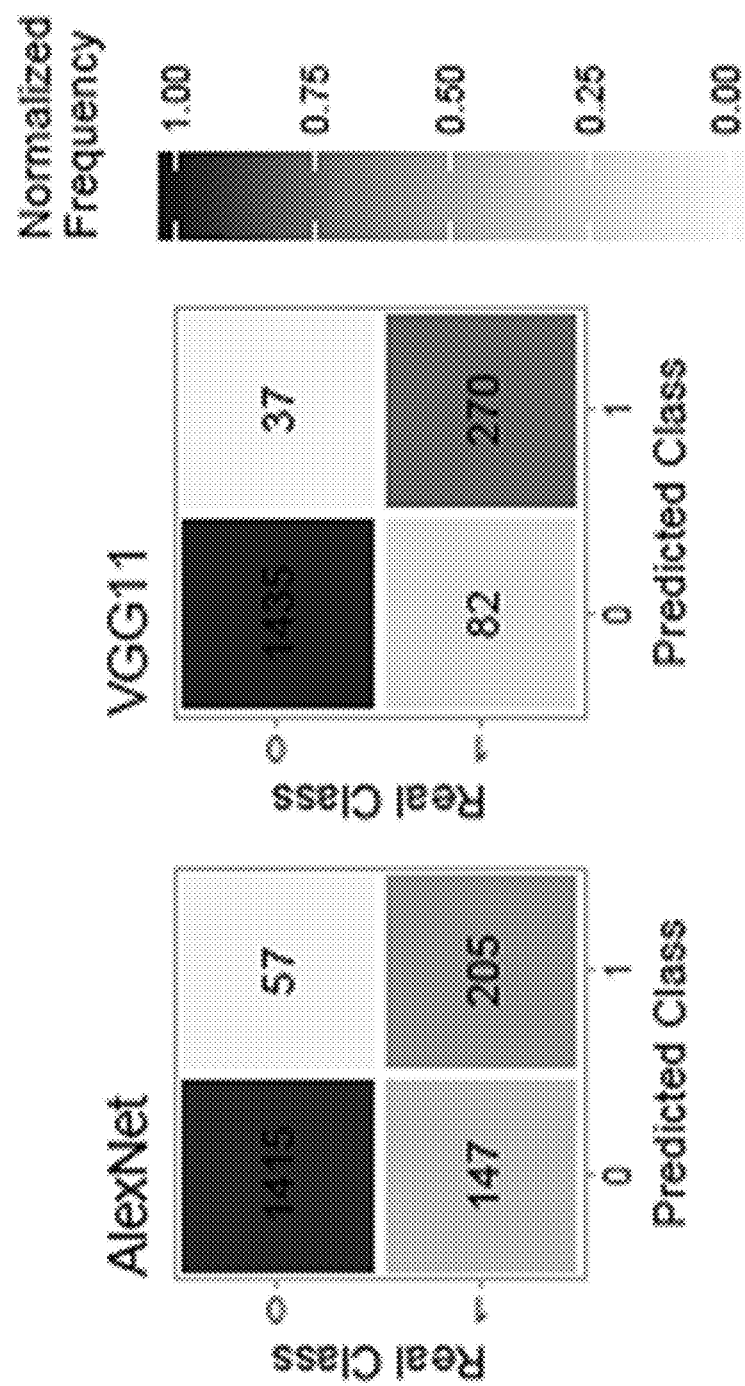
FIG. 13 depicts confusion matrices for models on test sets.
Figure 19:
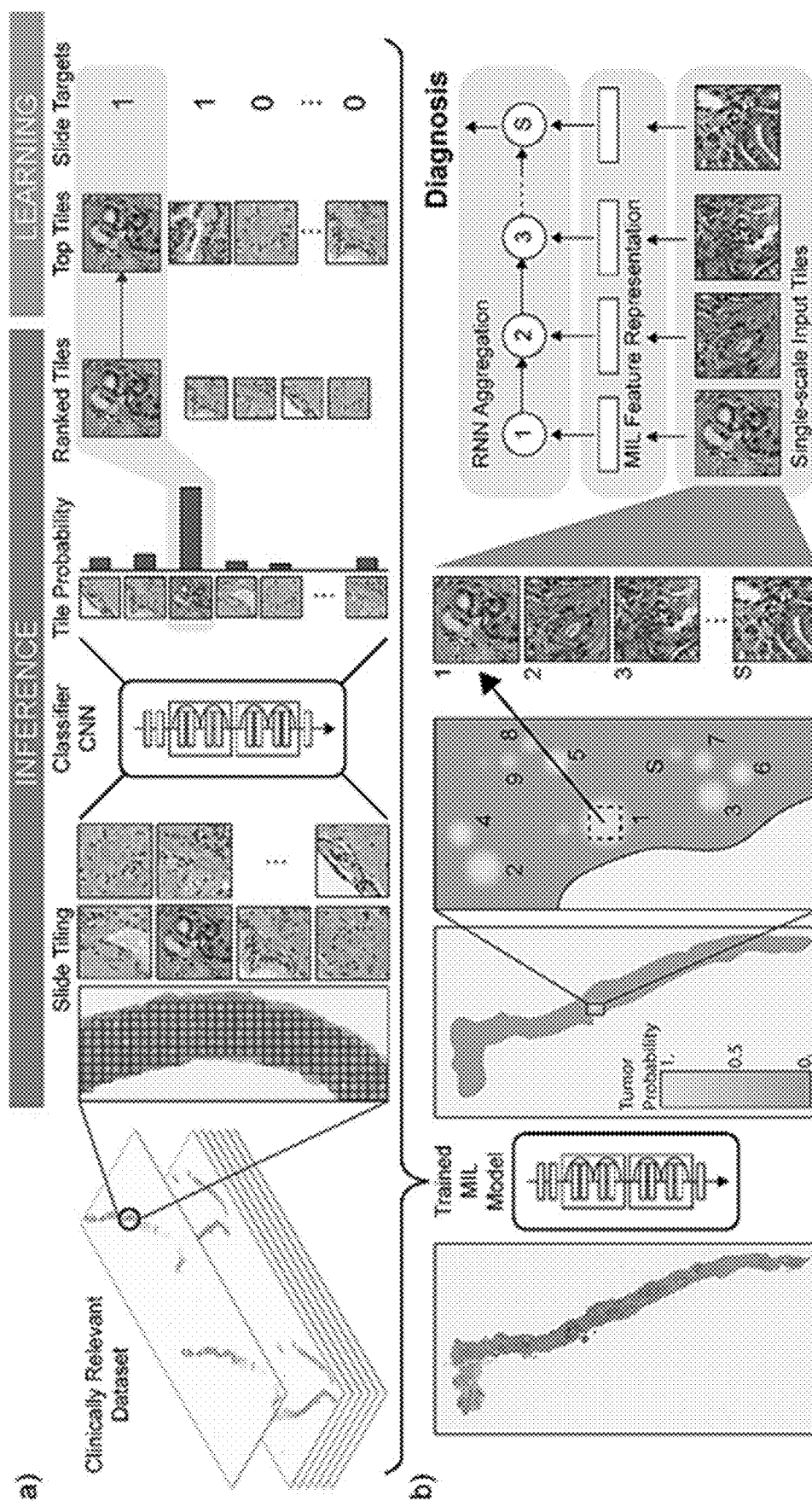
FIG. 19 depicts a block diagram of schema of an architecture for multiple instance learning.

AlexNet and a VGG11 models pretrained on ImageNet on the full dataset were trained: 8,512 slides for training and 1,824 for validation. Each experiment was run 4 times to inspect the robustness to random initializations and optimization. Given the computational cost of fully inspecting every 20× tile in such a large dataset, the training was tested on the validation set only every 50 steps. The jobs were stopped after 160 hours completing almost 200 steps training steps. Traces of the training procedure are shown in FIG. 4(c) and 13 (depicting confusion matrices for the best AlexNet and VGG11 models on the test set). Both AlexNet and VGG11 were able, at least in a subset of the runs, to reduce the loss during training. It is also clear that the models were still learning and that with more training the error could have decreased more. The best models, for each architecture, after 150 runs were selected to be tested on the test dataset consisting of 1,824 slides never used before, confusion matrices are shown in FIG. 19. VGG11 achieved the best performance on the test set with a balanced error rate of 13% and an AUC of 0.946 as seen in FIG. 4(d).

Weight Tuning

Figure 24:
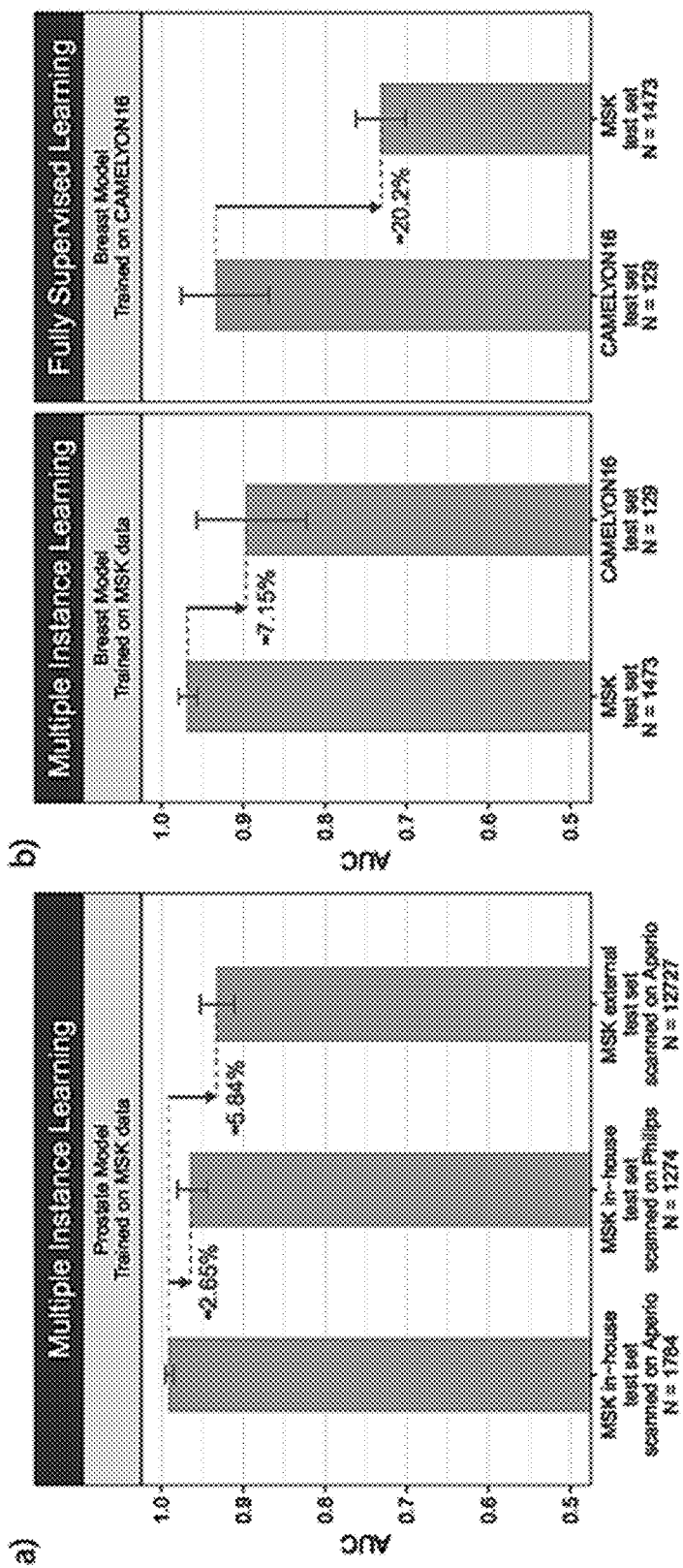
FIG. 24 depicts bar graphs juxtaposing the performance of different models.

Needle biopsy diagnosis is an unbalanced classification task. The full dataset consists of 19.9% positive examples and 80.1% negative ones. To determine whether weighting the classification loss is beneficial, training was performed on the full dataset an AlexNet and a Resnet18 networks, both pretrained on ImageNet, with weights for the positive class $w_1$ equal to 0.5, 0.7, 0.9, 0.95 and 0.99. The weights for both classes sum to 1, where $w_1=0.5$ means that both classes are equally weighted. Each experiment was run five times and the best validation balanced error for each run was gathered. Training curves and validation balanced errors are reported in FIG. 24. Weights 0.9 and 0.95 were determined to give the best results. For the reminder of the experiments $w_1=0.9$ was used.

Dataset Size Importance

Figure 14:
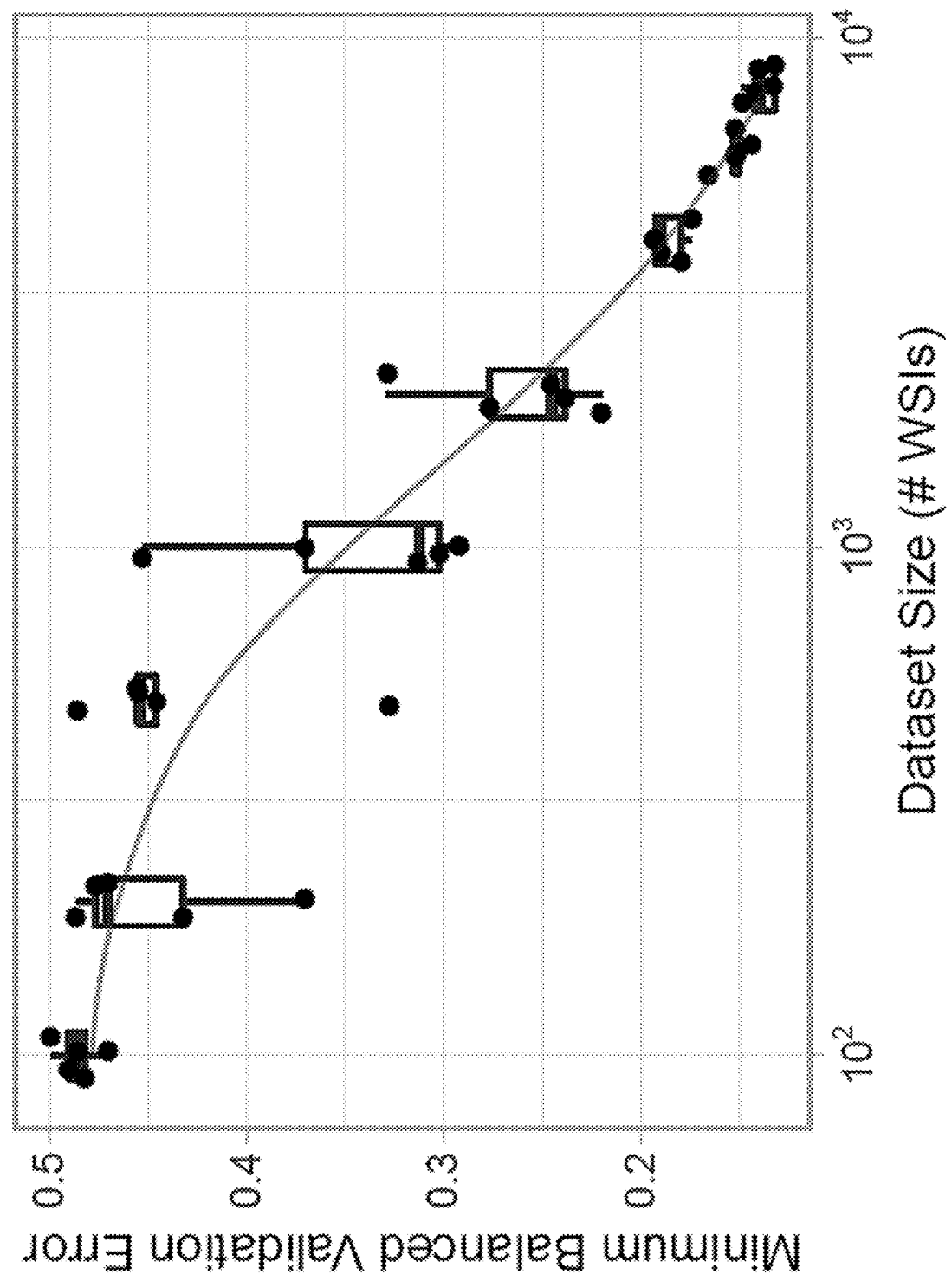
FIG. 14 depicts line graphs of dataset size for classification performance
Figure 15:
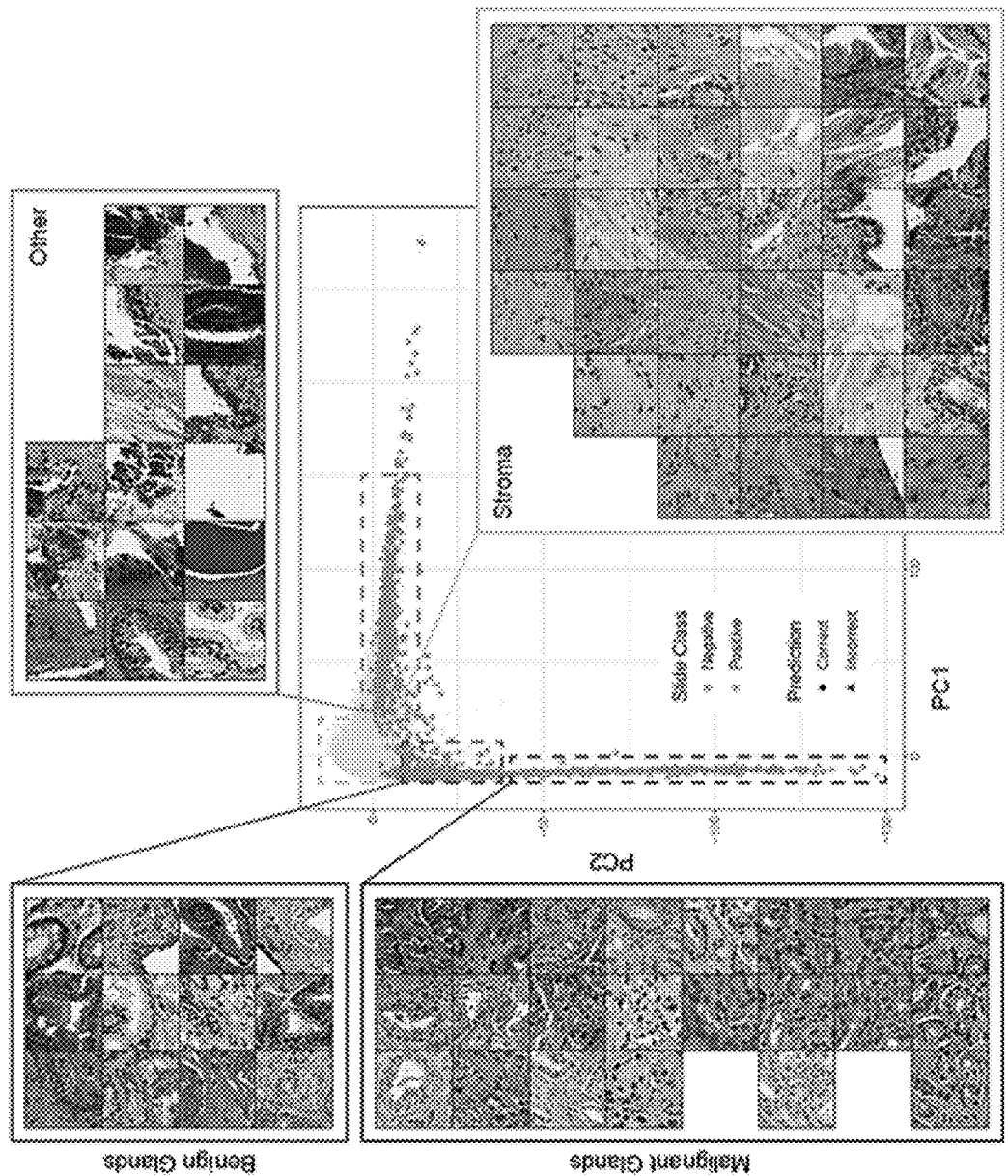
FIG. 15 depicts a visualization of feature space with principle component analysis (PCA) in scatter plot.

In the following set of experiments, how dataset size affects performance of a MIL based slide diagnosis task were determined. For these experiments the full dataset was split in a common validation set with 2,000 slides and training sets of different sizes: 100, 200, 500, 1,000, 2,000, 4,000, 6,000. Each bigger training dataset fully contained all previous datasets. For each condition, an AlexNet was trained five times and the best balanced errors on the common validation set are shown in FIG. 14 demonstrating how a MIL based classifier could not have been trained until now due to the lack of a large WSI dataset. Training curves and validation errors are also reported in FIG. 17B.

Model Comparison

Various standard image classification models pretrained on ImageNet (AlexNet, VGG11-BN, ResNet18, Resnet34) under the MIL setup at 20× magnification were tested. Each experiment was run for up to 60 epochs for at least five times with different random initializations of the classification layers. In terms of balanced error on the validation set, AlexNet performed the worst, followed by the 18-layer ResNet and the 34-layer ResNet. Interestingly, the VGG11 network achieved results similar to those of the ResNet34 on this task. Training and validation results are reported in FIG. 17D.

Figure 16:
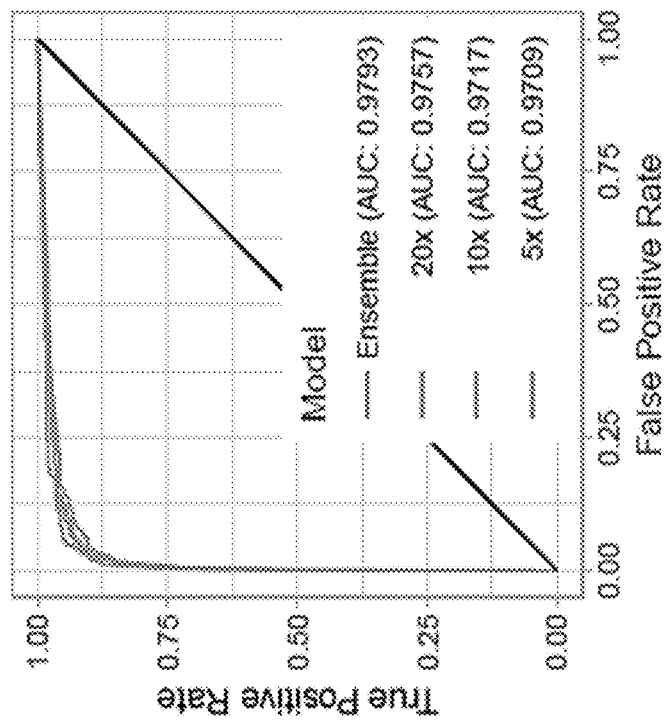
FIG. 16 depicts line graphs of receiver operating characteristics (ROC) of different models.
Figure 16:
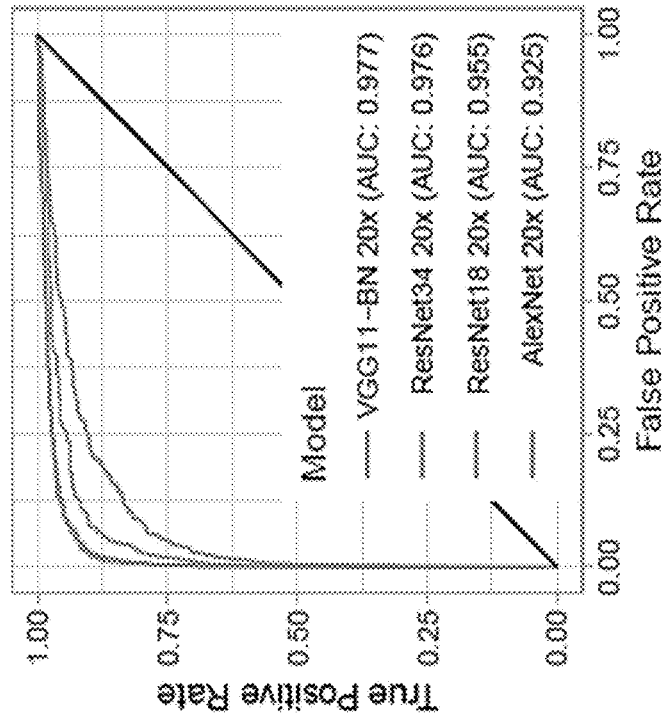

Test Dataset Performance: For each architecture, the best model on the validation dataset was chosen for final testing. Performance was similar with the one on the validation data indicating good generalization. The best models were Resnet34 and VGG11-BN which achieved 0.976 and 0.977 AUC respectively. The ROC curves are shown in FIG. 16(a).

Error Analysis: A thorough analysis of the error modalities of the VGG11-BN model was performed by a pathologist. Of the 1,824 test slides, 55 were false positives (3.7% false positive rate) and 33 were false negatives (9.4% false negative rate). The analysis of the false positives found seven cases that were considered highly suspicious for prostate cancer. Six cases were considered "atypical", meaning that following-up with staining would have been necessary. Of the remaining false positives, 18 were a mix of known mimickers of prostate cancer: adenosis, atrophy, benign prostatic hyperplasia, and inflammation. The false negative cases were carefully inspected, but in six cases no sign of prostate cancer was found by the pathologist. The rest of the false negative cases were characterized by very low volume of cancer tissue.

Figure 17A:
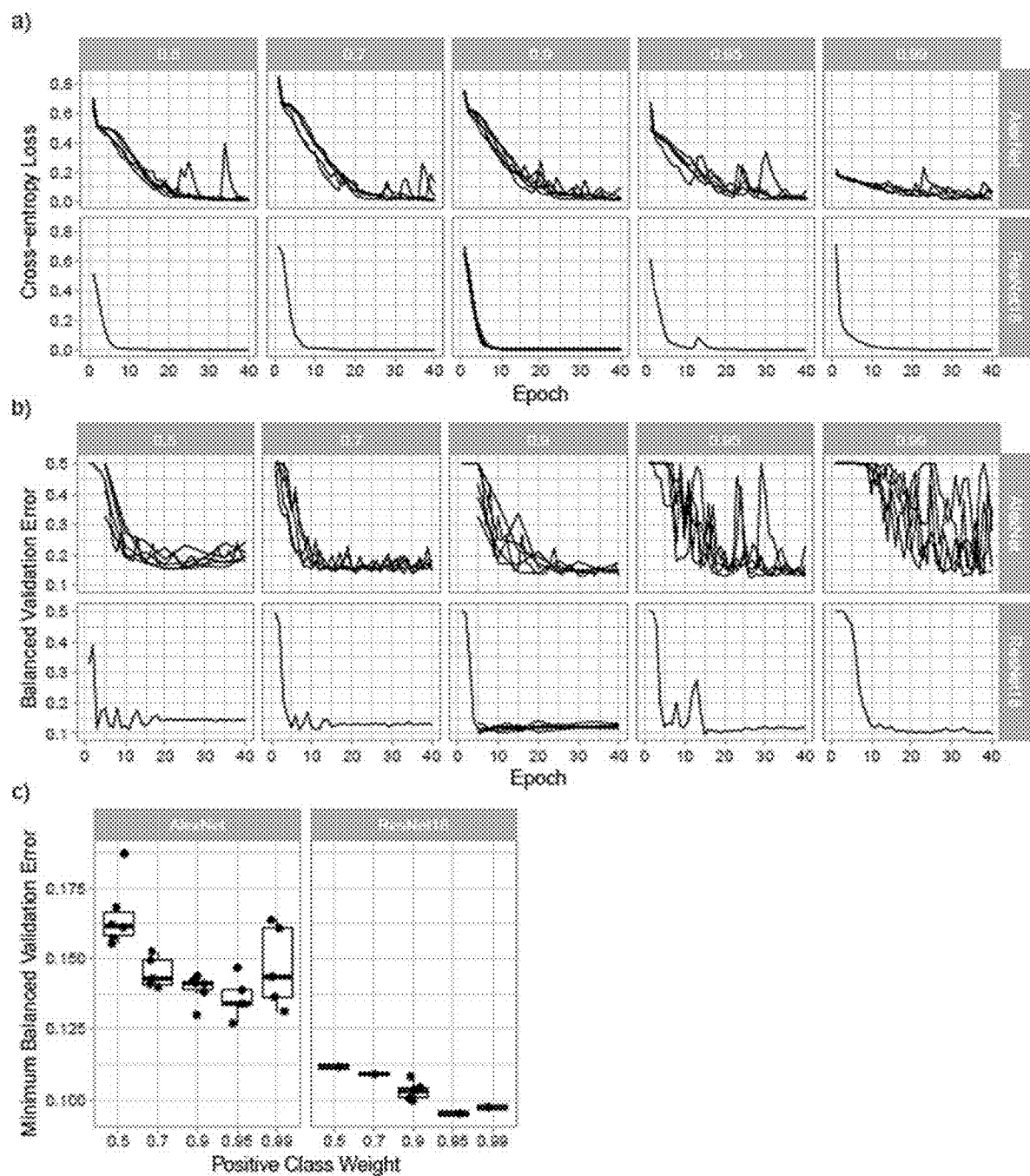
FIGS. 17A-E each depicts line graphs of comparisons of different models at various magnification factors on the whole slide images.
Figure 17B:
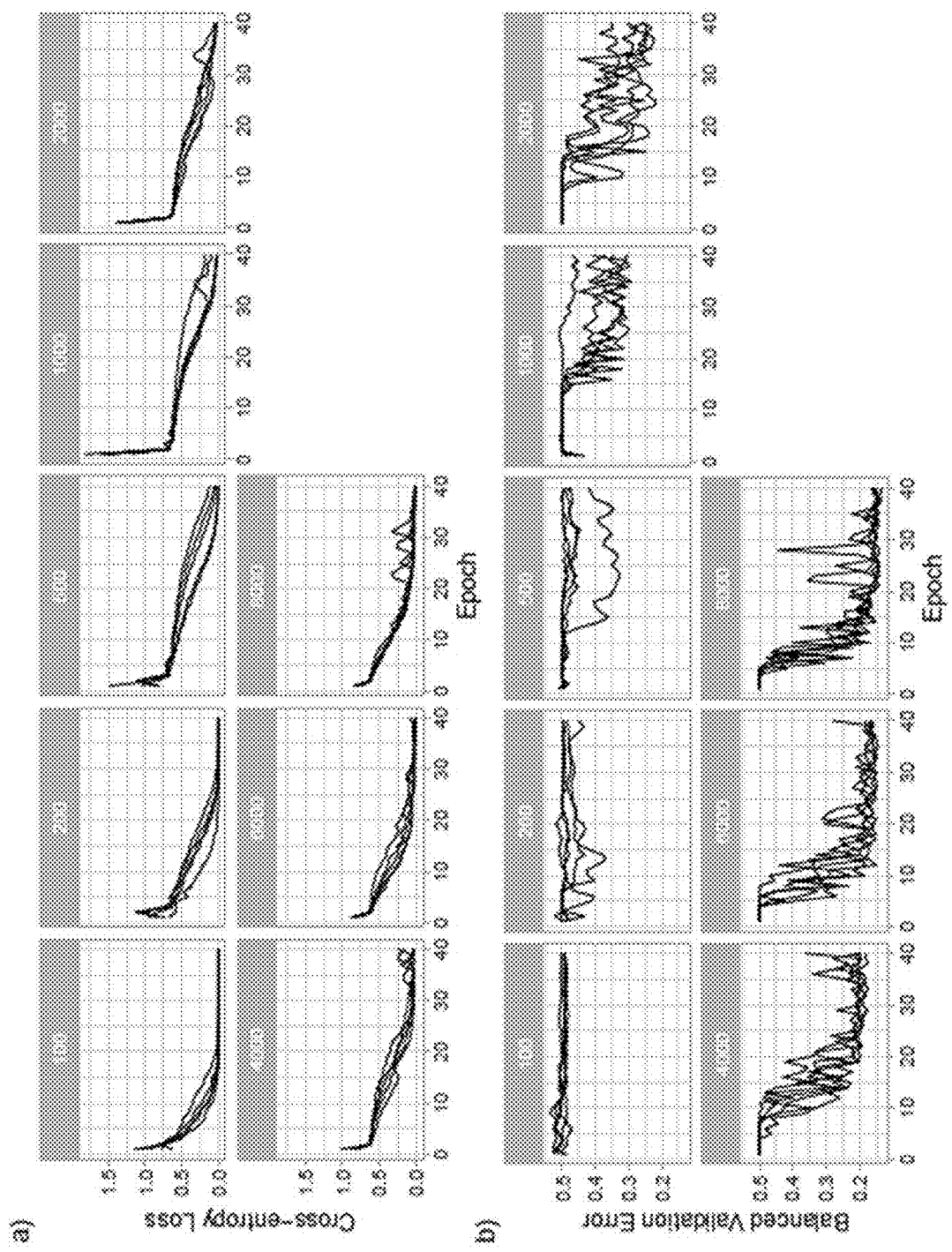
Figure 17C:
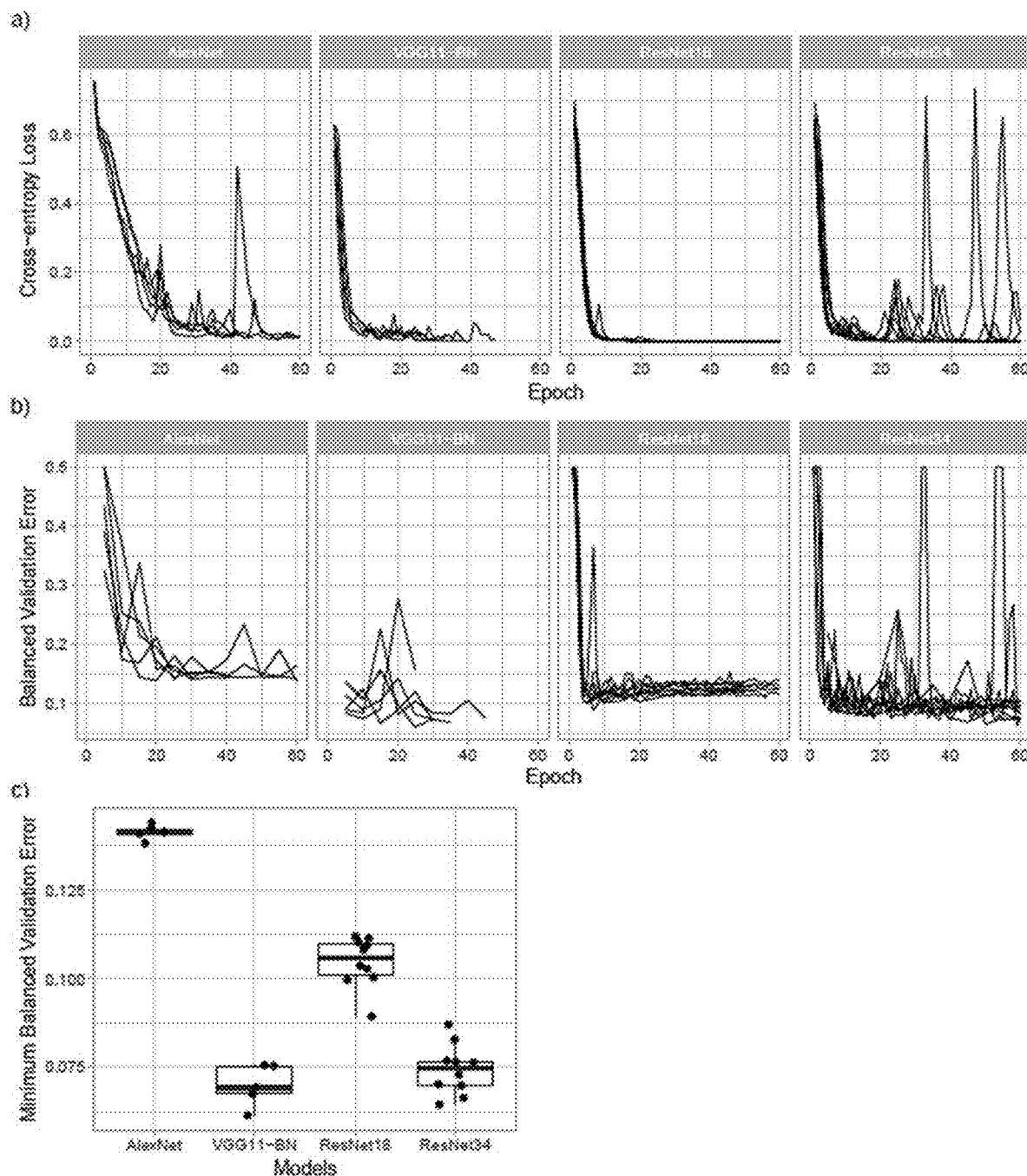

Feature Embedding Visualization: Understanding what features the model uses to classify a tile is an important bottle-neck of current clinical applications of deep learning. One can gain insight by visualizing a projection of the feature space in two dimensions using dimensionality reduction techniques such as PCA. 50 tiles were sampled from each test slide, in addition to its top-ranked tile, and extracted the final feature embedding before the classification layer. Shown in FIG. 17A are the results of the ResNet34 model. From the 2D projection, a clear decision boundary between positively and negatively classified tiles can be seen. Interestingly, most of the points are clustered at the top left region where tiles are rarely top-ranked in a slide. By observing examples in this region of the PCA space, it can be determined that they are tiles containing stroma. Tiles containing glands extend along the second principal component axis, where there is a clear separation between benign and malignant glands. Other top-ranked tiles in negative slides contain edges and inked regions. The model trained only with the weak MIL assumption was still able to extract features that embed visually.

Augmentation Experiments

Figure 17D:
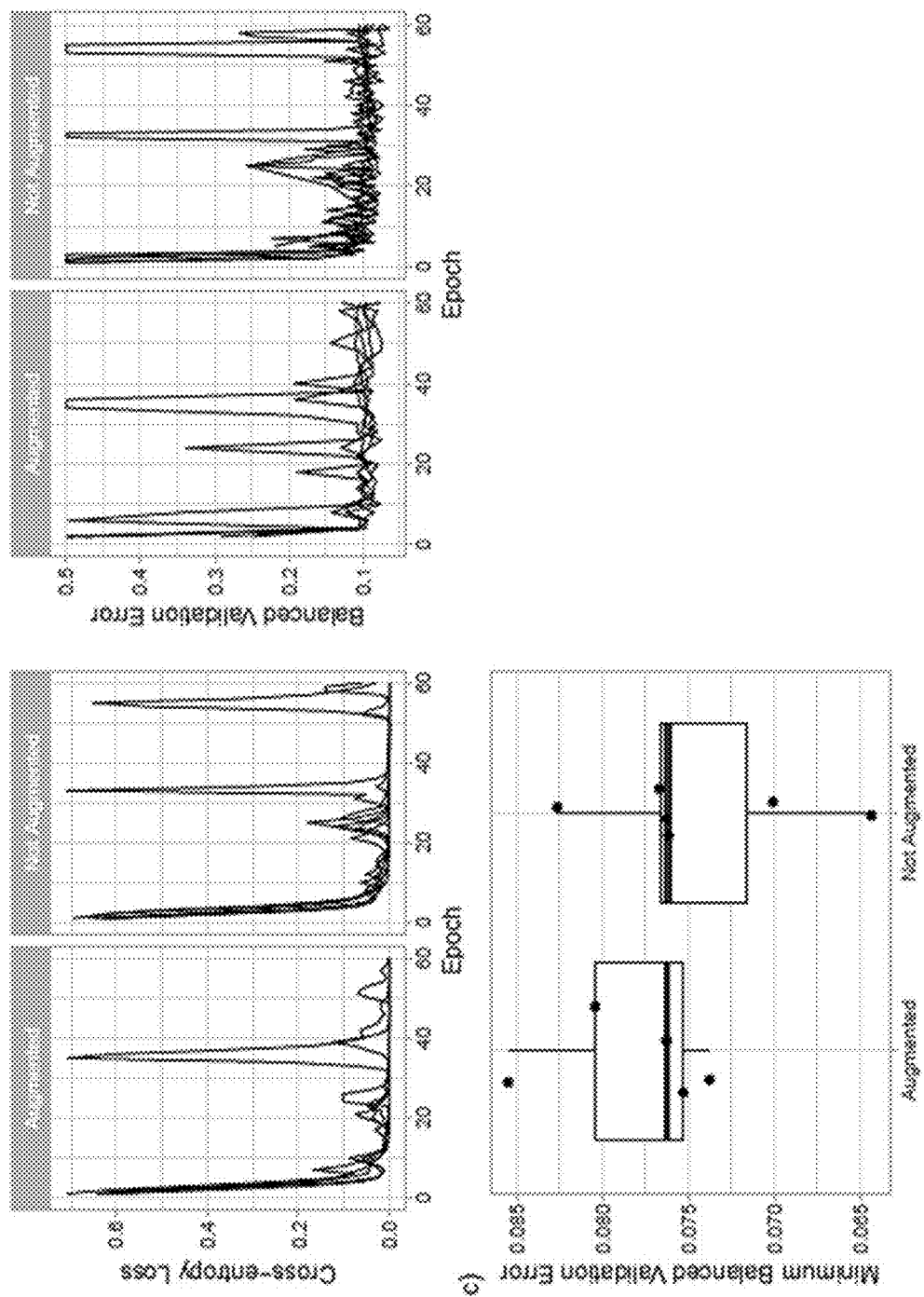

A small experiment with a ResNet34 model was run to determine whether augmentation of the data with rotations and flips during training could help lower the generalization error. The results are presented in FIG. 17D, showed no indication of a gain in accuracy when using augmentation.

Magnification Comparison

Figure 17E:
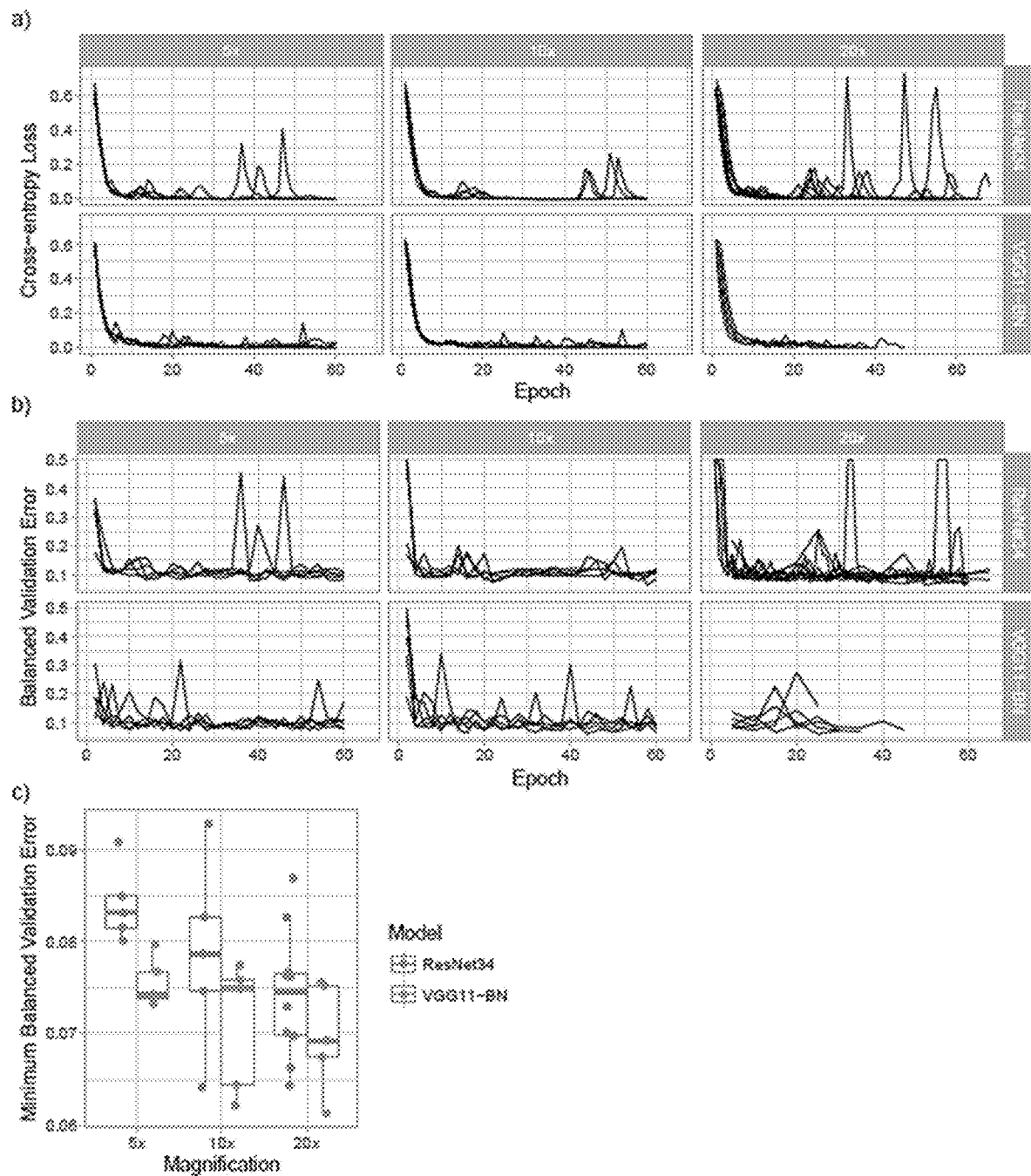

VGG11-BN and ResNet34 models were trained with tiles generated at 5× and 10× magnifications. Lowering the magnification led consistently to higher error rates across both models. Training curves and validation errors are shown in FIG. 17E. Ensemble models were also generated by averaging or taking the maximum response across different combinations of the three models trained at different magnifications. On the test set these naive multi-scale models outperformed the single-scale models, as can be seen in the ROC curves in FIG. 16(b). In particular, max-pooling the response of all the three models resulted in the best results with an AUC of 0.979, a balanced error of 5.8% and a false negative rate of 4.8%.

7. Conclusions

In this study the performance of convolutional neural networks under the MIL framework for WSI diagnosis was analyzed in depth. Focus was given on needle biopsies of the prostate as a complex representative task and the largest dataset in the field with 12,160 WSIs was obtained. Exploratory experiments on a subset of the data revealed that shallower networks without batch normalization, such as AlexNet and VGG11, were preferable over other architectures in this scenario. In addition, it was demonstrated that a multi-scale approach consisting of a pool of models, learned at different magnifications, can boost performance. Finally, the model was trained on the full dataset at 20× magnification and, while the model was only run for less than 200 steps, a balanced error rate of 13% was achieved on the best performing model and an AUC of 0.946.

The performance of the pipelines can be optimized to be able to run training in a fraction of the time. Investigation can be done on how to add supervision from a small pool of pixel-wise annotated slides to increase accuracy and achieve faster convergence. In addition, this MIL pipeline can be tested on other types of cancer to further validate the widespread applicability of the method described herein.

In addition, it was demonstrated that training on high-performing models for WSI diagnosis only using the slide-level diagnosis and no further expert annotation using the standard MIL assumption is possible. It was shown that final performance greatly depends on the dataset size. The best performing model achieved an AUC of 0.98 and a false negative rate of 4.8% on a held-out test set consisting of 1,824 slides. Given the current efforts in digitizing the pathology work-flow, approaches like these can be extremely effective in building decision support systems that can be effectively deployed in the clinic.

8. Supplemental

Slide Tiling

Figure 5:
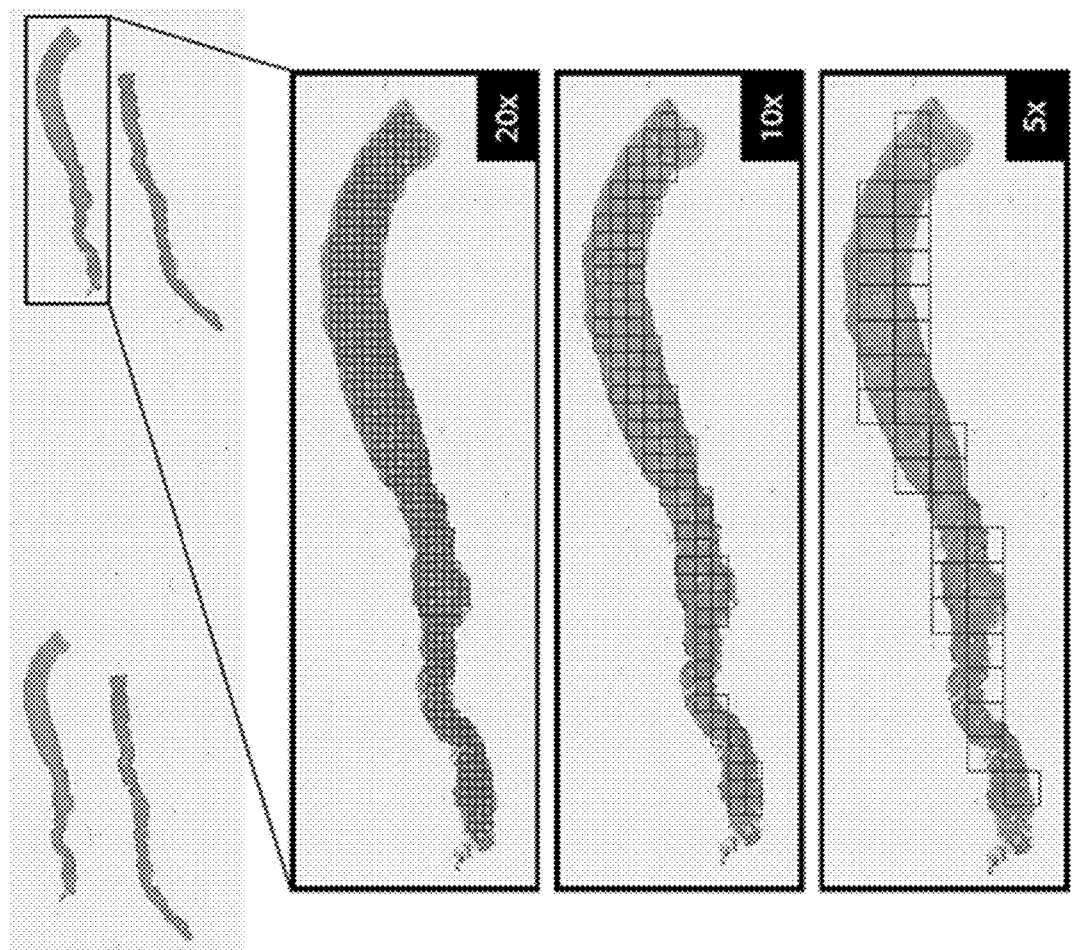
FIG. 5 depicts an example of a whole slide image with slide tiles at various magnification factors.

Referring to FIG. 5, shown is an example of a slide tiled on a grid with no overlap at different magnifications. The slide is the bag and the tiles constitute the instances of the bag. In this work instances at different magnifications are not part of the same bag. An example of a slide tiled on a grid with no overlap at different magnifications. The slide is the bag and the tiles constitute the instances of the bag. In this work instances at different magnifications are not part of the same bag.

Bag Composition

Figure 6A:
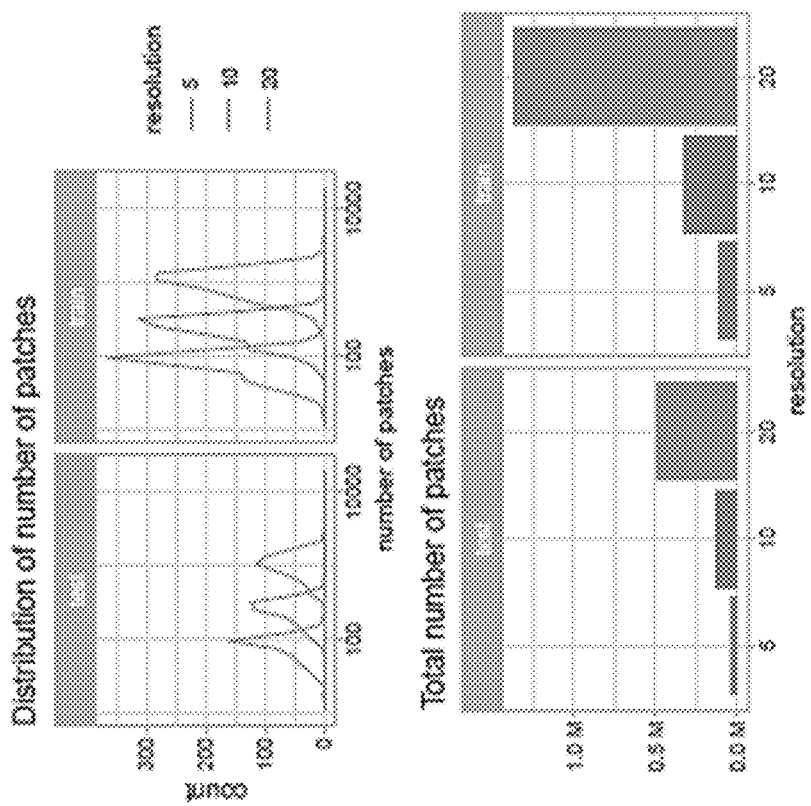
FIGS. 6A-C each depict graphs of statistics on compositions of bags for training datasets.
Figure 6B:
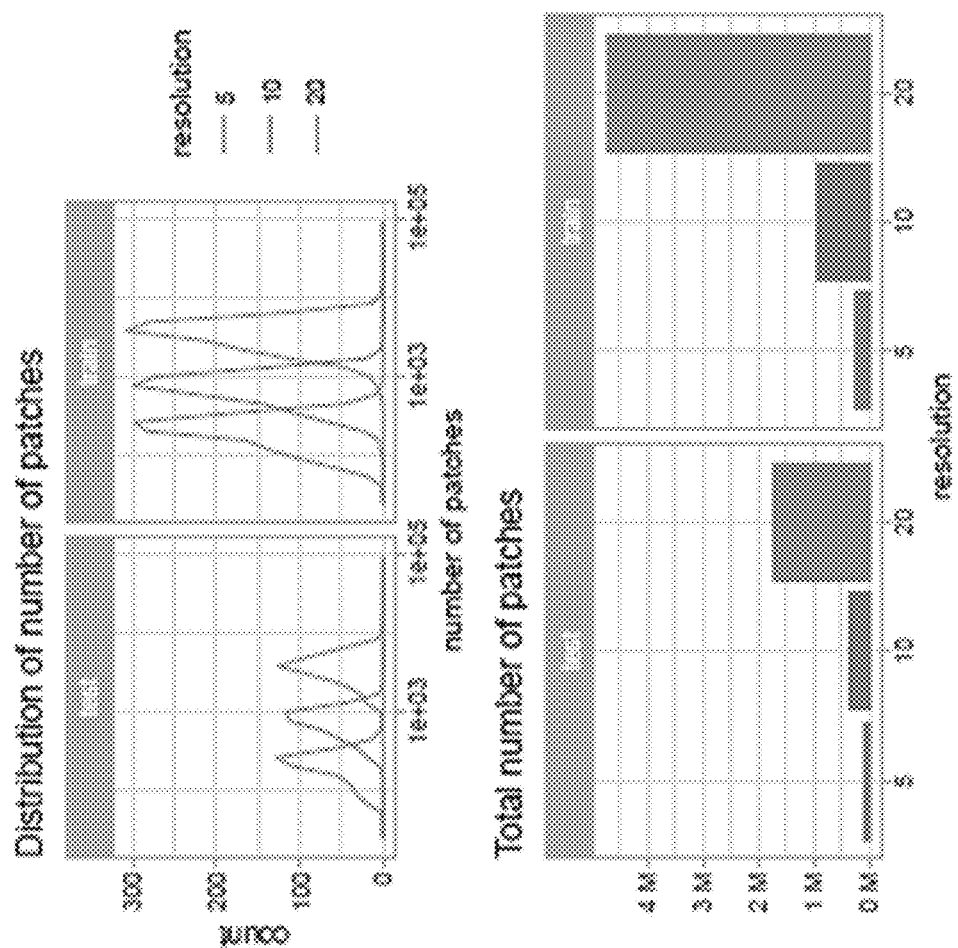
Figure 6C:
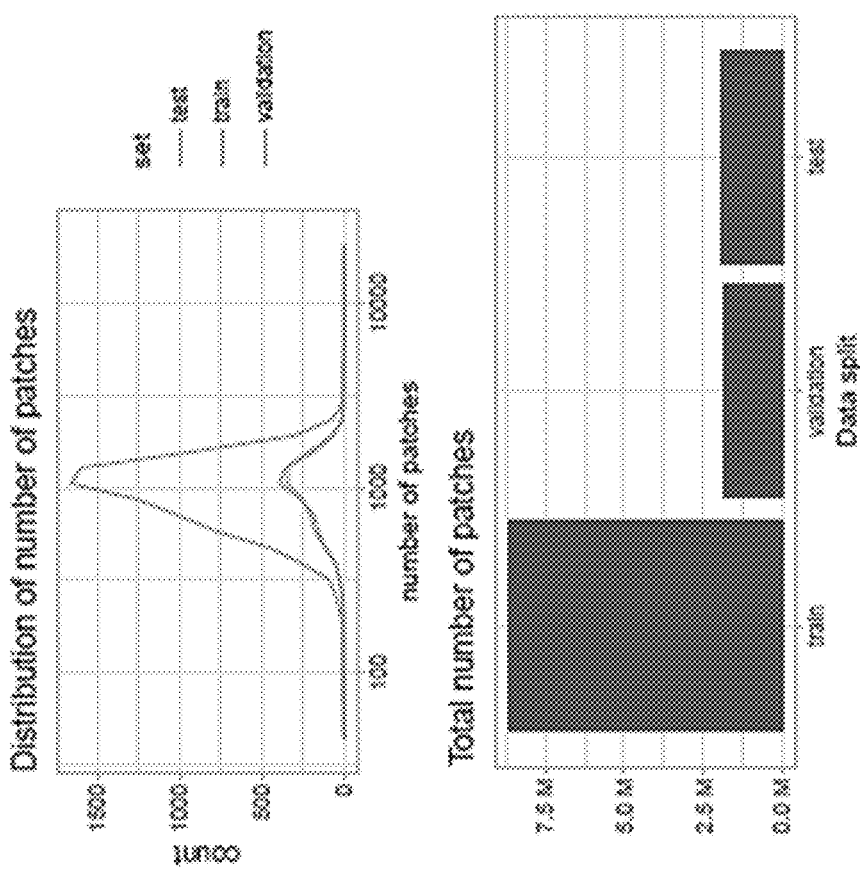

FIG. 6A illustrates some statistics on the composition of the bags for the exploratory dataset. FIG. 6B illustrates some statistics on the composition of the bags for the exploratory dataset tiled with 50% overlap. FIG. 6C illustrates some statistics on the composition of the bags for the full dataset consisting of 12,160 slides.

Architecture Comparisons

Figure 7A:
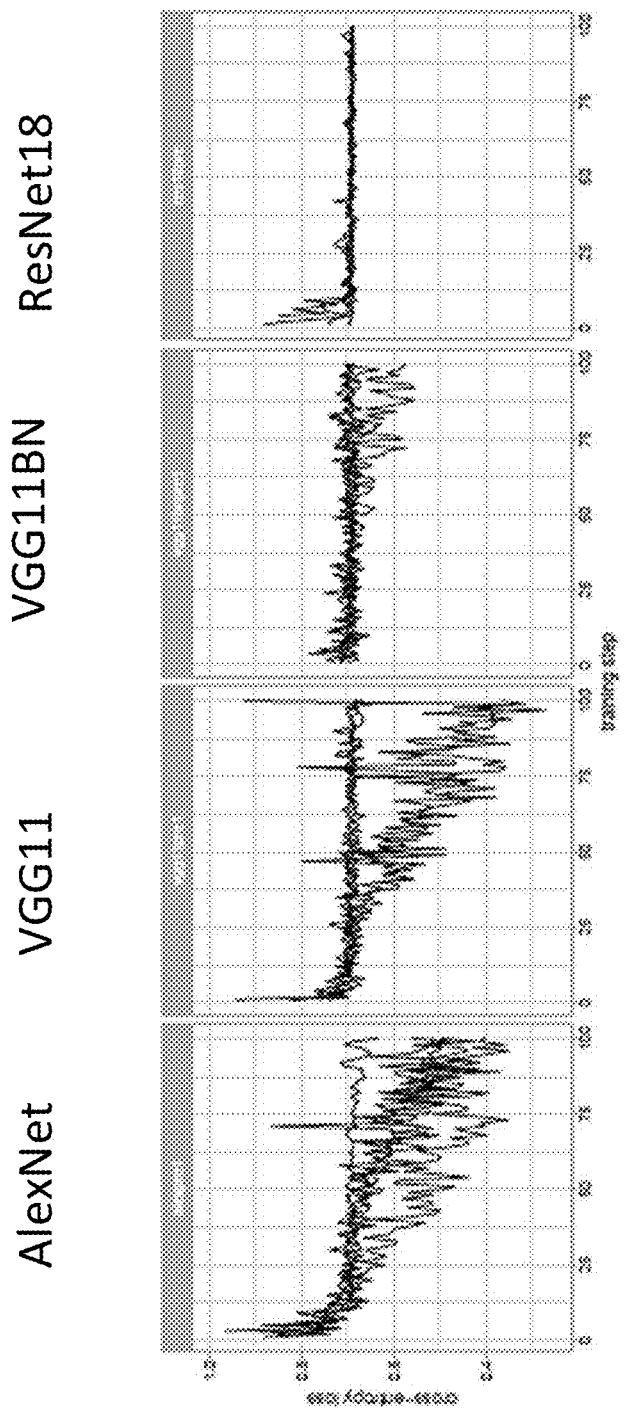
FIGS. 7A and 7B each depict graphs of performance of models in experiments.

Referring now to FIG. 7A, shown are setups for exploratory experiments. Standard MIL setup at 20× magnification with no overlap; adam optimizer with starting learning rate of 0.0001 for 100 steps. The training loss is plotted for different architectures. To note how AlexNet and VGG11 are able to reduce the loss, while VGG11BN and ResNet18 are stuck in a suboptimal minimum.

Classic MIL AlexNet Training

Figure 7B:
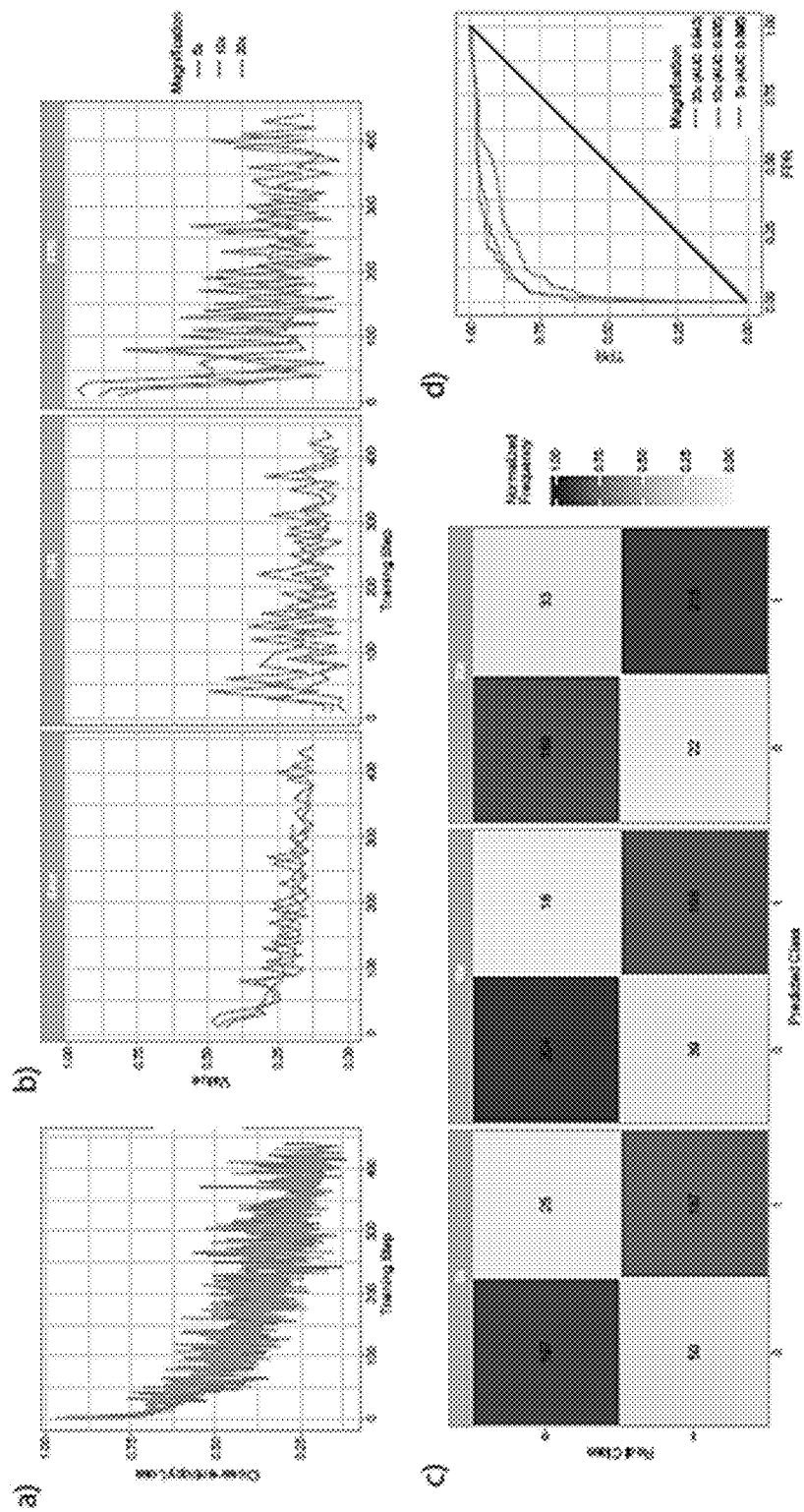

Referring now to FIG. 7B, MIL training of an AlexNet at different magnifications. a) Training loss. b) Misclassification error, False Negative Rate and False Positive Rate on the validation set. c) Confusion matrices of the best models on the validation set for each magnification. d) ROC curves of the best models on the validation set for each magnification.

True Positives

Figure 8A:
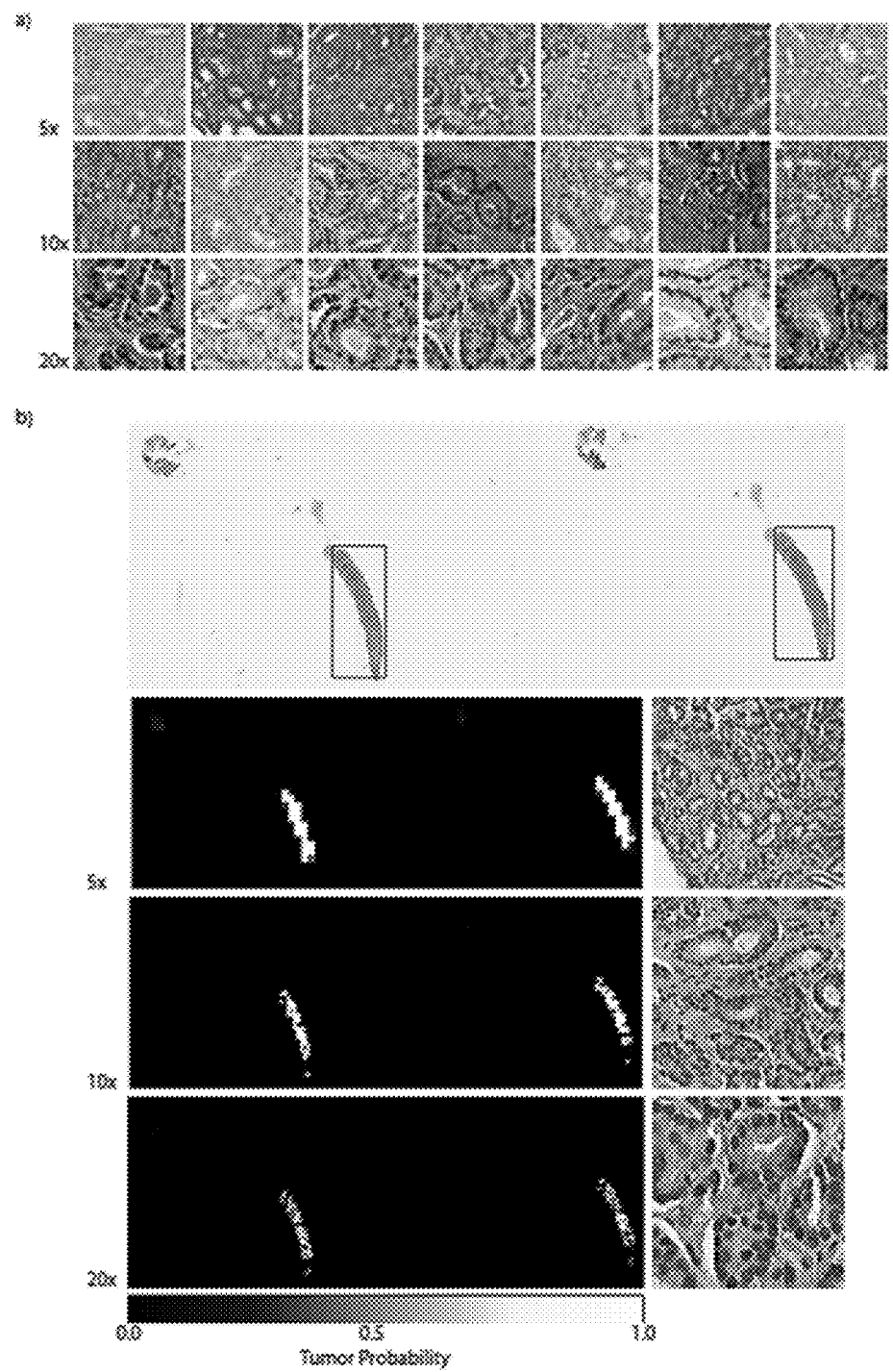
FIGS. 8A-C each depicts whole slide images with selections of features thereon using the multiple-instance learning trained model.

Referring now to FIG. 8A, shown is a selection of true positives from the best models on the validation set. a) Tiles with highest tumor probability within their respective slides. It is clear the model reacts strongly to malignant glands at all magnifications. b) In depth analysis of a random true positive result. The red boxes on the original slide are the ground truth localization of the tumor. The heat-maps are produced at the three magnifications and their respective highest probability tiles are also shown. In some case, the heat-maps can be used for localization of the tumor.

False Positives

Figure 8B:
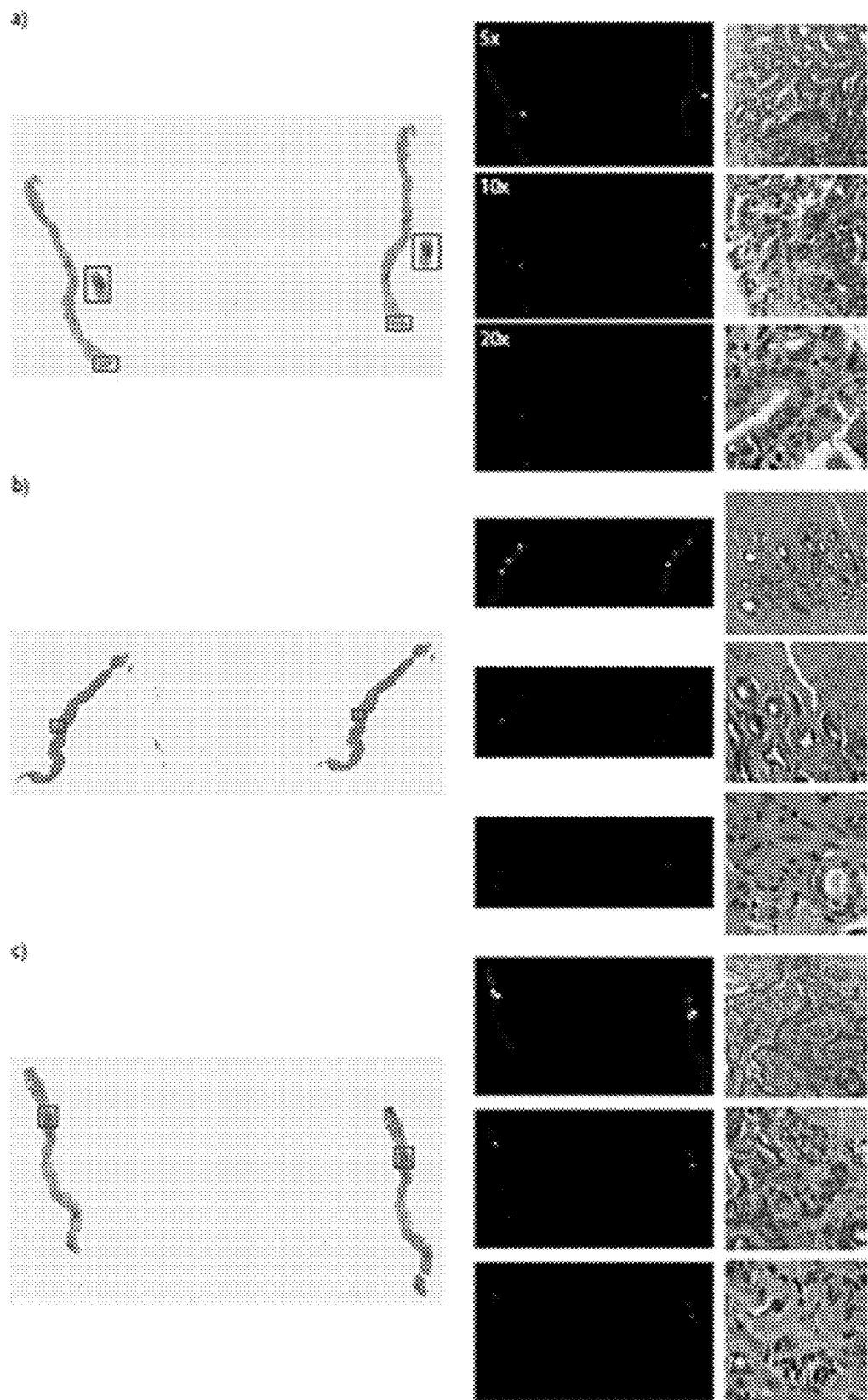

Referring now to FIG. 8B, shown are three examples of false positive slides on the validation set. These are all the cases that were mistakenly classified by the best models at each magnification tested. Inside the red rectangles are the tissue areas with a prostate cancer mimicker. a) The slide contains portions of seminal vesicle tissue. b) The slide presents areas of adenosis and general gland atrophy. c) The slide present areas of inflammation.

False Negatives

Figure 8C:
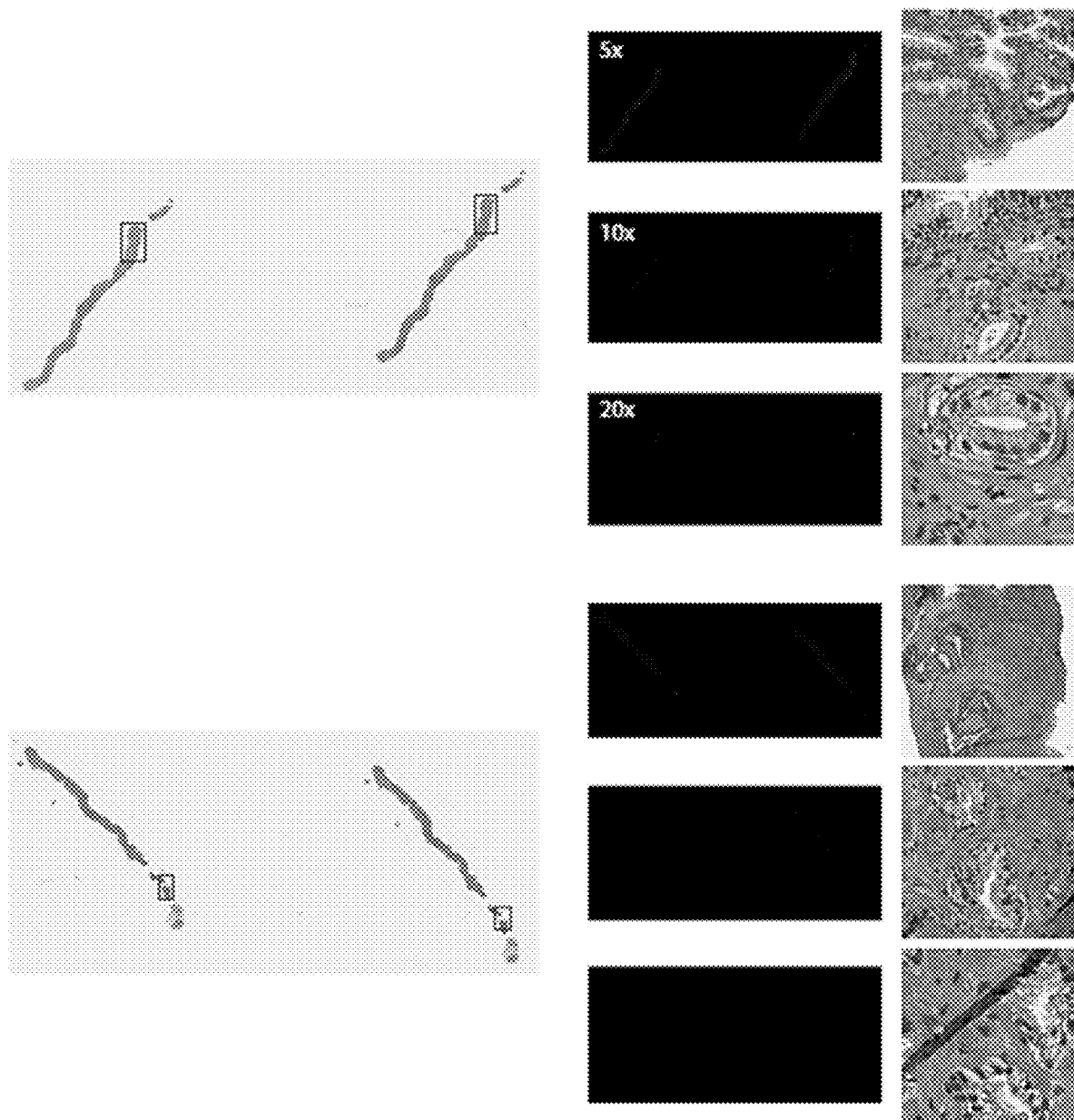

Referring now to FIG. 8C, shown are two examples of false negative slides on the validation set. The false negatives are in general cases where the tumor regions are particularly small.

Naive Multi-Scale Performance

Figure 10A:
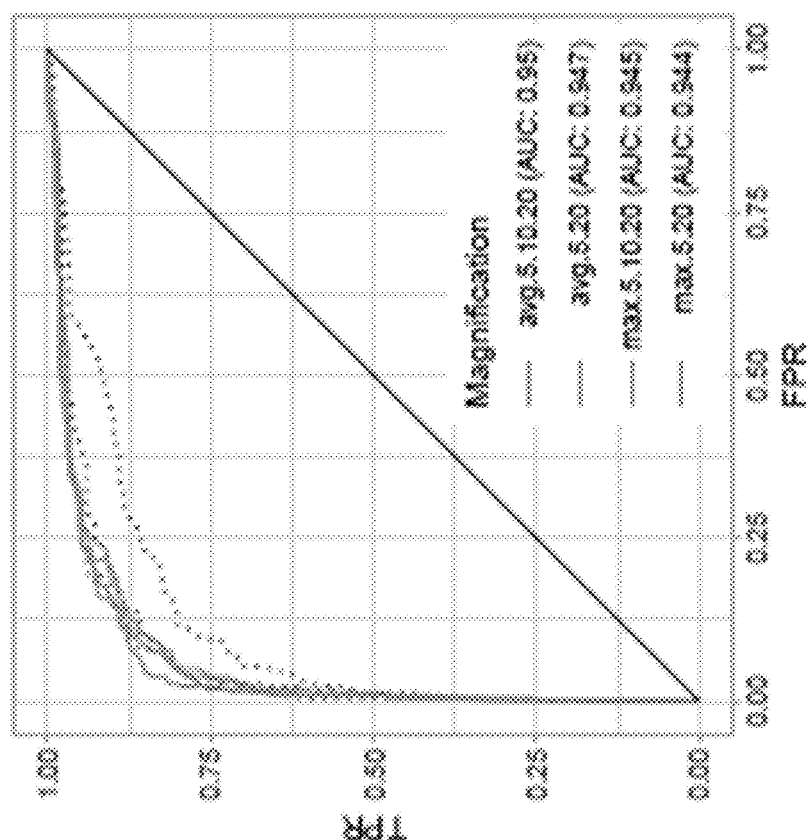
FIGS. 10A and 10B each depict line graphs of receiver operating characteristics (ROC) of the models.

Referring now to FIG. 9, shown is a table of a performance comparison of the classic MIL approach and the naive multi-scale version. A significant performance boost is observed by combining the prediction from multiple models. Referring now to FIG. 10A, shown are ROC curves for the naive multi-scale approach. The dotted lines are the ROC curves for each model alone. The performance of the three models together is improved as shown by the higher AUCs and overall error rates.

MIL with Overlap

Previous results suggested that especially for lower magnifications, tiling the slides with no overlap may be detrimental to the final performance. The experiments were repeated with 50% overlap of the tiles at every magnification. The bags at 5× magnification now contain several hundred instances, for a total of al-most half a million instances. The increased number of instances slows down the training considerably, especially at 20×, where after 160 hours only little over 100 steps were completed. Only the model trained at 5× magnification was trained for a number of steps comparable with its non-overlap counterpart. Nonetheless, performance showed only a minor improvement with overlapping instances compared to non-overlapping instances. Training Loss, Errors on the validation dataset and other performance metrics are presented in FIG. 10B.

Figure 10B:
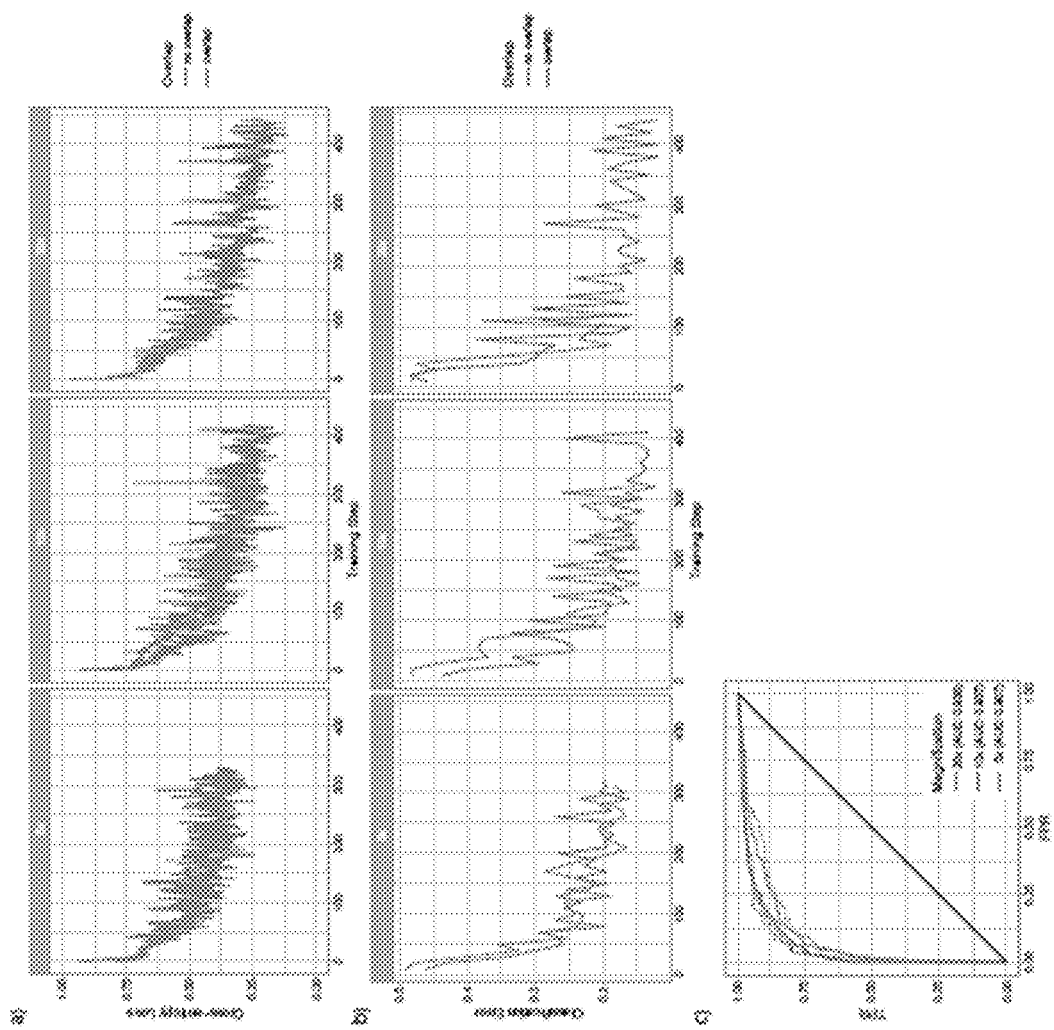

Referring to FIG. 10B, shown is performance of MIL trained with overlap. a) Training loss. b) Error measures on the validation set. c) ROC curves comparison with models trained without overlap. Only the 5× magnification model was trained long enough the be comparable with the "non-overlap" models. The overlap model trained at 5× magnification shows a slightly improved performance over its non-overlap counterpart.

Learned Multi-Scale Models

The results on the naive multi-scale approach are encouraging to try to learn feature at different scales within the same model. Three architectures were tested: (i) The "single" model uses as input a 6-channel image where the first three channels are for a 20× image and the second three channels are for a 5× image, both centered around the same pixel. (ii) The "double-sum" model has two parallel feature extractor, one for the 20× image and one for the 5× image. The features are then added element-wise and fed to a classifier. (iii) The "double-cat" model is very similar to the "double-sum" model but the features coming from the two streams are concatenated instead of added.

Figure 11:
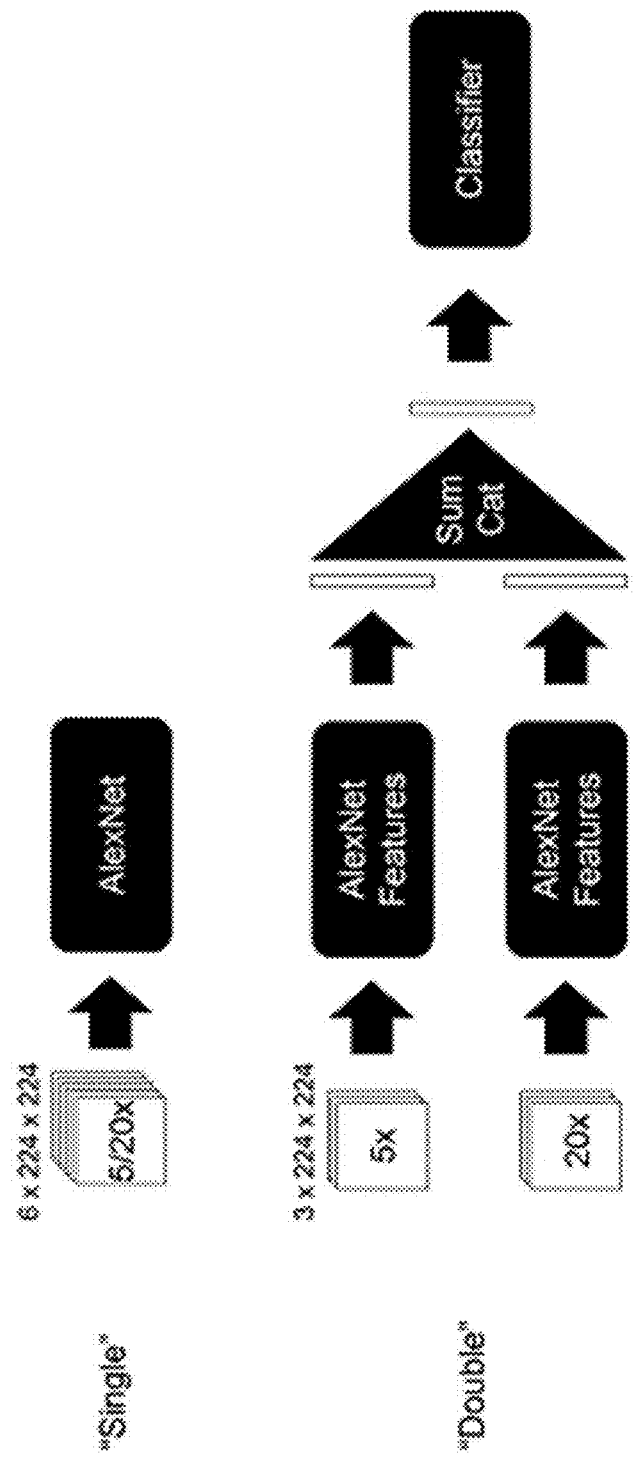
FIG. 11 depicts a schema of a model architecture multi-scale multiple instance learning experiments.

Referring now to FIG. 11, shown is a schematic of the three models. Model architectures for the learned multi-scale MIL experiments. The models receive as input a tile at 5× and 20× magnification. The tiles can be stacked into a "single" stream, or they can each go through parallel feature extractors. The features can then either be summed element-wise or concatenated before being fed to the final classifier.

Figure 12A:
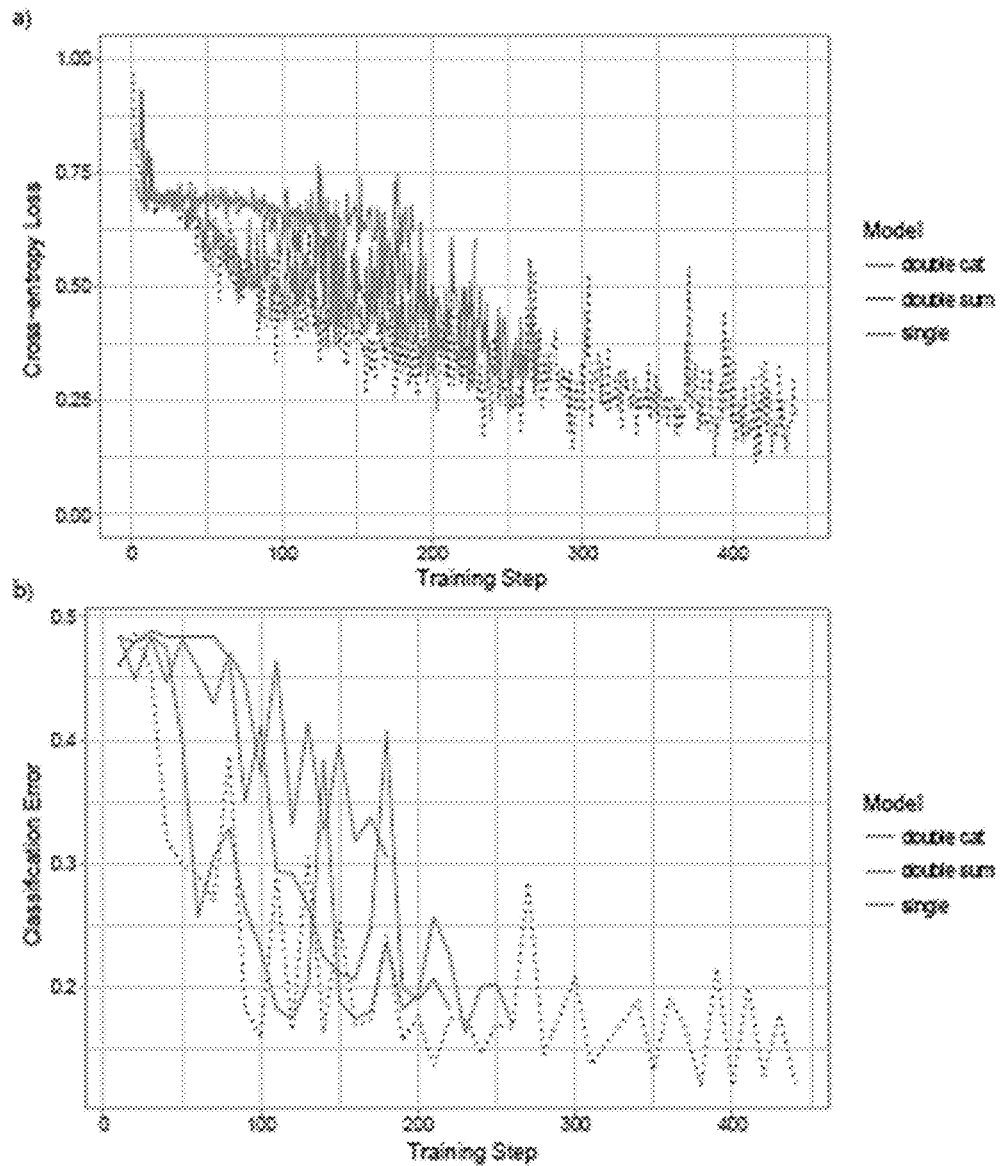
FIGS. 12A and 12B each depict line graphs showing training loss and classification error of various models.

The tiling for these experiments is done at 20× magnification without overlap, as before, but now two tiles are extracted at each time, one at 5× and one at 20×. The 5× tiles have 75% overlap. Referring now to FIG. 12A, shown are performance of the trained multi-scale experiments in comparison with the performance of the 20× magnification experiment from previous sections (dotted line). a) Training loss. b) Classification error on the validation set. The pipeline is slower than the non-multi-scale approach and fewer training steps could be completed. The performance of the "double" models is comparable to the 20× magnification model, while the "single" model seems to performs significantly worse. The results shown indicate that performance of the "double-sum" and "double-cat" models is comparable to that of the 20× magnification experiment, while the "single" model performs significantly worse. This experiment suggests that training models at different magnifications gives better results, but more experiments should be conducted to rule out the benefits of a trained multi-scale approach.

Large-Scale MIL Training

Figure 12B:
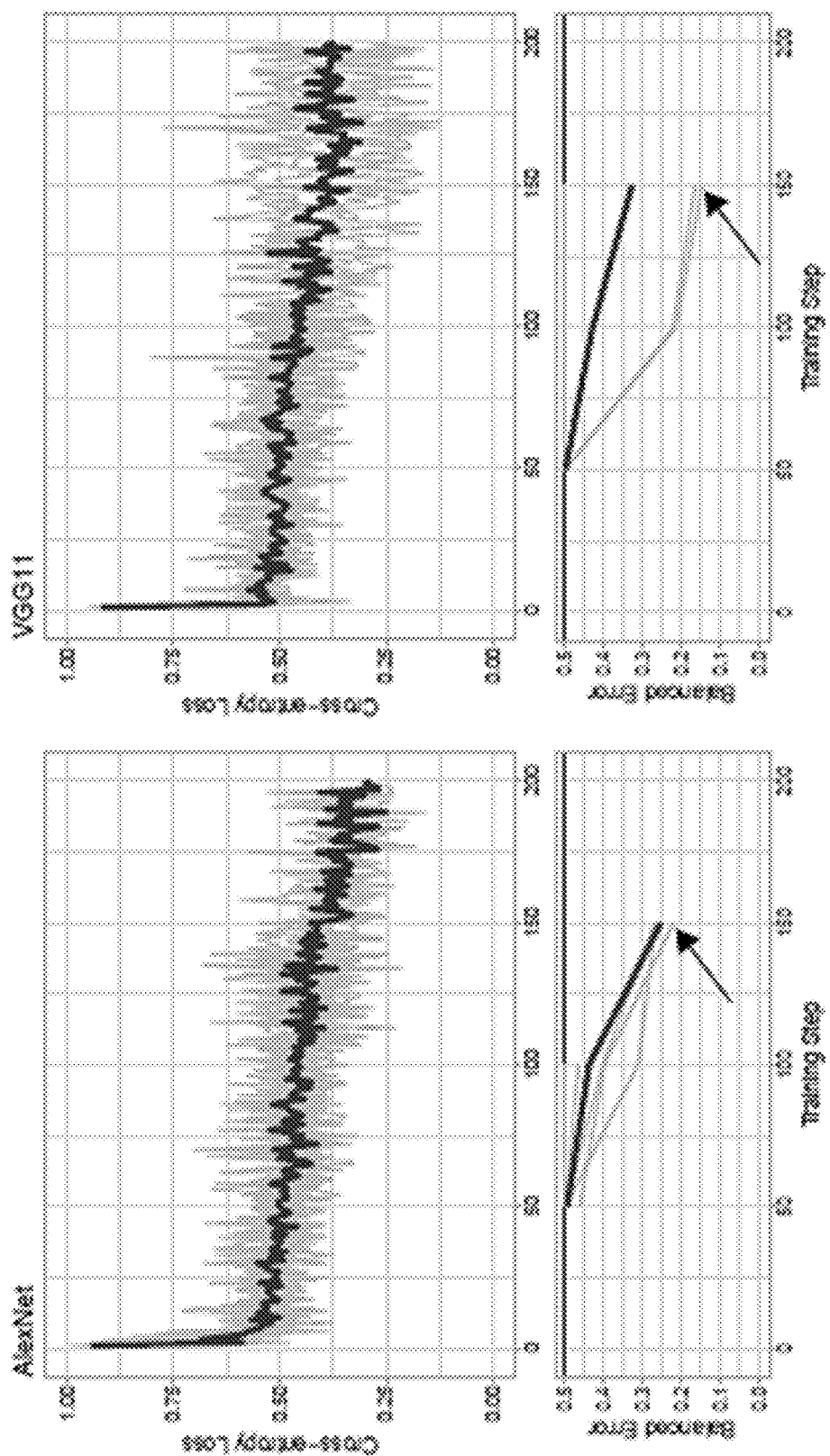

Referring now to FIG. 12B, shown are results from the large-scale training experiments on AlexNet (left column) and VGG11 (right column). Training loss and validation balanced error are plotted in the first and second rows respectively. The experiments were run 4 times each (gray traces) and the average curve is shown in red. While the AlexNet curve all show diminishing loss, in the VGG case, two of the four curves were stuck in a suboptimal minimum. The arrows point to the models chosen for the final testing on the test. Referring now to FIG. 13, shown are the confusion matrices for the best AlexNet and VGG11 models on the test set.

B. Towards Clinical-Level Decision-Support Systems in Computational Pathology

In computational pathology, the use of decision-support systems powered by state-of-the-art deep-learning solutions has been hampered by the lack of large labeled datasets. Previously, studies have relied on datasets consisting of a few hundred slides, which are not sufficient to train models that can perform in clinical practice. To overcome this bottleneck, a dataset including 44,732 whole slides from 15,187 patients was gathered across three different cancer types. Proposed is a novel deep-learning system under the multiple instance learning (MIL) assumption, where only the overall slide diagnosis is necessary for training, thus avoiding all the expensive pixel-wise annotations that are usually part of supervised learning. The proposed method works at scale and requires no dataset curation at any stage. This framework was evaluated on prostate cancer, basal cell carcinoma (BCC) and breast cancer metastases to axillary lymph nodes. It is demonstrated that classification performance with area under the curve (AUC) above 0.98 for all cancer types. In the prostate dataset, this level of accuracy translates to clinical applicability by allowing pathologists to potentially exclude 75% of slides while retaining 100% sensitivity. These results open the way for training accurate tumor classification models at unprecedented scale, laying the foundation for computational decision-support systems that can be deployed in clinical practice.

There has been a strong push towards the digitization of pathology with the birth of the new field of computational pathology. The availability of increasingly large digital pathology data, coupled with impressive advances in computer vision and machine learning in recent years, offer the perfect combination for the deployment of decision-support systems in the clinical setting. Translating these advancements in computer vision to the medical domain, and to pathology in particular, comes with challenges that remain unsolved, despite the notable success from dermatology and ophthalmology, where human level diagnosis is achieved on dermoscopy and optical coherence tomography (OCT) images, respectively. Unlike in other medical domains, the lack of large datasets which are indispensable for training high-capacity classification models, has set back the advance of computational pathology. The CAMELYON16 challenge for breast cancer metastasis detection contains one of the largest labeled datasets in the field, with a total of 400 whole-slide images (WSIs). But this amount of cases is extremely small compared to the millions of instances present in the popular ImageNet dataset. One widely adopted solution to the scarcity of labeled examples in pathology is to take advantage of the size of each example. Pathology slides scanned at 20× magnification produce image files of several gigapixels. About 470 WSIs scanned at 20× contain roughly the same number of pixels as the entire ImageNet dataset. By breaking the WSIs into small tiles, it is possible to obtain thousands of instances per slide, enough to train high-capacity models from a few hundred slides. Unfortunately, tile-level annotations are required for supervised learning, but these are prohibitively expensive and time consuming to produce, especially in pathology. There have been several efforts along these lines. Despite the success of computational algorithms on carefully crafted datasets, the performance of these models does not transfer to the real-life scenarios encountered in clinical practice because of the tremendous variance of clinical samples that is not captured in small datasets. Experiments presented in this article will substantiate this claim.

Another possibility, and the one that is thoroughly explored in this study, is to leverage the slide-level diagnosis, which is readily available from anatomic pathology laboratory information systems (LIS) or electronic health records (EHR), to train a classification model in a weakly supervised manner. Until now, training high-capacity models with clinical relevance at scale and only using slide-level supervision was not possible, due to the lack of large WSI datasets. To address this fundamental problem and to demonstrate how the proposed method can be seamlessly applied to virtually any type of cancer, three datasets of unprecedented size are gathered in the field of computational pathology: (i) a prostate core biopsy dataset consisting of 24,859 slides; (ii) a skin dataset of 9,962 slides; and (iii) a breast metastasis to lymph nodes dataset of 9,894 slides. Each one of these datasets is at least one order of magnitude larger than all other datasets in the field. In total, an equivalent number of pixels is analyzed from 88 ImageNet datasets (Table 1). It should be noted that the data were not curated. The slides in this work are representative of slides generated in a true pathology laboratory, which include common artifacts, such as air bubbles, microtomy knife slicing irregularities, fixation problems, cautery, folds, and cracks, as well as digitization artifacts, such as striping and blurred regions.

Figure 18:
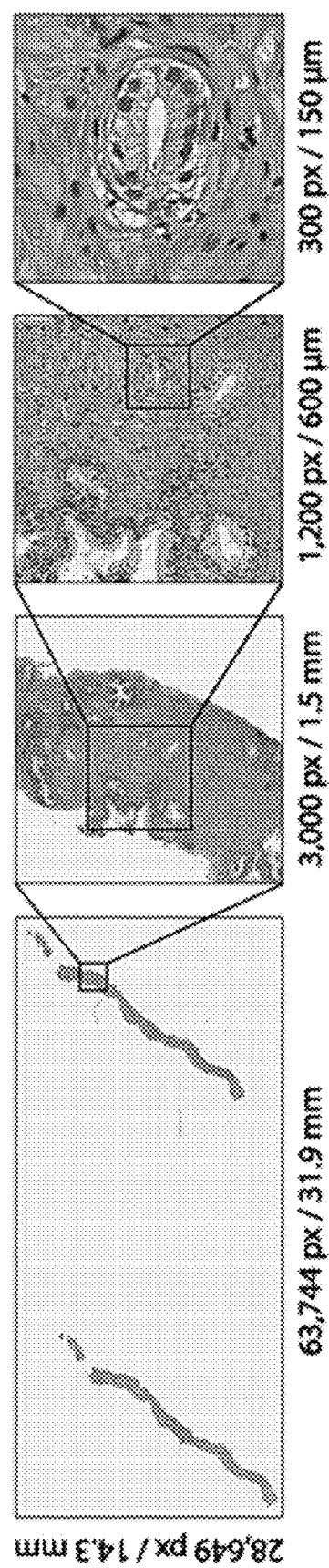
FIG. 18 depicts an example whole slide image for prostate cancer biopsy.

The datasets chosen represent different but complementary views of clinical practice, and offer insight into the types of challenges a flexible and robust decision support system should be able to solve. Prostate cancer, beyond its medical relevance as the leading source of new cancer cases and the second most frequent cause of death among men after lung cancers, can be diagnostically challenging, even for trained pathologists. Multiple studies have shown that prostate cancer diagnosis has a high inter- and intra-observer variability. Diagnosis is frequently based on the presence of very small lesions that comprise less than 1% of the entire tissue surface area (e.g., FIG. 18). Referring to FIG. 18, shown is a hematoxylin and eosin stained whole slide image for prostate cancer biopsy. The diagnosis can be based on very small foci of cancer that account for less than 1% of the tissue surface. In the slide above, only about 6 small tumor glands are present. The right-most image shows an example of a malignant gland. Its relation to the entire slide is put in perspective to reiterate the difficulty of the task.

For prostate cancer, making diagnosis more reproducible and aiding in the diagnosis of cases with low tumor volume are examples of how decision-support systems can improve patient care. BCC—the most common skin cancer, with approximately 4.3 million individuals diagnosed annually in the US—rarely causes metastases or death. In its most common form (e.g. nodular), pathologists can readily identify and diagnose the lesion; however, given its high frequency, the volume of cases that a pathologist must report is increasing. In this scenario, a decision support system should streamline the work of the pathologist and lead to faster diagnosis. For breast cancer metastases to lymph nodes, a clinical support system could allow for prioritization of slides with a higher probability of metastasis to be presented to the pathologist for confirmation. This assistive model would lower false negative rates and enable automation of subsequent downstream clinical tasks, such as quantification of metastatic tumor volume for clinical staging purposes. Detection of breast cancer metastasis in lymph nodes is also important because it allows directly comparison of the proposed methods to the state-of-the-art WSI classification that was established based on the CAMELYON16 challenge.

Since the introduction of the MIL framework, there have been many reports in the literature on both the theory and application of MIL in computer vision. Although it provides a good framework for weakly supervised WSI classification, and despite its success with classic computer vision algorithms, MIL has seen relatively little application in medical image analysis and computational pathology, in part due to the lack of large WSI datasets. This disclosure takes advantage of the large datasets and propose a deep MIL framework where only the whole-slide diagnosis is needed to train a decision-support system capable of classifying digital slides on a large scale with a performance in line with clinical practice.

1. Context

Weak supervision at the WSI level instead of strong supervision may be used at the tile or pixel levels. In contrast, some approaches in radiology used a MIL approach for body part recognition in computerized tomography (CT) scans and applied MIL to mammogram classification. In pathology, the large margin principle for MIL was implemented in the context of manually engineered features. Current state-of-the-art methods for weakly supervised WSI classification rely on deep-learning models trained under variants of the MIL assumption. Typically, a two-step approach is used, where first a classifier is trained with MIL at the tile level and then the predicted scores for each tile within a WSI are aggregated in some way, usually through some pooling scheme or learning a histogram-based fusion model. One approach used an attention mechanism to generate a slide-level embedding, which was shown to be efficient and useful, especially in data-deprived domains. Unfortunately, its applicability to WSI is questionable given that the entirety of the bag must be processed at the same time, which is not feasible with WSIs.

The present disclosure is different because MIL supervision is used to learn a semantically rich tile vector representation. Such representation is then used in a recurrent neural network (RNN) to integrate the information across the slide and emit the final classification result (e.g., FIG. 19). Importantly, all previous works used small datasets, which precludes a proper estimation of the clinical relevance of the learned models. The model is trained on tens of thousands of slides, a scale at which clinically relevant performance can be achieved.

2. Datasets

We collected three large datasets of hematoxylin and eosin (H&E)-stained digital slides for the following tasks: (i) prostatic carcinoma classification, (ii) BCC classification and (iii) detection of breast cancer metastasis in axillary lymph nodes. A short description is given in Table 1. Unless otherwise stated, glass slides were scanned at Memorial Sloan Kettering Cancer Center (MSK) with Leica Aperio AT2 scanners at 20× equivalent magnification (0.5 µm/pixel). The prostate dataset consisted of 12,132 core needle biopsy slides produced and scanned at MSK (we will refer to these as in-house slides). A subset of 2,402 slides were positive for prostatic carcinoma (i.e. contained Gleason patterns 3 and above). An in-depth stratification by Gleason grade and tumor size is included in Table 2 below. A set of 12,727 prostate core needle biopsies was retrieved for a second opinion from other institutions around the world. These slides were produced at their respective institutions but scanned on the whole-slide scanners at MSK. These consulation slides were not used during training, but only at test time. The skin dataset consisted of 9,962 slides from biopsies and excisions of a wide range of neoplastic and non-neoplastic skin lesions, including 1,659 BCCs with all common histologic variants (superficial, nodular, micronodular, and infiltrative) represented. The breast cancer metastases dataset of axillary lymph nodes consisted of 9,894 slides, 2,521 of which contained macro-metastases, micro-metastases, or isolated tumor cells (ITCs). Included in this dataset were slides generated from intraoperative consultations (e.g. frozen section slides), in which the quality of staining varied from the standardized H&E staining protocols used on slides from formalin-fixed, paraffin-embedded tissue. The dataset also included patients treated with neo-adjuvant chemotherapy, which may be diagnostically challenging in routine pathology practice (i.e. small volume of metastatic tumor, therapy-related change in tumor morphology) and are known to lead to high false negative rates.

Across the three datasets, included were a total of 17,661 consultation slides coming from institutions within the US and other 44 countries. The datasets collected for each tissue type represented the equivalent of at least 1 year of clinical cases. Crucially, the diagnoses were retrieved from the original pathology reports in the anatomic pathology LIS at MSK. Diagnostic data retrieved from pathology reports are easily scalable as opposed to expert annotation for supervised learning which is time prohibitive at scale. The datasets were randomly divided at the patient level in training (70%), validation (15%) and test (15%) sets. The training and validation sets were used for hyper-parameter tuning and model selection. The final models were run once on the test set to estimate generalization performance.

Table 1: Datasets description. This study is based on a total of 44,732 slides from 15,187 patients across three different tissue types: prostate, skin and axillary lymph nodes. The prostate dataset was divided into in-house slides and consultation slides to test for staining bias. The class imbalance varied from 1:4 for prostate to 1:3 for breast. A total of 17,661 slides were submitted to MSK from more than 800 outside institutions in 45 countries for a second opinion. To put the size of the dataset in context, the last column shows a comparison in terms of pixel count with ImageNet, the state-of-the-art in computer vision, containing over 14 million images.

pleted for each condition. Minimum balanced error on the validation set for each run was used to decide the best condition in each experiment. Briefly, ResNet34 achieved the best results over other architectures tested (AlexNet, VGG11, VGG16, ResNet18, ResNet101, DenseNet201); using a class-weighted loss led to better performance overall, and weights were adopted in the range of 0.8-0.95 in subsequent experiments; given the scale of the data, augmenting the data with rotations and flips did not significantly affect the results. During training, the false negative errors were weighted more heavily to obtain models with high sensitivity. Histology contains information at different scales. In particular, for prostate histopathology, features at the cellular and gland level are both important for diagnosis but can be more easily appreciated at different magnifications. Hence, training a classifier at different magnifications is important to avoid losing potentially relevant information. For prostate, the highest magnification consistently gave better results; for BCC detection, 5x magnification showed higher accuracy. Interestingly, the error modes of models trained at different scales were only partially correlated. This observation is in line with the intuition that different scales may capture different features that could be integrated in a multi-scale approach. Finally, experiments were run to determine whether our dataset was large enough to saturate the error rate on the validation set. For these experiments, the prostate dataset (excluding the test portion) was split in a common validation set with 2,000 slides and training sets of different sizes (100, 200, 500, 1,000, 2,000, 4,000, 6,000 and 8,000), with each training dataset being a superset of all previous datasets.

| Dataset | Years | Slides | Patients | Positive slides | Consultation slides | ImageNet |
|---|---|---|---|---|---|---|
| Prostate In-house | 2016 | 12,132 | 836 | 2,402 | 0 | 19.8x |
| Prostate External | 2015-2017 | 12,727 | 6,323 | 12,413 | 12,727 | 29.0x |
| Skin | 2016-2017 | 9,962 | 5,325 | 1,659 | 3,710 | 21.4x |
| Axillary Lymph Nodes | 2013-2018 | 9,894 | 2,703 | 2,521 | 1,224 | 18.2x |
| Total | | 44,732 | 15,187 | | | 88.4x |

3. Results

MIL-Based Slide Classification

The MIL assumption in the context of WSI classification states that for negative slides, all its tiles are of negative class; for positive slides, there must exist one or more positive tiles, sometimes also referred to as discriminant tiles. The MIL assumption can be applied to deep learning as follows: given a model that predicts the probability of being class positive for a small tile, a full inference pass through the dataset is performed. Within each slide, the tiles are ranked according to their probability of being positive. The top most probable tiles for each slide are then used for training the model (FIG. 19). The top-ranking tiles from positive slides should have a probability of being positive close to 1. Conversely, top-ranking tiles from negative slides should have a probability of being positive close to 0. Hence, the model can be trained on the top-ranking tiles using a standard cross-entropy loss by assigning the slide level target to its respective tile. At prediction time, the MIL assumption determines that if one positive tile is found, the slide is predicted positive. An in-depth description is given in the Methods section.

Figure 20:
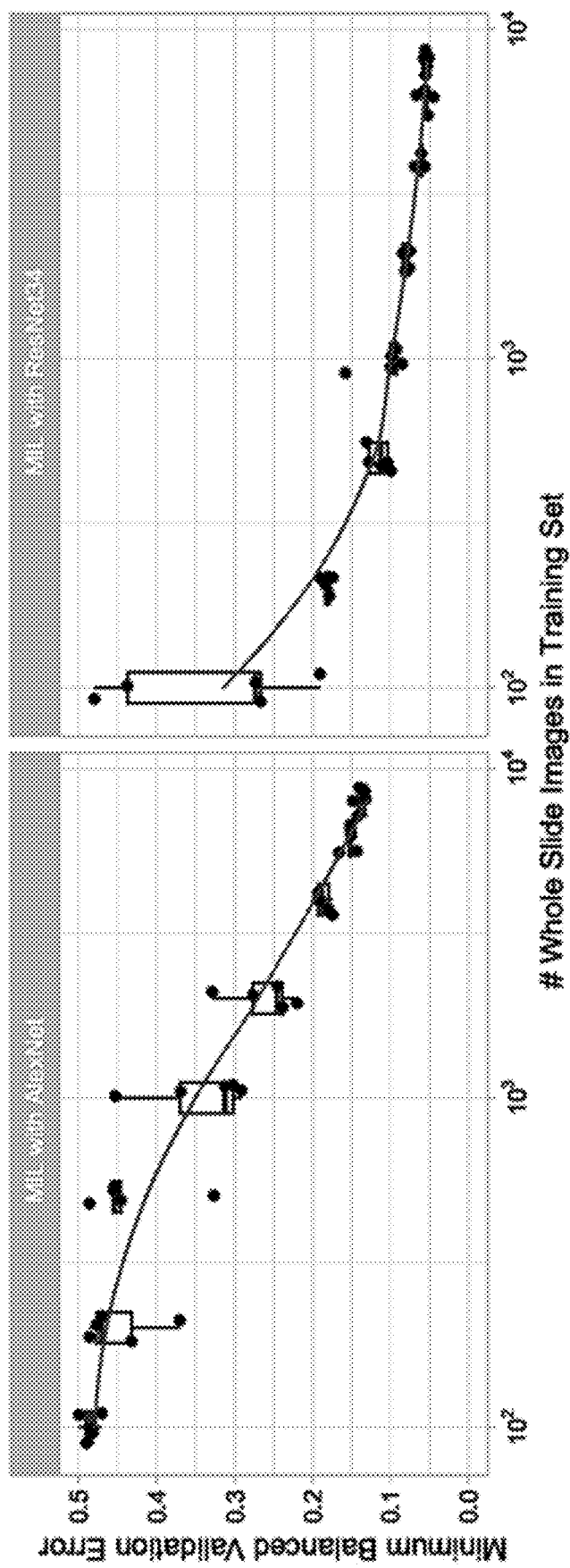
FIG. 20 depicts line graphs of validation error versus a number of whole slide images in training data.

First, a set of exploratory experiments were performed on the prostate dataset. At least five training runs were com- Referring to FIG. 20, the results indicate that while the validation error is starting to saturate for ResNet34, and further improvement can be expected from even larger datasets than the one collected for this study. Training was performed with datasets of increasing size. The experiment underlies the fact that a large number of slides is necessary for generalization of learning under the MIL assumption. ResNet architectures result in lower errors conditioned on the dataset size. Although the number of slides needed to achieve satisfactory results may vary by tissue type, it is observed that, in general, at least 10,000 slides are necessary for good performance.

Figure 26:
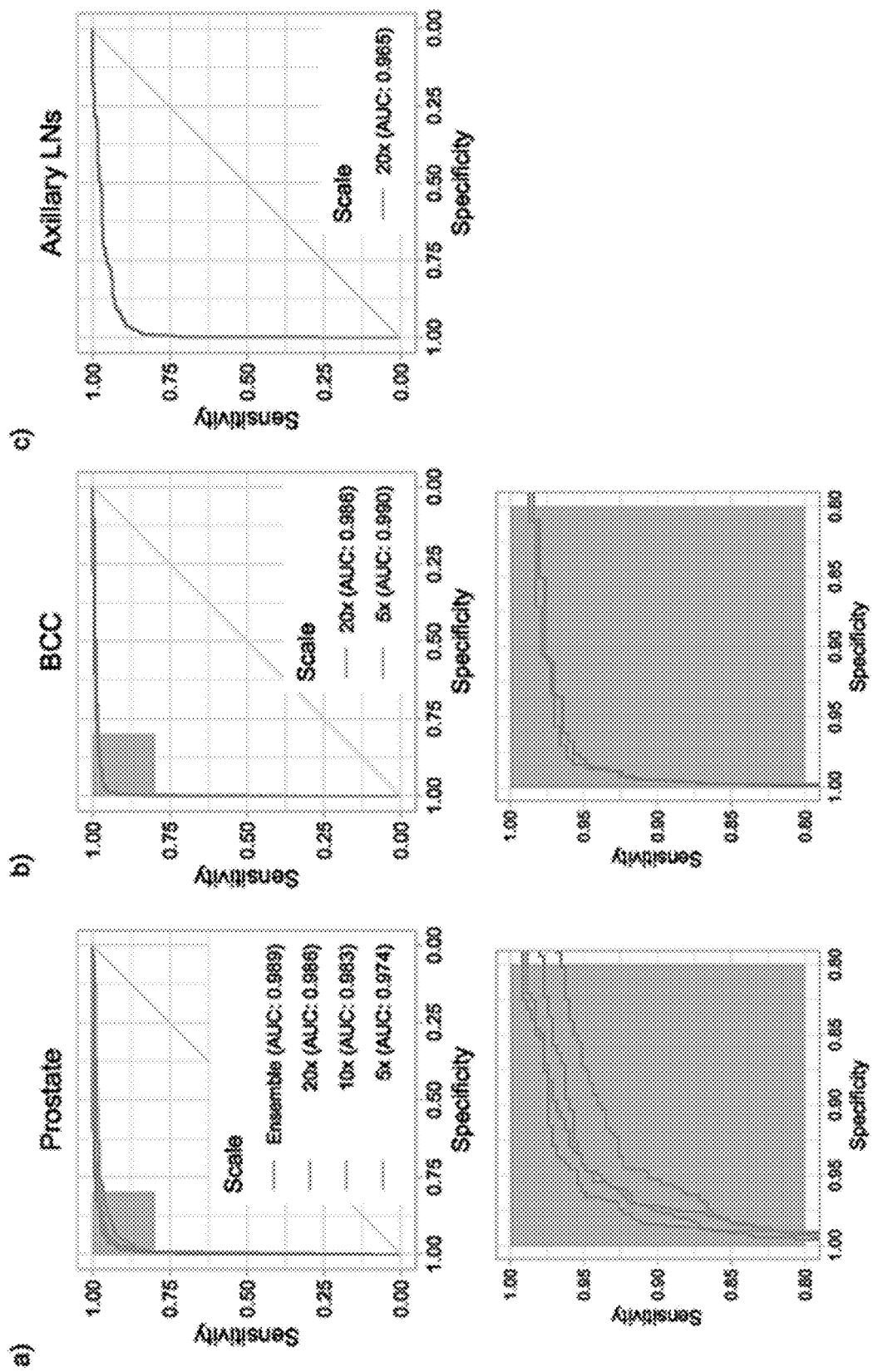
FIG. 26 depicts line graphs of classification performance for different cancer sets.

Performance on the test set was measured for ResNet34 architectures trained at different magnifications for each dataset (see FIG. 26). It was noticed that the error modes on the test set across magnification conditions were complementary: in prostate, for example, the 20x model performed better in terms of false negatives, while the 5x model performed better on false positives. This observation led to generating ensemble models by averaging or max-pooling the response across models trained at different magnifications. These naive multi-scale models outperformed the single-scale models for the prostate dataset in terms of accuracy and AUC, but not for the other datasets. The AUC for the models trained at 20× was 0.986, 0.986 and 0.965 on the test sets of the prostate, BCC and axillary lymph node datasets, respectively.

We have described models trained with the weak supervisory signal coming from the MIL assumption. These models rely on a representation that is rich enough to obtain high slide classification accuracy on a held-out test set. The representation learned can be inspected by visualizing a projection of the feature space in two dimensions using dimensionality reduction techniques, such as t-distributed stochastic neighbor embedding (t-SNE). Hundred tiles were sampled from each test slide of the prostate dataset, in addition to its top-ranked tile, and extracted the final feature embedding before the classification layer.

Figure 21:
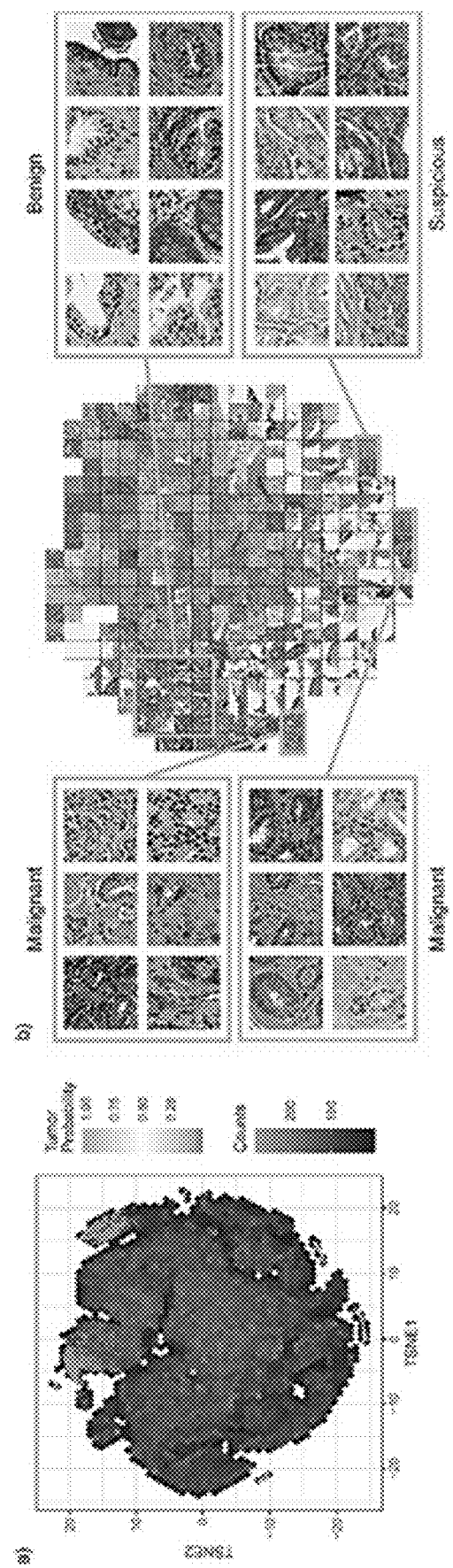
FIG. 21 depicts a representation visualization to classify tiles.

Referring to FIG. 21, shown are the results of the ResNet34 model trained on prostate at 20×. As depicted, a) A ResNet34 model trained at 20× was used to obtain the feature embedding before the final classification layer for a random set of tiles in the test set (n=182,912). The embedding was reduced to two dimensions (2D) with t-SNE and plotted using a hexagonal heat-map. Top-ranked tiles coming from negative and positive slides are represented by points colored by their tumor probability. b) Tiles corresponding to points in the 2D t-SNE space were randomly sampled from different regions. Abnormal glands are clustered together on the bottom and left sides of the plot. A region of tiles with tumor probability around 0:5 contains glands with features suspicious for prostatic carcinoma. Normal glands are clustered on the top left region of the plot. The model trained with MIL supervision was able to extract features that embed visually and semantically related tiles close to each other. A large region of different stroma tiles at the center of the plot was observed, extending towards the top right corner. The top left corner is where benign-looking glands are represented. The bottom portion contains background and edge tiles. The discriminative tiles with high tumor probability are clustered in two regions at the bottom and left of the plot. A closer look reveals the presence of malignant glands. Interestingly, a subset of the top-ranked tiles with tumor probability close to 0.5, indicating uncertainty, are tiles that contain glands suspicious of being malignant. Similar plots for the BCC and axillary lymph nodes models are reported in FIG. 27.

Slide Aggregation

The max-pooling operation that leads to the slide prediction under the MTh assumption is not robust. A single spurious misclassification can change the slide prediction, possibly resulting in a large number of false positives. One way to mitigate this type of mistake is to learn a slide aggregation model on top of the MIL classification results. For example, one approach learned a logistic regression based on the number of tiles per class as predicted by an ensemble of tile classifiers. Similarly, another approach extracted geometrical features from the tumor probability heat-map generated by a tile-level classifier, and trained a random forest model winning the CAMELYON16 challenge. In addition to the counts of tiles in each class, numerous other features were extracted from the heat-map generated by the MIL-based tile classifier. A random forest model is then trained on the set of engineered features. An in-depth description is found in the Methods section. This approach was analyzed on the prostate dataset, and also the model was utilized on the CAMELYON16 experiments that will be discussed later. For prostate cancer classification, the random forest trained on the validation split at 20× magnification produced a 0.98 AUC on the test set, no better than MIL alone (see FIG. 28). Although this procedure decreased drastically the false positive rate, and at 20× achieved a better balanced error than the basic max-pooling aggregation, this comes with an unacceptable increase of the false negative rate.

By just using the prediction of the classifier to generate the tumor probability heat-map, most of the information contained in the tile representation learned during the MTh training were discarded. Instead, given a vector representation of tiles, even if singularly they were not classified as positive by the tile classifier, taken together they could be suspicious enough to trigger a positive response by a representation-based slide-level classifier. Based on these ideas, an RNN-based model that can integrate information at the representation level to emit a final slide classification was introduced (as depicted in FIG. 19(*b*)). One important aspect is that the information can also be integrated across the various magnifications to produce a multi-scale classification. 128 dimensional vectors were used for the state representation of the recurrent unit, 10 recurrent steps (S=10), and weighted the positive class to give more importance to the sensitivity of the model.

Figure 22:
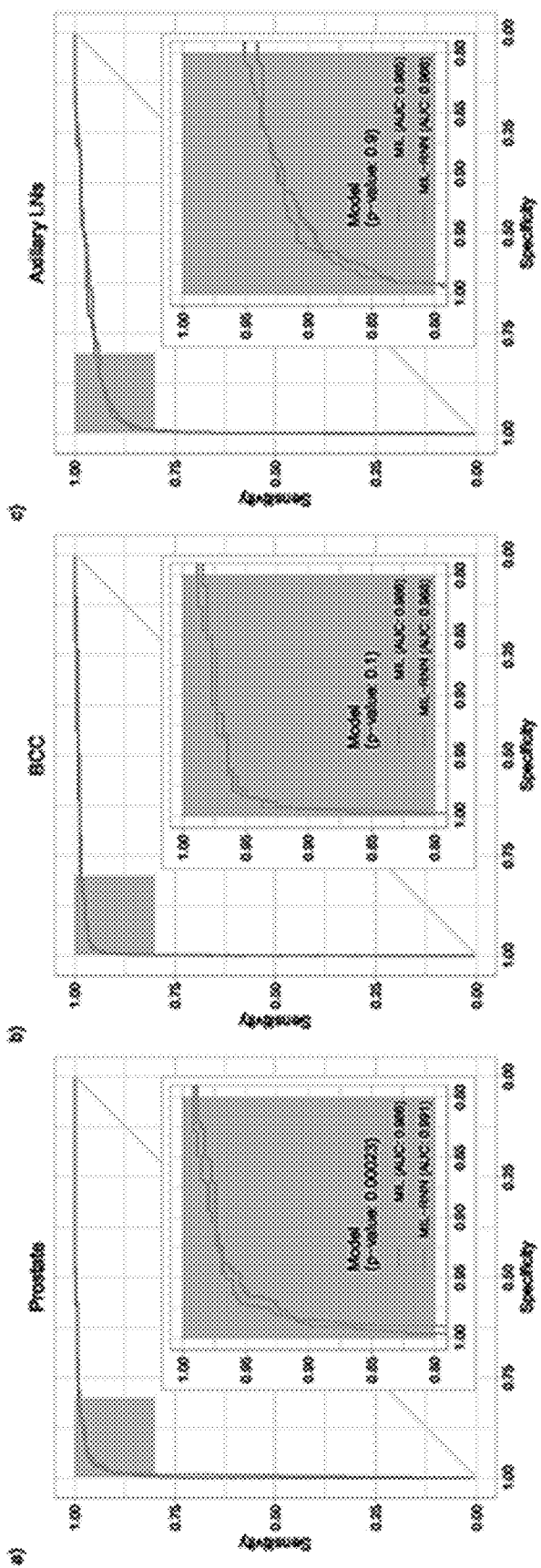
FIG. 22 depicts line graphs showing performance of various classification tasks.

Referring now to FIG. 22, shown are line graphs of MIL-RNN model performance for different classification tasks. Performance of the models trained at 20× magnification on the respective test datasets was measured in terms of AUC for each tumor type. a) For prostate cancer the MIL-RNN model significantly ($p \ll 0.001$) outperformed the model trained with MIL alone resulting in an AUC of 0:991. b) The BCC model (n=1,575) performed at 0.989, while c) breast metastases detection (n=1,473) achieved an AUC of 0.965. For these latter datasets adding an RNN did not significantly improve performance. Statistical significance was assessed using DeLong's test for two correlated receiver operating characteristic (ROC) curves. At 20×, the MIL-RNN models resulted in 0.991, 0.989 and 0.965 AUCs for prostate, BCC and breast metastases datasets, respectively. For the prostate experiment, the MIL-RNN method was significantly better than max-pooling aggregation. The multi-scale approach was tested on the prostate data, but its performance was not better than the one achieved by the single-scale model trained at 20×.

Error Analysis

Figure 23:
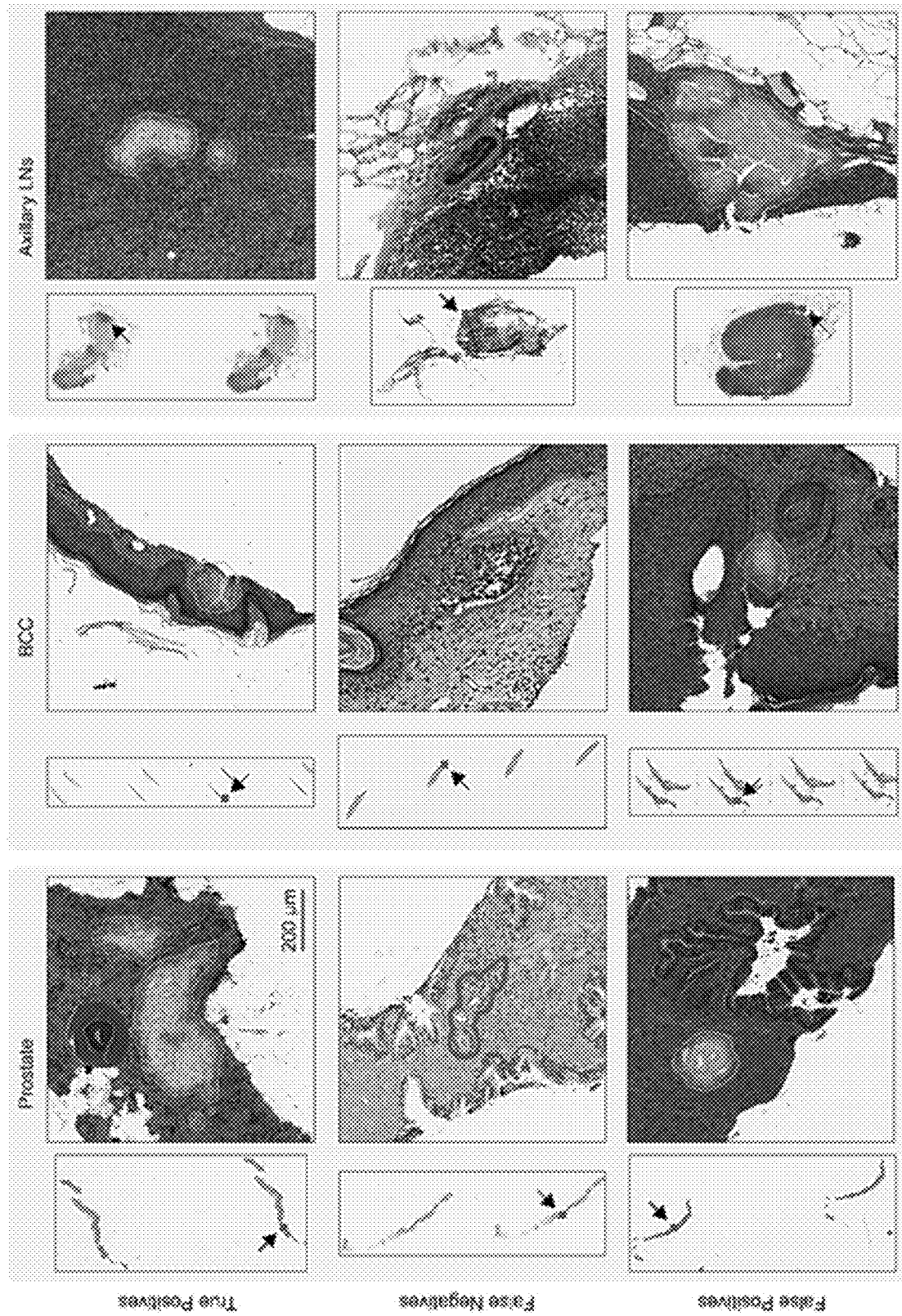
FIG. 23 depicts examples of classification results using the model.

Pathologists specialized in each discipline analyzed the errors made by MIL-RNN models trained at 20× magnification (a selection of cases is depicted). Referring now to FIG. 23, shown are examples of classification results. Examples of true positive (TP), false negative (FN) and false positive (FP) classifications are shown for each tumor type. The MIL-RNN model trained at 20× magnification was run with a step size of 20 pixels across a region of interest, generating a tumor probability heat-map. On every slide, the blue square represents the enlarged area. Prostate: TP: difficult diagnosis due to tumor found next to atrophy and inflammation; FN: very low tumor volume; and FP: model identified atypical small acinar proliferation (ASAP) showing a small focus of glands with atypical epithelial cells. BCC: TP: low tumor volume case; FN: low tumor volume case; and FP: the tongue of the epithelium abutting from the base of the epidermis shows an architecture similar to BCC. Axillary lymph nodes: TP: ITCs with neoadjuvant chemotherapy modifications; FN: slightly blurred cluster of ITCs missed due to very low volume; and FP: displaced epithelium/benign papillary inclusion.

Several cases (six in prostate, eight in BCC and 23 in axillary lymph nodes) in which the ground truth was mistaken were found in the test sets (Table 2), demonstrating that the method is robust to some level of noise in the ground truth of the datasets. Because the ground truth is reliant on the diagnosis reported in the LIS, the observed noise can be due to several factors: i) under the current WSI scanning protocol, as only select slides are scanned in each case, there exists the possibility of a mismatch between the slide scanned and the reported LIS diagnosis linked to each case; ii) a deeper slide level with no carcinoma present could be selected for scanning; and iii) tissue was removed to create tissue microarrays before slide scanning.

For the prostate model, a sub-specialized genitourinary pathologist (V.R.) reviewed the cases. Three of the 12 false negatives were correctly predicted as negative by the algorithm. Three other slides showed atypical morphological features but they were not sufficient to diagnose carcinoma. The confirmed six false negatives were characterized by having very low tumor volume. Taking into account the corrections to the ground truth, the AUC for the prostate test set improved from 0.991 to 0.994. The 72 false positives were reviewed as well. The algorithm falsely identified small foci of glands as cancer, focusing on small glands with hyperchromatic nuclei that contained at least a few cells with prominent nucleoli. Many of the flagged glands also showed intraluminal secretions. Overall the algorithm was justified in reporting the majority of these cases as suspicious, thus fulfilling the requisites of a screening tool.

For the BCC model, a dermatopathologist reviewed the cases. On the test set, four false negatives were corrected to true negatives, and four false positives were corrected to true positives. Given these corrections, the AUC improved from 0.988 to 0.994. The 12 cases determined to be false negatives were characterized by low tumor volume. The 15 false positives included squamous cell carcinomas and miscellaneous benign neoplastic and non-neoplastic skin lesions.

For the breast metastasis model, two sub-specialized breast pathologists (E.B. and M.G.H.) reviewed the cases. Seventeen of the initially classified false negatives were correctly classified as negatives, while four slides contained suspicious morphology that would likely require follow-up tests. A total of 21 false negatives were corrected to true negatives. In addition, two false positives were corrected to true positives. False negative to true negative corrections were due to tissue of interest not being present on a deeper H&E slide or sampling error at the time the frozen section was prepared; false positive to true positive corrections were due to soft tissue metastatic deposits or tumor emboli. The AUC improved from 0.965 to 0.989 given these corrections. Of the 23 false negatives, eight were macro-metastasis, 13 were micro-metastasis and two were ITCs. Of note, 12 cases (four false negatives and eight false positives) showed signs of treatment effect from neoadjuvant chemotherapy.

cious" categories for prostate and breast lesions respectively. The "other" category consisted of skin biopsies which contained tumors other than BCC. It is observed that some of the misclassifications stem from wrong ground-truth labels.

Generalization Experiments

Several sources of variability come into play in computational pathology. In addition to all the morphological variability, technical variability is introduced during glass slide preparation and scanning. How this variability can affect the prediction of an assistive model is a question that must be investigated thoroughly.

Assessing the performance of models on slides digitized on different scanners is crucial for enabling the application of the same model in smaller clinics that operate scanners from different vendors and do not have the infrastructure to train or fine-tune a model tailored to their needs. To test the effect of the scanner type on model performance, a substantial subset (1,274 out of 1,784) of the in-house prostate slides were scanned with a Philips Intelli Site Ultra-Fast Scanner for primary diagnostic use.

Figure 27:
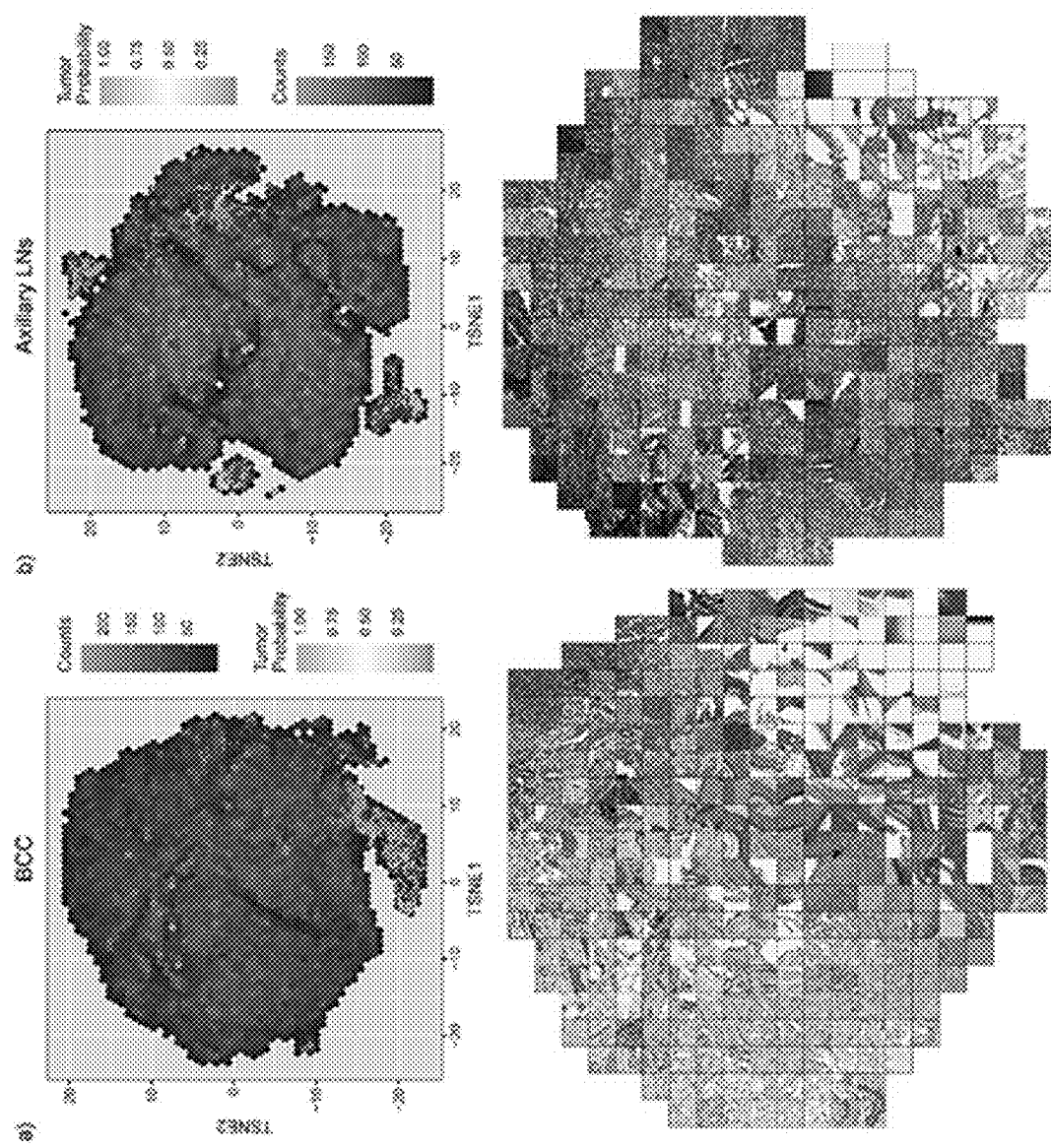
FIG. 27 depicts t-Distributed Stochastic Neighbor Embedding (t-SNE) visualization of node models.

Referring now to FIG. 27, depicted are generalization of performance results. The generalization performance of the proposed prostate and breast models were evaluated on different external test sets. a) Prostate model trained with MIL on MSK in-house slides tested on (i) the in-house test set (n=1,784) digitized on Aperio scanners, (ii) in-house test set digitized on a Philips scanner (n=1,274) and (iii) external slides submitted to MSK for consultation (n=12,727). Performance in terms of AUC decreased by 3% and 6% for the Philips scanner and external slides respectively. b) Comparison of the proposed MIL approach to state-of-the-art fully supervised learning for breast metastasis detection in lymph nodes. Left panel: the model was trained on MSK data with the proposed method (MIL+RNN) and tested on the MSK breast data test set (n=1,473) and on the test set of the CAMELYON16 challenge (n=129) showing a decrease in AUC of 7%. Right panel: A fully supervised model was trained on CAMELYON16 training data. While the resulting model would have won the CAMELYON16 challenge (n=129) its performance drops by over 20% when tested on a larger test set representing real-world clinical cases (n=1, 473). It is observed a decrease in performance in terms of AUC of 3% points. Analyzing the mismatches between the predictions on Aperio slides and their matching Philips slides, revealed a perceived difference in brightness, contrast and sharpness that could affect the prediction performance. In practice, an effective solution to reduce the generalization error even further could be training on a mixed dataset, or fine-tuning the model on data from the new scanner.

TABLE 2

|  | Prostate | | BCC | | Axillary LNs | |
| --- | --- | --- | --- | --- | --- | --- |
|  | FN | FP | FN | FP | FN | FP |
| Benign/Negative | 3 | 56 | 3 | 2 | 17 | 1 |
| Atypical/Other/Suspicious | 3 | 16 | 1 | 11 | 4 | 31 |
| Carcinoma/Positive | 6 | 0 | 12 | 4 | 23 | 2 |
| True Error Rate | 6/345 | 72/1,439 | 12/255 | 13/1,320 | 23/403 | 32/1,070 |

Error analysis on the test sets. Sub-specialty pathologists analyzed the slides that were misclassified by the MIL-RNN models. While slides can either be positive or negative for a specific tumor, sometimes it is not possible to diagnose a single slide with certainty based on morphology alone. These cases were grouped into the "atypical" and "suspi- To measure the effects of slide preparation on model performance, a very large set included over 12,000 prostate consultation slides submitted to MSK from other institutions in the US and other 44 countries were gathered. It should be noted that these slides are typically diagnostically challenging and are the basis for the requested expert pathologist review. The MIL-RNN model trained at 20× was applied to the large submitted slides dataset and observed a drop of about 6% points in terms of AUC (as seen on FIG. 24(a)). Importantly, the decrease in performance was mostly seen in the specificity to the new test set while sensitivity remained high.

To substantiate the claim that models trained under full supervision on small, curated datasets do not translate well to clinical practice, several experiments were performed with the CAMELYON16 database, which includes pixel-wise annotations for 270 training slides and is one of the largest annotated, public digital pathology datasets available. A model for automatic detection of metastatic breast cancer on the CAMELYON16 dataset was implemented, modeled after, the winning team of the CAMELYON16 challenge. The approach can be considered state-of-the-art for this task and relies on fully supervised learning and pixel-level expert annotations. The main differences are the architecture use, their usage of hard negative mining, and the features extracted to train the slide-level random forest classifier. A more detailed description can be found in the Methods section. One implementation achieved an AUC of 0.930 on the CAMELYON16 test set. This model would have won the classification portion of the CAMELYON16 challenge and would be ranked fifth of the open leaderboard. The same model, trained under full supervision on CAMELYON16, was applied to the MSK test set of the axillary lymph nodes dataset and resulted in an AUC of 0.727, constituting a 20% drop compared to its performance on the CAMELYON16 test set (as seen on FIG. 24(b), right panel). The reverse experiment, done by training the MIL model on the MSK axillary lymph node data and testing it on the CAMELYON16 test data, produced an AUC of 0.899, representing a much smaller drop in performance when compared to the 0.965 on the MSK test set (as seen on FIG. 24(b), left panel).

These results illustrate that current deep-learning models, trained on small datasets, even with the advantage of exhaustive, pixel-wise labels, are not able to generalize to clinical-grade real-world data. It is hypothesized that small, well curated datasets are not sufficient to capture the vast biological and morphological variability of cancer as well as the technical variability introduced by the staining and preparation processes in histopathology. The observations urge caution and in-depth evaluation on real-world datasets before applying deep learning models for decision support in clinical practice. These results also demonstrate that weakly supervised approaches like the one proposed here show a clear advantage over conventional fully supervised learning in that they enable training on massive, diverse datasets without the necessity for data curation.

4. Discussion

The main hypothesis addressed in this work is that clinical-grade performance can be reached without annotating whole slide images at pixel level. More rigorously, most literature refers to clinical-grade in terms of comparison with a human performing the same task, usually under some time or other constraints. It is suggested that these comparisons are artificial and offer little insight in how to use such systems in clinical practice. This disclosure proposes a different approach to measure clinical-grade performance. In clinical practice, a case, especially if challenging, is reviewed by multiple pathologists with the help of immunohistochemistry and molecular information in addition to H&E morphology. Based on this companion information, one can assume that a team of pathologists at a comprehensive cancer center will, in the clinical setting, operate with 100% sensitivity and specificity. Under these assumptions, clinical-grade for a decision support system does not mean surpassing the performance of pathologists, which is impossible, but achieving 100% sensitivity with an acceptable false positive rate. This formulation lends itself to a clinical application as described below.

To test the hypothesis, a deep-learning framework was developed that combines convolutional neural networks with RNNs under a MIL paradigm. A large dataset comprising 44,732 slides from 15,187 patients was compiled across three different cancer types, a scale unprecedented in computational pathology. A state-of-the-art computer cluster for the feasibility of the project was built. Extensive validation experiments confirmed the hypothesis and demonstrated that clinical-grade decision support is feasible.

The implications of these results are wide ranging: (i) The fact that manual pixel-level annotation is not necessary allows for the compilation of datasets that are magnitudes larger than in previous studies. (ii) This, in turn, allows the algorithm to learn from the full breadth of slides presented to clinicians from real-life clinical practice, representing the full wealth of biological and technical variability. (iii) As a result, no data curation is necessary because the model can learn that artifacts are not important for the classification task. (iv) The previous two points allow the model trained with the proposed method to generalize better to real data that would be observed in pathology practice. In addition to generalization to test sets for each cancer type, generalization to a dataset of slides scanned on the Philips scanner is shown, as well as a dataset of slides from 6,323 patients from institutions all over the world. (v) The generalization performance is clinically relevant with AUCs greater than 0.98 for all cancer types tested. (vi) the present disclosure proposes a strategy to integrate this system in the clinical work-flow. With the advent of digital imaging becoming a potential new standard of care, predictive models can be presented as either a screening tool or a computer assisted diagnosis (CAD) system. At a fully operational digital pathology department, the predictive model is run on each scanned slide. The algorithm sorts cases, and slides within each case, based on the predicted tumor probability as soon as they are available from the pathology laboratory.

Figure 25:
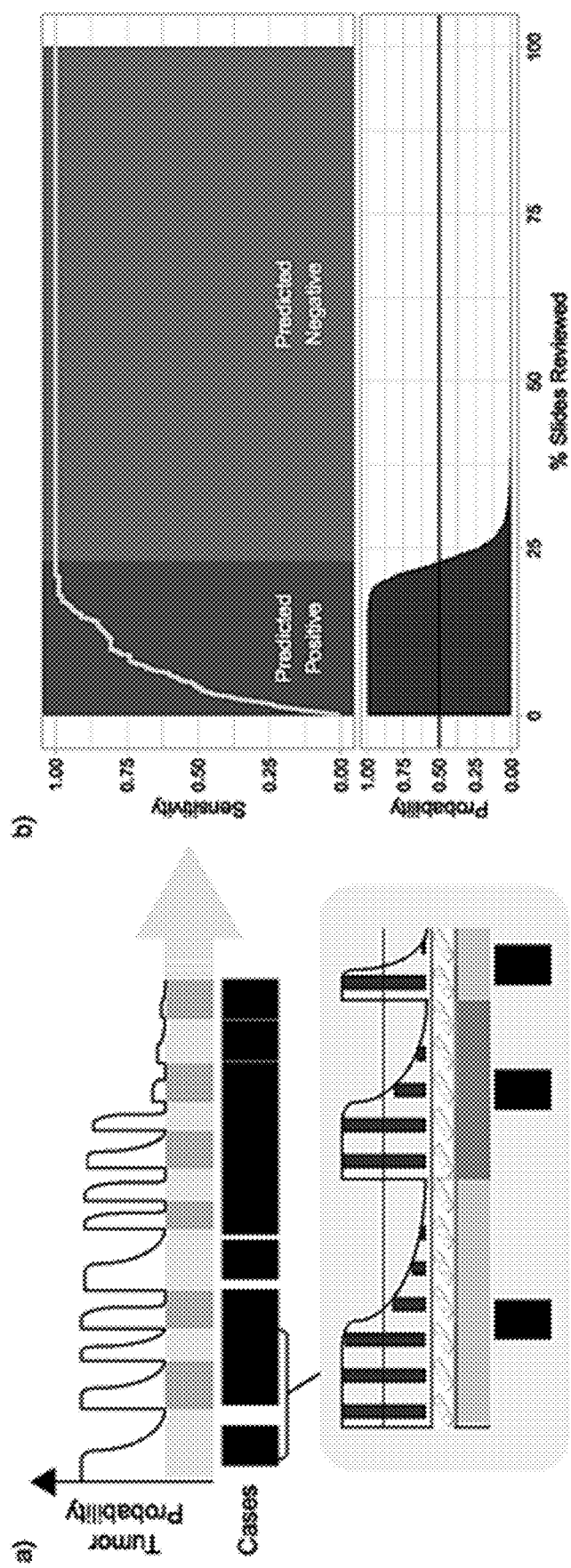
FIG. 25 depicts graphs of decision-support in clinical practice using the model.

During diagnostic reporting, the pathologist is presented with the model's recommendations through an interface that would flag positive slides for rapid review in a screening scenario, or to disregard all benign slides in a diagnostic scenario. Referring now to FIG. 25, depicted is decision-support in clinical practice. a) By ordering the cases, and slides within each case based on their tumor probability, pathologist can focus their attention on slides that are likely positive for cancer. b) Following the algorithm's prediction would allow pathologist to potentially ignore more than 75% of the slides while retaining 100% sensitivity for prostate cancer at the case level (n=1,784). In this latter case, as depicted, it is seen (cf. FIG. 30 below for BCC and breast metastases) that the prostate model would allow the removal of more than 75% of the slides from the workload of a pathologist without any loss in sensitivity at the patient level.

5. Methods

Hardware and Software

We ran all experiments on MSK's high performance computing (HPC) cluster. In particular, seven NVIDIA DGX-1 compute nodes, each containing eight V100 Volta GPUs and 8 TB SSD local storage were used. OpenSlide was used to access the WSI files on the fly and PyTorch for data loading, building models, and training. The final statistical analysis was performed in R using ggplot2 for generating plots and pROC to compute ROC curves, AUCs (and their confidence intervals using bootstrapping), and test statistical significance of two ROC curves (using DeLong's test for two correlated ROC curves).

Slide Diagnosis Retrieval

Pathology reports are recorded in the laboratory information system (LIS) of the pathology department. For the prostate and axillary lymph-nodes datasets, the ground-truth labels (i.e. the slide-level diagnoses) are retrieved directly by querying the LIS database. This is made possible by the structured nature of the reporting done for these sub-specialties. In dermatopathology, basal cell carcinomas are not reported in structured form. To overcome this problem, a trained dermatopathologist (A.M.) checked the free text diagnoses and assigned final binary labels to each case manually.

Dataset Curation

The datasets were not curated to test the applicability of the proposed system in a real-world, clinical scenario. Across all datasets, less than 10 slides were removed due to excessive pen markings.

MIL-Based Slide Diagnosis

Classification of a whole digital slide (e.g. WSI) based on a tile-level classifier can be formalized under the classic MIL paradigm when only the slide-level class is known and the classes of each tile in the slide are unknown. Each slide $s_i$ from the slide pool $S=\{s_i: i=1, 2, \ldots, n\}$ can be considered a bag consisting of a multitude of instances (we used tiles of size 224×224 pixels). For positive bags, there must exist at least one instance that is classified as positive by some classifier. For negative bags, instead, all instances must be classified as negative. Given a bag, all instances are exhaustively classified and ranked according to their probability of being positive. If the bag is positive, the top-ranked instance should have a probability of being positive that approaches 1; if it is negative, its probability of being positive should approach 0. Solving the MIL task induces the learning of a tile-level representation that can linearly separate the discriminative tiles in positive slides from all other tiles. This representation will be used as input to a RNN. The complete pipeline for the MIL classification comprises the following steps: (i) tiling of each slide in the dataset; for each epoch, which consists of an entire pass through the training data, (ii) a complete inference pass through all the data; (iii) intra-slide ranking of instances; (iv) model learning based on the top-ranked instance for each slide.

Slide Tiling

Figure 31:
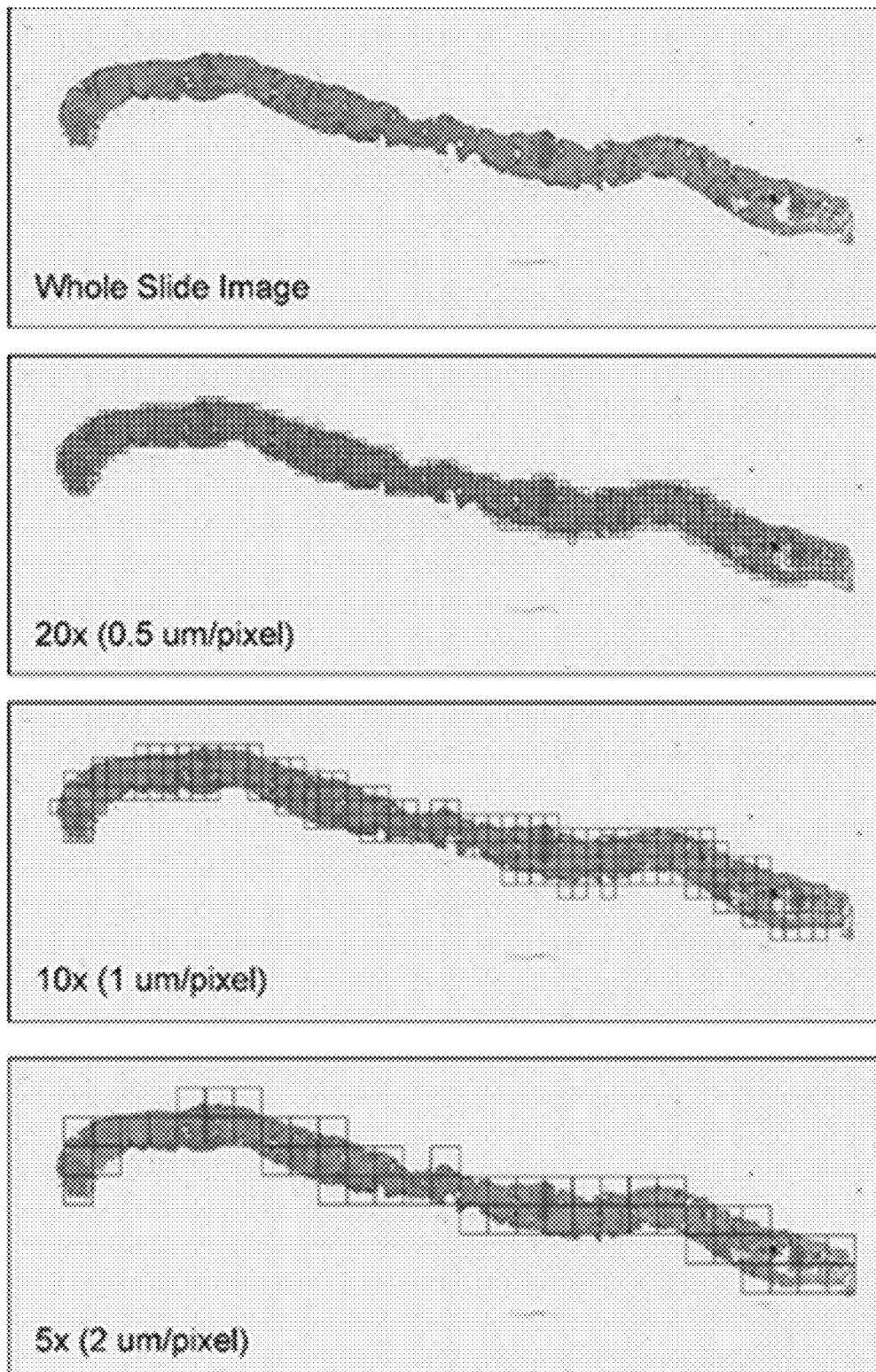
FIG. 31 depicts example slide tiled grid with no overlap.

The instances were generated by tiling each slide on a grid. Referring to FIG. 31, depicted is an example of a slide tiled on a grid with no overlap at different magnifications. A slide represents a bag, and the tiles constitute the instances in that bag. In this work, instances at different magnifications are not part of the same bag. Otsu's method is used to threshold the slide thumbnail image to efficiently discard all background tiles, thus, drastically reducing the amount of computation per slide. Tiling can be performed at different magnification levels and with various levels of overlap between adjacent tiles. Three magnification levels (5×, 10× and 20×) were investigated. The amount of overlap used was different at each magnification during training and validation: no overlap at 20×, 50% overlap at 10× and 67% overlap at 5×. For testing, 80% overlap was used at every magnification. Given a tiling strategy, the bags were defined as $B=\{B_{si}: i=1, 2, \ldots, n\}$ where $B_{si}=\{b_{i,1}, b_{i,2}, \ldots, b_{i,mi}\}$ is the bag for slide $s_i$ containing $m_i$ total tiles.

Model Training

The model is a function $f_\theta$ with current parameters $\theta$ that maps input tiles $b_{i,j}$ to class probabilities for "negative" and "positive" classes. Given the bags B, a list of vectors $O=\{\overline{o_i}: i=1, 2, \ldots, n\}$ one for each slide $s_i$ containing the probabilities of class "positive" for each tile $b_{i,j}$: $j=1, 2, \ldots, m$ in $B_{si}$ was obtained. The index $k_i$ of the tile within each slide, which shows the highest probability of being "positive" $k_i=\mathrm{argmax}(\overline{o_i})$, was obtained. This is the most stringent version of MIL, but the standard MIL assumption can be relaxed by introducing hyper-parameter K and assume that at least K tiles exist in positive slides that are discriminative. For K=1, the highest ranking tile in bag $B_{si}$ is then $b_{i,k}$. The output of the network $\tilde{y}_i=f_\theta(b_{i,k})$ can then be compared to $y_i$, the target of slide $s_i$, through the cross-entropy loss l as in Equation 1. Similarly, if K>1, all selected tiles from a slide share the same target $y_i$ and the loss can be computed with Equation 1 for each one of the K tiles.

$$l=-w1[yi \log(\tilde{y}i)]-w0[(1-yi) \log(1-\tilde{y}i)] \quad (1)$$

Given the unbalanced frequency of classes, weights $w_0$ and $w_1$, for negative and positive classes, respectively, can be used to give more importance to the underrepresented examples. The final loss is the weighted average of the losses over a mini-batch. Minimization of the loss is achieved via stochastic gradient descent (SGD) using the Adam optimizer and learning rate 0.0001. Mini-batches of size 512 for AlexNet, 256 for resnets and 128 for VGGs and DenseNet201 were used. All models were initialized with ImageNet pre-trained weights. Early stopping was used to avoid over-fitting.

Model Testing

At validation/test time, all the tiles for each slide are fed through the network. Given a threshold (usually 0.5), if at least one tile is positive, then the entire slide is called positive; if all the instances are negative, then the slide is negative. In addition, it is assumed that the probability of a slide being positive to be the highest probability among all the tiles in that slide. This max-pooling over the tile probability is the easiest aggregation technique. Different aggregation techniques are explored below.

Naïve Multi-Scale Aggregation

Given models $f_{20x}$, $f_{10x}$, $f_{5x}$ trained at 20×, 10× and 5× magnifications, a multi-scale ensemble can be created by pooling the predictions of each model with an operator. Average and max-pooling was used to obtain naive multi-scale models.

Random Forest-Based Slide Integration

Given a model $f$ trained at a particular resolution, and a WSI, a heat-map of tumor probability can be obtained over the slide. Several features can then be extracted from the heat-map to train a slide aggregation model. For example, one approach used the count of tiles in each class to train a logistic regression model. Here, that approach was extended by adding several global and local features and train a random forest to emit a slide diagnosis. The features extracted are: 1) total count of tiles with probability >=0.5; 2-11) 10-bin histogram of tile probability; 22-30) count of connected components for a probability threshold of 0.1 of size in ranges 1-10, 11-15, 16-20, 21-25, 26-30, 31-40, 41-50, 51-60, 61-70 and >70 respectively; 31-40) 10-bin local histogram with window size 3×3 aggregated by max-pooling; 41-50) 10-bin local histogram with window size 3×3 aggregated by averaging; 51-60) 10-bin local histogram with window size 5×5 aggregated by max-pooling; 61-70) 10-bin local histogram with window size 5×5 aggregated by averaging; 71-80) 10-bin local histogram with window size 7×7 aggregated by max-pooling; 81-90) 10-bin local histogram with window size 7×7 aggregated by averaging; 91-100) 10-bin local histogram with window size 9×9 aggregated by max-pooling; 101-110) 10-bin local histogram with window size 9×9 aggregated by averaging; 111-120) 10-bin histogram of all tissue edge tiles; 121-130) 10-bin local histogram of edges with linear window of size 3×3 aggregated by max-pooling; 131-140) 10-bin local histogram of edges with linear window of size 3×3 aggregated by averaging; 141-150) 10-bin local histogram of edges with linear window of size 5×5 aggregated by max-pooling; 151-160) 10-bin local histogram of edges with linear window of size 5×5 aggregated by averaging; 161-170) 10-bin local histogram of edges with linear window of size 7×7 aggregated by max-pooling; 171-180) 10-bin local histogram of edges with linear window of size 7×7 aggregated by averaging. The random forest was learned of the validation set instead of the training set to avoid over-fitting.

RAIN-Based Slide Integration

Model $f$ mapping a tile to class probability consists of two parts: a feature extractor $f_F$ that transforms the pixel space to representation space and a linear classifier $f_C$ that projects the representation variables into the class probabilities. The output of $f_F$ for the ResNet34 architecture is a 512-dimensional vector representation. Given a slide and model $f$, a list of the S most interesting tiles within the slide in terms of positive class probability can be obtained. The ordered sequence of vector representations $e=e_1, e_2, \ldots, e_S$ is the input to a RNN along with a state vector h. The state vector is initialized with a zero vector. Then for step $i=1, 2, \ldots,$ S of the recurrent forward pass, the new state vector $h_i$ is given by Equation 2:

$$hi = ReLU(We\,ei + Wh\,hi-1 + b) \quad (2)$$

where $W_e$ and $W_h$ are the weights of the RNN model. At step S, the slide classification is simply $o=W_o h_S$, where $W_o$ maps a state vector to class probabilities. With S=1 the model does not recur and the RNN should learn the $f_C$ classifier. This approach can be easily extended to integrate information at multiple scales. Given models $f_{20x}, f_{10x}, f_{5x}$ trained at 20×, 10× and 5× magnifications, the S most interesting tiles from a slide was obtained by averaging the prediction of the three models on tiles extracted at the same center pixel but at different magnifications. Now the inputs to the RNN at each step i are $e_{20x,i}, e_{10x,i}, e_{5x,i}$, and the state vector $h_{i-1}$. The new state vector is then given by Equation 3:

$$hi = ReLU(W20x\,e20x,i + W10x\,e10x,i + W5x\,e5x,i + Wh\,hi-1 + b) \quad (3)$$

All RNN models were trained with cross-entropy loss and SGD with a batch size of 256.

CAMELYON16 Experiments

The CAMELYON16 dataset consists of 400 total patients for whom a single WSI is provided as a tag image file format (TIFF). Annotations are given in extensible markup language (XML) format, one per each positive slide. For each annotation, several regions, defined by vertex coordinates, may be present. Since these slides were scanned at a higher resolution than the slides scanned at MSK, a tiling method was developed to extract tiles containing tissue from both inside and outside the annotated regions at MSK's 20× equivalent magnification (0.5 μm/pixel) to enable direct comparison with the datasets. The method generates a grid of possible tiles, excludes background via Otsu thresholding and determines whether a tile is inside an annotation region by solving a point in polygon problem.

We used 80% of the training data to train the model, and 0% were left for model selection. 1,000 tiles were extracted at random from each negative slide and 1,000 negative tiles and 1,000 positive tiles from the positive slides. A ResNet34 model was trained augmenting the dataset on-the-fly with 90 degree rotations, horizontal flips, and color jitter. The model was optimized with SGD. The best performing model on the validation set was selected. Slide-level predictions were generated with the random forest aggregation approach explained before and trained on the entire training portion of the CAMELYON16 dataset. To train the random forest model, exhaustively tiled with no overlap the training slides was obtained to generate the tumor probability maps. The trained random forest was then evaluated on the CAMELYON16 test dataset and on the large breast lymph node metastasis test datasets.

Referring now to FIG. 26, depicted is a MIL model classification performance for different cancer datasets. Performance on the respective test datasets was measured in terms of AUC. a) Best results were achieved on the prostate dataset (n=1,784), with an AUC of 0.989 at 20× magnification. b) For BCC (n=1,575), the model trained at 5× performed the best, with an AUC of 0.990. c) The worst performance came on the breast metastasis detection task (n=1,473), with an AUC of 0.965 at 20×. The axillary lymph node dataset is the smallest of the three datasets, which is in agreement with the hypothesis that larger datasets are necessary to achieve lower error rates on real-world clinical data.

Referring now to FIG. 27, shown is t-SNE visualization of the representation space for the BCC and axillary lymph node models. 2D t-SNE projection of the 512-dimensional representation space were generated for 100 randomly sampled tiles per slide. a) BCC representation (n=144,935). b) axillary lymph nodes representation (n=139,178).

Figure 28:
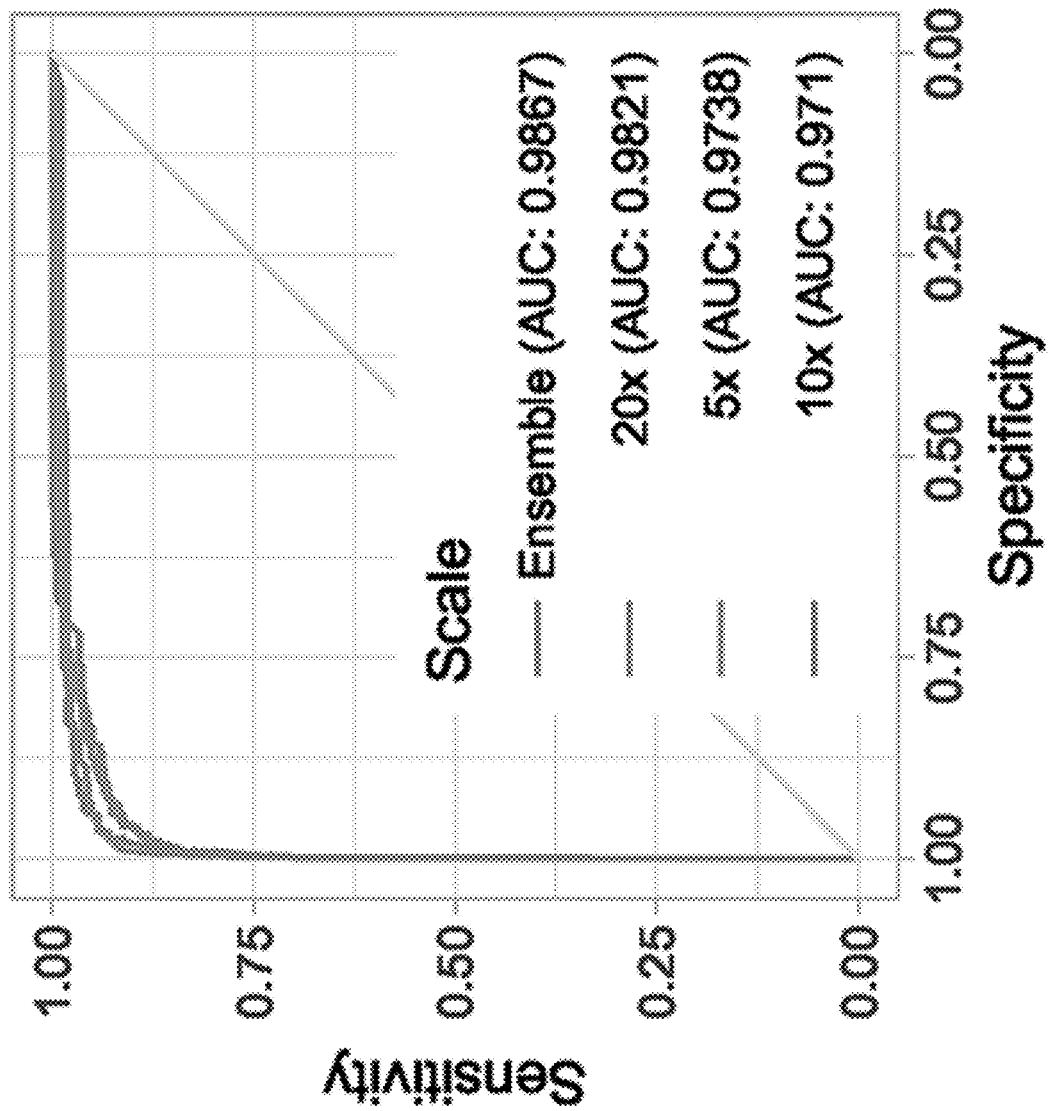
FIG. 28 depicts line graphs of performance of model at multiple scales.

Referring now to FIG. 28, shown is performance of the MIL-RF model at multiple scales on the prostate dataset. The MIL model was run on each slide of the test dataset with a stride of 40 pixels. From the resulting tumor probability heat-map, hand-engineered features were extracted for classification with the random forest (RF) model. The best MIL-RF model (ensemble model, AUC of 0.987) did not outperform the MTh-only model (20× model, AUC of 0.986, see FIG. 5).

Figure 29:
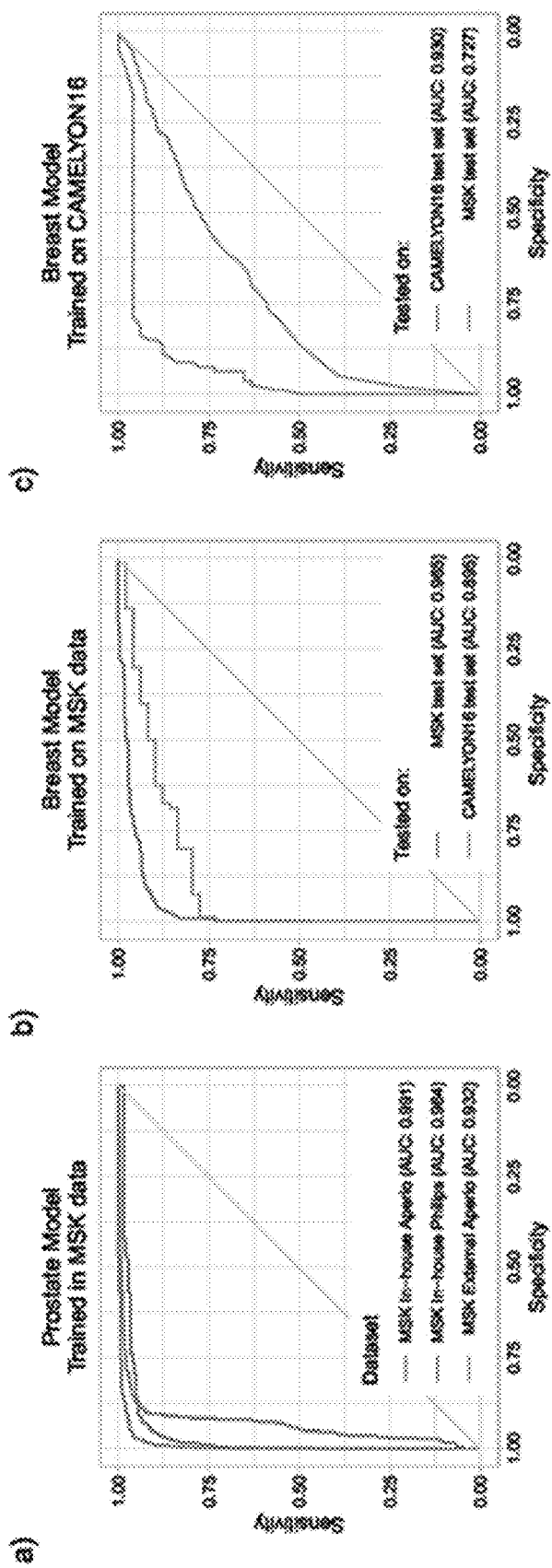
FIG. 29 depicts line graphs of receiver operating characteristic (ROC) curves of generalization experiments.

Referring now to FIG. 29, shown are ROC curves of the generalization experiments summarized in FIG. 7. a) Prostate model trained with MIL on MSK in-house slides tested on: (i) in-house slides test set (n=1,784) digitized on Aperio scanners, (ii) in-house slides test set digitized on a Philips scanner (n=1,274) and (iii) external slides submitted to MSK for consultation (n=12,727). b-c) Comparison of the proposed MIL approach to state-of-the-art fully supervised learning for breast metastasis detection in lymph nodes. b) The breast model trained on MSK data with the proposed method (MIL+RNN) and tested on the MSK breast data test set (n=1,473) and on the test set of the CAMELYON16 challenge (n=129), achieved AUCs of 0.965 and 0.895 respectively. c) The fully supervised model trained on CAMELYON16 data was tested on the CAMELYON16 test set (n=129) achieving 0.930 AUC. Its performance dropped to 0.727 AUC when tested on the MSK test set (n=1,473).

Figure 30:
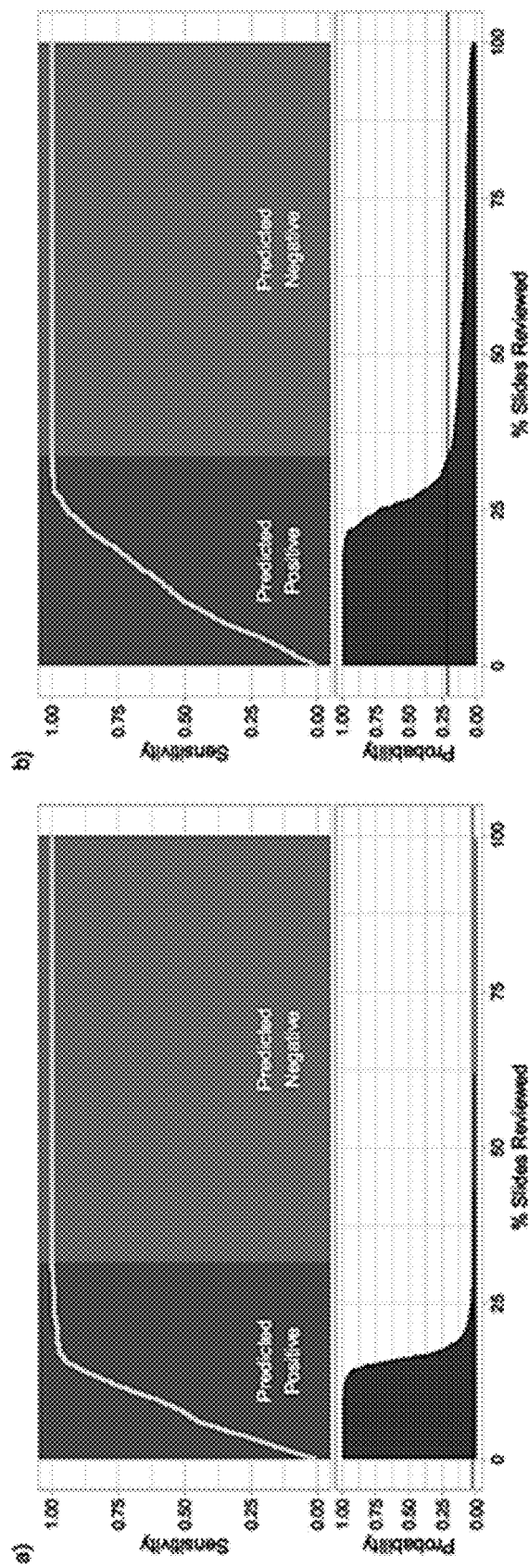
FIG. 30 depicts lien graphs of decision support with different models.

Referring now to FIG. 30, shown is decision support with the BCC and breast metastases models. For each dataset, slides are ordered by their probability of being positive for cancer as predicted by the respective MIL-RNN model. The sensitivity is computed at the case level. a) BCC (n=1,575): Given a positive prediction threshold of 0.025, it is possible to ignore roughly 68% of the slides while maintaining 100% sensitivity. b) Breast metastases (n=1,473): Given a positive prediction threshold of 0.21, it is possible to ignore roughly 65% of the slides while maintaining 100% sensitivity.

Referring now to FIG. 31, shown is example of a slide tiled on a grid with no overlap at different magnifications. A slide represents a bag, and the tiles constitute the instances in that bag. In this work, instances at different magnifications are not part of the same bag.

Stratified prediction performance of the prostate cancer MIL-RNN model. Relevant categories for positive slides are Gleason grades and tumor sizes and for negative slides they are the presence of atrophy or hyperplasia. The dataset was divided into in-house and external consultation cases. The in-house data was sub-divided into training, validation and test sets.

image classification system 3202 may include at least one feature classifier 3208, at least one model trainer 3210, at least one inference model 3212 (sometimes referred herein as an inference system), and at least one aggregation model 3214 (sometimes referred herein as an aggregation system), among others. The feature classifier 3208 may include at least one tile generator 3216 and at least one model applier 3218. The model trainer 3210 may include at least one error calculator 3220, at least one model corrector 3222, and at least one training database 3224. In some embodiments, the inference model 3212 and the aggregation model 3214 each may have a training mode and a runtime mode. Under the training mode, the image classification system 3202 may invoke both the feature classifier 3208 and the model trainer

TABLE S.1

| Source | Split | Metric | Total Slides | FNR | TPR | FPR | TNR |
|---|---|---|---|---|---|---|---|
| In-house | Train | Cancer | 1,712 | 0.0058 | 0.9942 | — | — |
| | | Grade 6 | 870 | 0.0092 | 0.9908 | — | — |
| | | Grade 7 | 662 | 0.0030 | 0.9970 | — | — |
| | | Grade 8 | 95 | 0.0000 | 1.0000 | — | — |
| | | Grade 9 | 83 | 0.0000 | 1.0000 | — | — |
| | | Grade 10 | 0 | — | — | — | — |
| | | Tumor Size: 0.1-1.2 | 401 | 0.0175 | 0.9825 | — | — |
| | | Tumor Size: 1.2-3.3 | 425 | 0.0047 | 0.9953 | — | — |
| | | Tumor Size: 3.3-6.5 | 434 | 0.0023 | 0.9977 | — | — |
| | | Tumor Size: 6.5-70 | 428 | 0.0000 | 1.0000 | — | — |
| | | Benign | 6,809 | — | — | 0.0117 | 0.9883 |
| | | Atrophy/Hyperplasia | 88 | — | — | 0.0114 | 0.9886 |
| | Validation | Cancer | 345 | 0.0087 | 0.9913 | — | — |
| | | Grade 6 | 202 | 0.0099 | 0.9901 | — | — |
| | | Grade 7 | 114 | 0.0088 | 0.9912 | — | — |
| | | Grade 8 | 17 | 0.0000 | 1.0000 | — | — |
| | | Grade 9 | 12 | 0.0000 | 1.0000 | — | — |
| | | Grade 10 | 0 | — | — | — | — |
| | | Tumor size: 0.1-1.2 | 97 | 0.0309 | 0.9691 | — | — |
| | | Tumor size: 1.2-3.3 | 75 | 0.0000 | 1.0000 | — | — |
| | | Tumor size: 3.3-6.5 | 83 | 0.0000 | 1.0000 | — | — |
| | | Tumor size: 6.5-70 | 88 | 0.0000 | 1.0000 | — | — |
| | | Benign | 1,482 | — | — | 0.0533 | 0.9467 |
| | | Atrophy/Hyperplasia | 28 | — | — | 0.0357 | 0.9643 |
| | Test | Cancer | 345 | 0.0174 | 0.9826 | — | — |
| | | Grade 6 | 169 | 0.0178 | 0.9822 | — | — |
| | | Grade 7 | 145 | 0.0138 | 0.9862 | — | — |
| | | Grade 8 | 19 | 0.0526 | 0.9474 | — | — |
| | | Grade 9 | 12 | 0.0000 | 1.0000 | — | — |
| | | Grade 10 | 0 | — | — | — | — |
| | | Tumor size: 0.1-1.2 | 83 | 0.0723 | 0.9277 | — | — |
| | | Tumor size: 1.2-3.3 | 92 | 0.0000 | 1.0000 | — | — |
| | | Tumor size: 3.3-6.5 | 79 | 0.0000 | 1.0000 | — | — |
| | | Tumor size: 6.5-70 | 87 | 0.0000 | 1.0000 | — | — |
| | | Benign | 1,439 | — | — | 0.0500 | 0.9500 |
| | | Atrophy/Hyperplasia | 31 | — | — | 0.0000 | 1.0000 |
| Consultations | | Cancer | 12,413 | 0.0411 | 0.9589 | — | — |
| | | Grade 6 | 3,432 | 0.0280 | 0.9720 | — | — |
| | | Grade 7 | 6,085 | 0.0251 | 0.9749 | — | — |
| | | Grade 8 | 1,333 | 0.0765 | 0.9235 | — | — |
| | | Grade 9 | 1,445 | 0.0381 | 0.9619 | — | — |
| | | Grade 10 | 18 | 0.2222 | 0.7778 | — | — |
| | | Tumor size: 0.1-1.2 | 3,345 | 0.0984 | 0.9016 | — | — |
| | | Tumor size: 1.2-3.3 | 3,103 | 0.0248 | 0.9752 | — | — |
| | | Tumor size: 3.3-6.5 | 2,939 | 0.0160 | 0.9840 | — | — |
| | | Tumor size: 6.5-70 | 2,992 | 0.0177 | 0.9823 | — | — |
| | | Benign | 314 | — | — | 0.1433 | 0.8567 |

Figure 32A:
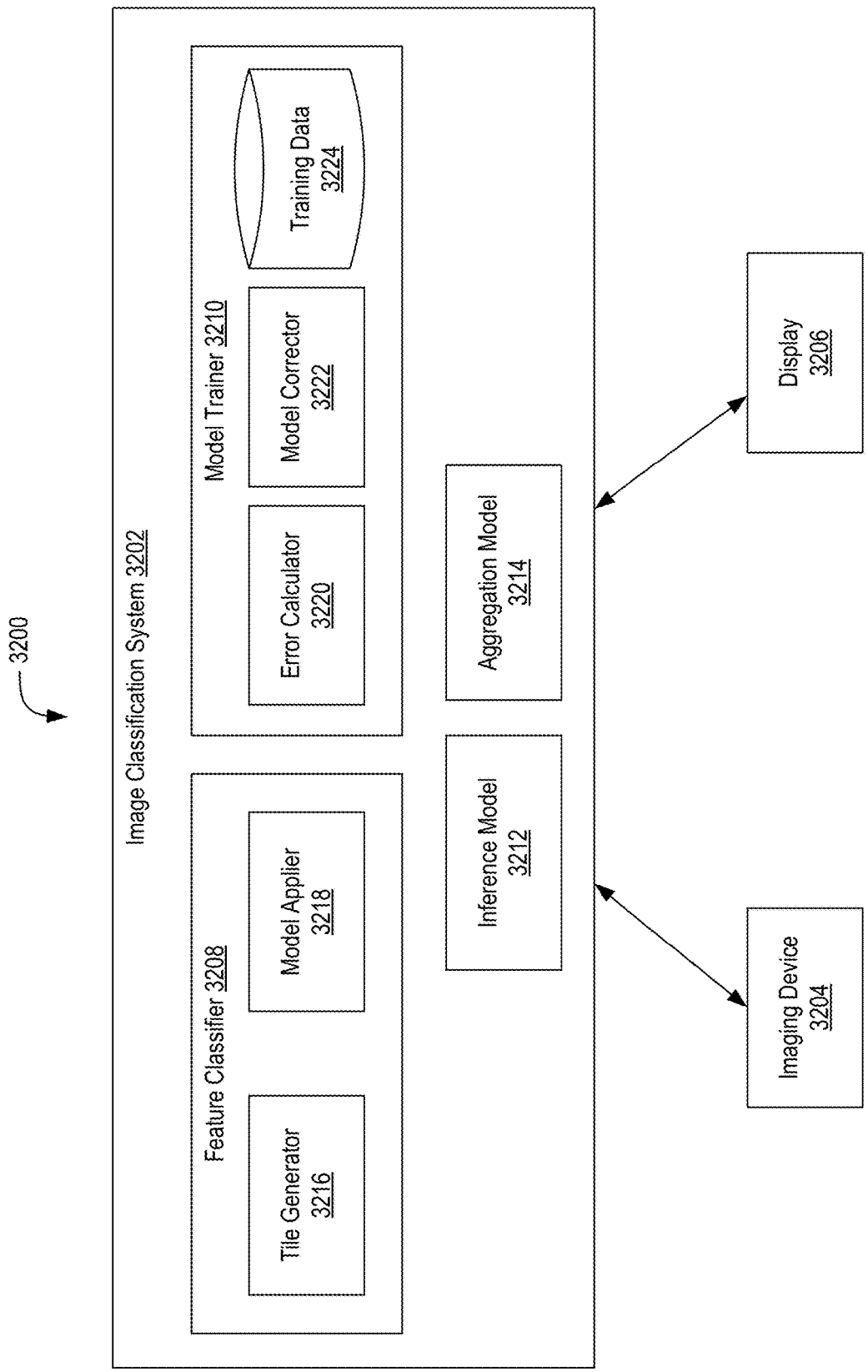
FIG. 32A depicts a block diagram of a system for classifying biomedical images and training models for classifying biomedical images using multiple-instance learning.

C. Systems and Methods for Multiple Instance Learning for Classification and Localization in Biomedical Imaging Referring now to FIG. 32A, depicted is a block diagram of a system 3200 for classifying biomedical images and training models for classifying biomedical images using multiple-instance learning. In brief overview, the system 3200 may include an image classification system 3202 (sometimes referred herein as an image classifier), at least one imaging device 2304, and at least one display 3206. The 3210. Each of the components of system 3200 may be implemented using hardware (e.g., processing circuitry and memory) or a combination of hardware and software as detailed here in Section D in conjunction with FIGS. 34A-D.

Figure 32B:
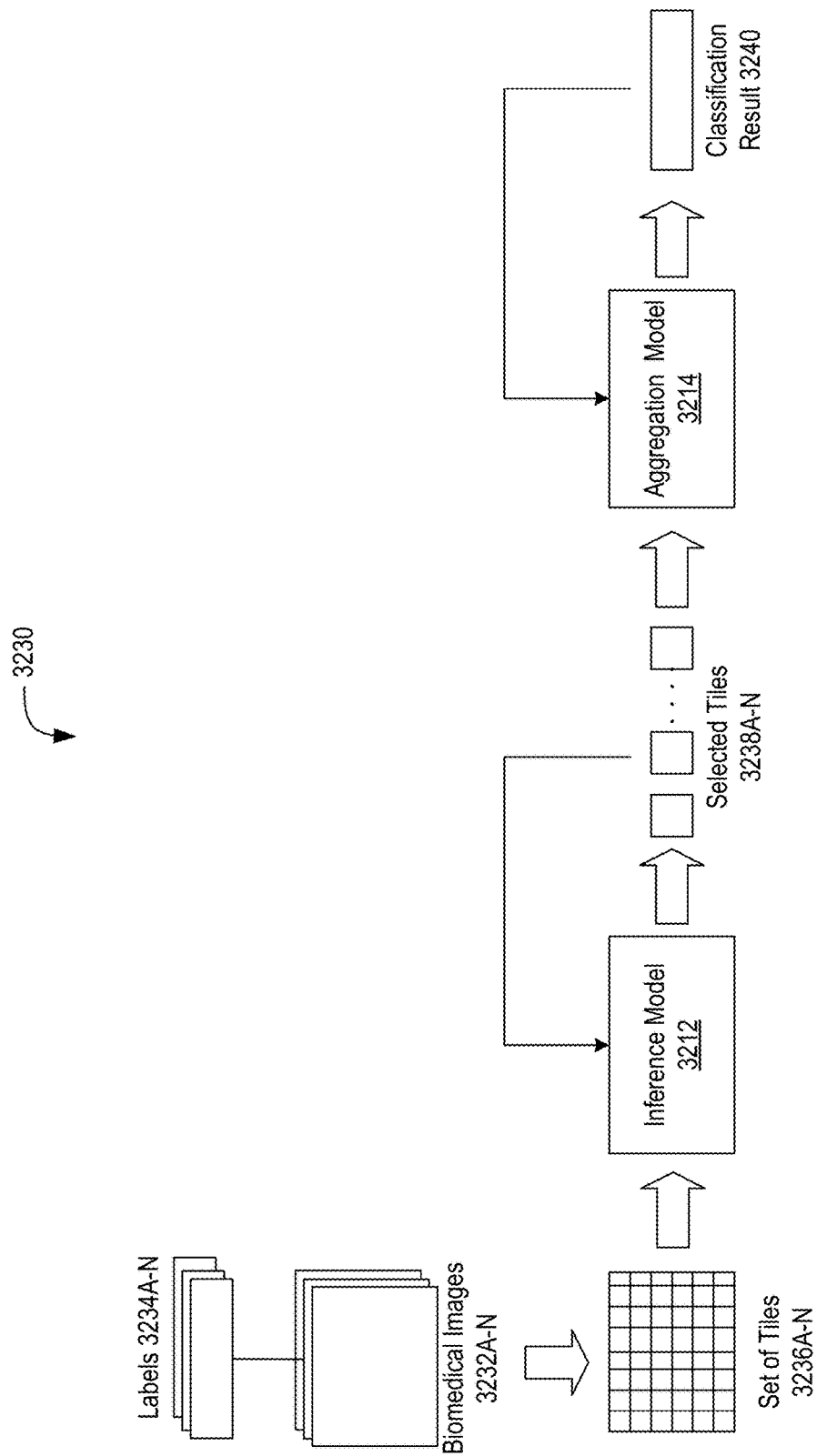
FIG. 32B depicts a process diagram of a system for classifying biomedical images and training models for classifying biomedical images using multiple-instance learning.

In further detail, with reference to a process diagram of a sequence 3230 depicted in FIG. 32B, the tile generator 3216 of the feature classifier 3208 may identify one or more biomedical images 3232A-N (hereinafter referred generally as biomedical images 3232). In some embodiments, the biomedical images 3232 may be of a micro-anatomical sample or specimen. The biomedical images 3232 may be, for example, a histological section with a hematoxylin and eosin (H&E) stain, hemosiderin stain, a Sudan stain, a Schiff stain, a Congo red stain, a Gram stain, a Ziehl-Neelsen stain, a Auramine-rhodamine stain, a trichrome stain, a Silver stain, and Wright's Stain, among others. In some embodiments, the tile generator 3216 may receive the biomedical images 3232 from the imaging device 3204. The receipt of the biomedical images 3232 from the imaging device 3204 may be under the runtime mode for the inference model 3212 or the aggregation model 3214. The imaging device 3204 may be a microscope communicatively coupled with the image classification system 3202. The imaging device 3204 may scan the micro-anatomical sample or specimen, and may generate the biomedical image 3232 from the scan.

In some embodiments, the tile generator 3216 may access the training database 3224 to retrieve the biomedical images 3232. The retrieval of the biomedical images 3232 from the training database 3224 may be under training mode for the inference model 3212. Each biomedical image 3232 retrieved from the training database 3324 may have a label 3234A-N (hereinafter referred generally as label 3234 and sometimes referred herein as an annotation). The training database 3324 may maintain a set of biomedical images 3232 with the label 3234 for training the inference model 3212 and the aggregation model 3214. The label 3234 may indicate a presence or a lack of a condition on the biomedical image 3232. The condition may be a pathological condition, such as a tumor, injury, scarring, dead cells, or other defect. In some embodiments, the label 3234 may indicate the presence or the lack of multiple conditions on the biomedical image 3232. For example, one label 3234 may indicate the presence of benign tumorous growth, while another label 3234 may indicate the presence of malignant tumor formation. To facilitate multiple instance learning (MIL) techniques, the label 3234 may not identify a specific location of the presence or the lack of the condition on the biomedical image 3232. Rather, the label 3234 may indicate that the condition is present somewhere on the biomedical image 3232.

For each biomedical image 3232, the tile generator 3216 may generate a set of tiles 3236A-N (hereinafter referred as tiles 3236) from the biomedical image 3232. Each tile 3236 may correspond to a portion of the biomedical image 3232. In some embodiments, the tile generator 3215 may partition or divide the biomedical image 3232 into the set of tiles 3236. In some embodiments, the tile generator 3216 may apply to one or more magnification factors to generate the set of tiles 3236. The magnification factors applied to the biomedical image 3232 may range from 3× to 100×. In some embodiments, the tile generator 3216 may generate the set of tiles 3236 from the biomedical image 3232 without overlap. In some embodiments, the tile generator 3216 may generate the set of tiles 3236 with an overlap of a set ratio. The ratio may range from 10% to 90% overlap between pairs of adjacent tiles 3236. In some embodiments, the set ratio for the overlap may depend on the magnification factor applied to the biomedical image 3232. For example, an overlap of 50% may be used at 10× magnification factor and an overlap of 67% maybe used at 5× magnification factor.

In some embodiments, the tile generator 3216 may identify or detect one or more regions of the biomedical image 3232 corresponding to negative space. The identification of the negative space may be in accordance with a feature detection algorithm. The negative space region of the biomedical image 3232 may lack any portion of the micro-anatomical sample or specimen. For example, the negative space may correspond to the region of the biomedical image 3232 that is null or white. In some embodiments, the tile generator 3216 may apply the one or more magnification factor to the biomedical image 3232, prior to the detection of the negative space. With the identification of the negative space, the tile generator 3216 may remove the corresponding region from the biomedical image 3232. In some embodiments, the tile generator 3216 may generate the set of tiles 3236 from the remaining one or more regions of the biomedical image 3232. In some embodiments, the tile generator 3216 may detect or identify a subset of the tiles 3236 generated from the biomedical image 3232 corresponding to the negative space (e.g., having at least 97% white space) using the feature detection algorithm. The tile generator 3216 may remove the identified subset of the set of tiles 3236 corresponding to the negative space.

The model applier 3218 may establish the inference model 3212. Under training mode for the image classification system, the model applier 3218 may initialize the inference model 3212. Under runtime mode, the model applier 3218 may identify the previously established inference model 3212. The inference model 3212 may determine a score for each tile 3236 generated from the biomedical image 3232. The score may indicate a likelihood that the tile 3236 includes at least one feature indicative of the presence of the condition. The score may be a numerical value, such as a probability, a percentage, or within a defined range of numbers (e.g., −1 to 1, 0 to 1, −10 to 10, or 0 to 100), to indicate the likelihood. The feature may be a visual characteristic, property, or object within the portion of the biomedical image 3232 corresponding to the slide 3236.

The inference model 3212 may have one or more parameters to determine the score for each tile 3236. The inference model 3212 may include a set of transform layers (e.g., convolutional layer, pooling layer, rectified layer, and normalization layer). The inference model 3212 may have any number of transform layers. Each transform layer may include at least one of the one or more parameters to convert the set of tiles 3236 to a set of feature maps and to determine the score for each tile 3236. Each transform layer may be of a predefined size to generate the feature maps of a predefined size. In some embodiments, the inference model 3212 may be a convolutional neural network (CNN) and a deep convolutional network (DCN), among others, with the set of transform layers. For example, the inference model 3212 may be the convolutional neural network detailed herein in Sections A and B. In contrast to the aggregation model 3214, the inference model 3212 may be a feedforward network without internal state memory, and may lack temporal or sequentially dependent behavior.

In initializing the inference model 3212 under training mode, the model applier 3218 may set the parameters of the inference model 3212. In some embodiments, the one or more parameters of the inference model 3212 may be set to random values. The random values may be generated using a pseudo-random number generator. In some embodiments, one or more parameters of the inference model 3212 may be set to a predefined value. The predefined value may be maintained on the training database 3224. In some embodiments, the model applier 3218 may set a number of the set of transform layers of the inference model 3212. In some embodiments, the model applier 3218 may set a size of the set of transform layers of the inference model 3212. In some embodiments, the model applier 3218 may set connections between transform layers in the inference model 3212 in initializing.

The model applier 3218 may apply the inference model 3212 to the set of tiles 3236 for each biomedical image 3232. In applying the inference model 3212, the model applier 3218 may apply the entire set of tiles 3236 as an input into the inference model 3212. In some embodiments, the model applier 3218 may identify an output generated from one transform layer in the inference model 3212. The model applier 3218 may feed the output generated from one transform layer as an input of the subsequent transform layer in the inference model 3212. The output from the first transform layer and onward may include a feature map. The input of the first transform layer may be the set of tiles 3236 generated from the biomedical image 3232. The input of the second transform layer and onward in the inference model 3212 may include the feature map generated from the previous transform layer. The model applier 3218 may repeat the feeding of the output of one transform layer into the input of the subsequent transform layer in the inference model 3212 until the last transform layer. By applying the inference model, the model applier 3218 may determine the score for each tile 3236. In some embodiments, the model applier 3218 may determine the score for each condition for each tile 3236. For example, one tile 3236 may be associated with a score indicating likelihood of presence of prostate cancer and another score indicating likelihood of bruising to the organ tissue on the tile 3236. In some embodiments, the model applier 3218 may identify the output of the last transform layer in the inference model 3212. The output may include the scores for all of the tiles 3236.

Based on the scores determined for the tiles 3236 from the application of the inference model 3212, the model applier 3218 may select a subset from the set of tiles 3236 to form a subset 3238A-N (hereinafter generally referred to as subset 3238 or selected tiles 3238). In some embodiments, the model applier 3218 may select the tiles 3236 with the highest scores to form the subset 3238. The selected tiles 3238 may represent the tiles 3236 with the highest likelihood of including a feature correlated with or corresponding to the presence of the condition. The number of tiles 3238 selected from the original set of tiles 3236 may be in accordance to a predefined number, and may range from 1 to 50. In some embodiments, the model applier 3218 may select the subset 3238 from the set of tiles 3236 for each condition. For example, the model applier 3218 may select one subset 3238 from the tiles 3236 for the condition of breast cancer based on the scores for breast cancer. In conjunction, the model applier 3218 may select another subset 3238 from the tiles 3236 for lesion to breast tissue based on the corresponding scores. Under the runtime mode, with the selection from the tiles 3236, the model applier 3218 may apply the aggregation model 3214 onto the selected tiles 3238, and feed the selected tiles 3238 into the input of the aggregation model 3214.

Under training mode, the error calculator 3220 of the model trainer 3210 may compare the scores for the selected tiles 3238 to a threshold value for the condition indicated by the label 3234 of the biomedical image 3232. The threshold value for the label 3234 may correspond to the occurrence of the condition specified by the label 3234, and may indicate a score at which to modify one or more parameters of the inference model 3212. For example, the threshold score may be set at 75% for the presence of the condition and 50% for the lack of the presence. The scores may be the same or may differ for the presence or the lack of the condition defined by the label 3234. In some embodiments, the threshold value may differ depending on the condition specified by the label 3234. In some embodiments, the label 3234 may specify the threshold value to be compared against. In some embodiments, an equality (e.g., less than or greater than) for the comparison performed by the error calculator 3220 may depend on the label 3234 indicating the presence or the lack of the condition. For example, when the label 3234 specifies the presence of the condition on the corresponding biomedical image 3232, the error calculator 3220 may determine whether the scores of the selected tiles 3238 are less than the threshold value for the condition. Conversely, when the label 3234 specifies the lack of the condition on the corresponding biomedical image 3232, the error calculator 3220 may determine whether the scores of the selected tiles 3238 are greater than or equal to the threshold value for the condition.

In some embodiments, the error calculator 3220 may calculate or determine an error measure between the score of each selected tile 3238 and a baseline value for the condition indicated by the label 3234 of the biomedical image 3232. The error measure may indicate one or more deviations from the score and an anticipated score as represented by the baseline value, and may be used to modify the parameters of the inference model 3212. The baseline value for the condition indicated by the label 3234 may indicate a score at which the inference model 3212 is expected to output. The baseline value for the presence of the condition may differ from the baseline value for the lack of the present of the value. For example, the baseline value for the presence of the condition may range between 0.9 and 1, while the baseline value for the lack of the condition may range between 0 and 0.2. In addition, the baseline value may differ depending on the condition. The error measure calculated by the error calculator 3220 may be in accordance with a loss function, such as mean square error (MSE), root mean square error (rMSE), an entropy loss (e.g., cross-entropy or relative entropy), a quadratic loss, and mean integrated square error, among others.

The model corrector 3222 may determine whether to modify the inference model 3212 based on the comparison of the scores of the selected tiles 3238 with the threshold value for the condition. The label 3234 may indicate the presence of the condition on the corresponding biomedical image 3232. In such a scenario, when at least one of the scores of the selected tiles 3238 is less than the threshold value, the model corrector 3222 may determine to modify the inference model 3212. On the other hand, when all the scores of the selected tiles 3238 are greater than or equal to the threshold value, the model corrector 3222 may determine to not modify the inference model 3212. Conversely, the label 3234 may indicate the lack of the condition on the corresponding biomedical image 3232. In this scenario, when at least one of the scores of the selected tiles 3238 is greater than or equal to the threshold value, the model corrector 3222 may determine to modify the inference model 3212. On the other hand, when all the scores of the selected tiles 3238 are less than the threshold value, the model corrector 3222 may determine to not modify the inference model 3212. The threshold value when the label 3234 indicates lack of the condition may be the same or may differ from the threshold value when the label 3234 indicates the presence of the condition. When the determination is not to modify the inference model 3212, the model corrector 3222 may maintain the inference model 3212. For example, the model corrector 3222 may maintain the parameters of the inference model 3212.

The model corrector 3222 of the model trainer 3210 may update or otherwise modify the inference model 3212. The modification of the inference model 3212 may be responsive to the determination to modify. In some embodiments, the model corrector 3222 may set, adjust, or otherwise change the one or more parameters of the inference model 3212 based on the condition indicated by the label 3234 for the biomedical image 3232 from which the tiles 3238 are selected. When the label 3234 indicates the presence of the condition on the corresponding biomedical image 3232, the model corrector 3222 may change the parameters of the inference model 3212 to increase the scores for the tiles 3236. On the other hand, when the label 3234 indicates the lack of the condition of the corresponding biomedical image 3232, the model corrector 3222 may change the parameters of the inference model 3212 to decrease the score for the tiles 3236.

In some embodiments, the model corrector 3222 may modify the inference model 3212 using the error measures calculated for the scores of the subset 3238. The modification of the inference model 3212 using the calculated error measures may be responsive to the determination to modify or independent of the determination of the modify. The model corrector 3222 may set, adjust, or otherwise change the one or more parameters of the inference model 3212 based on the error measures. In some embodiments, the model corrector 3222 may change the parameters of the inference model 3212 based on the whether error measures are positive or negative. In some embodiments, the model corrector 3222 may change the size of one or more of the transform layers in the inference model 3212 using the error measure. In some embodiments, the model corrector 3222 may change the number of transform layers in the inference model 3212 using the error measure. In modifying the parameters, the model corrector 3222 may perform regularization on the set of transform layers in the inference model 3212. The regularization may include, for example, dropout, drop connect, stochastic pooling, or max pooling, among others.

In some embodiments, the model corrector 3222 may determine whether the one or more parameters of the inference model 3212 have converged. The determination of whether the inference model 3212 has converged may be responsive to the modification of the inference model 3212. The model corrector 3222 may identify the one or more parameters of the inference model 3212 prior to the modification. The model corrector 3222 may identify the one or more parameters of the inference model 3212 with the modification. With these identifications, the model corrector 3222 may compare the parameters prior to the modification with the parameters subsequent to the modification. Based on the comparison, the model corrector 3222 may calculate or determine a difference between the parameters prior to the modification and the parameters with the modification. The model corrector 3222 may compare the determined difference to a convergence threshold value. The convergence threshold value may indicate the point in which to terminate further training of the inference model 3212. If the difference of the parameters is less than or equal to the convergence threshold value, the model corrector 3222 may determine that the inference model 3212 has reached convergence. Furthermore, the model corrector 3222 may terminate the training mode for the inference model 3212 and may switch to runtime mode. In contrast, if the difference of the parameters is greater than the convergence threshold value, the model corrector 3222 may determine that the inference model 3212 has not reached convergence. Additionally, the model corrector 3222 may continue the training mode for the inference model 3212.

In some embodiments, the model trainer 3210 for training the inference model 3212 may be implemented in accordance with the following pseudocode:
Extract tiles from whole slide images denoted by {parent slide id, slide-level target, x, y}, with (x,y) representing the top left corner of each tile;
Initialize the CNN model with ImageNet pre-trained parameters;
for each training epoch do
　for each tile in dataset do
　　Get image and convert to tensor;
　　Evaluate image on the current model;
　　Store the tumor probability for the current tile;
　Find the highest ranked tile of each slide;
　Create the training dataset consisting of the highest ranked tiles;
　for each batch of tiles in training dataset do
　　Get batch of images and convert to tensors;
　　Calculate the loss given the predictions of the CNN and the slide-level targets;
　　Update the CNN parameters by backpropagation;

The model applier 3218 may establish the aggregation model 3214. Under training mode, the aggregation model 3214, the model applier 3218 may initialize the aggregation model 3214. In some embodiments, the model applier 3218 may initialize the aggregation model 3214, responsive to determining that the inference model 3212 has reached convergence under the training mode. Under runtime mode, the model applier 3218 may identify the previously established aggregation model 3214. The aggregation model 3214 may determine a classification result for each biomedical image 3232 based on the selected tiles 3238 from the inference model 3212. The classification result may indicate whether the biomedical image 3232 contains at least one feature corresponding to the presence of the condition or the lack of the condition. The classification result may be, for example, a binary value (e.g., 0 and 1 or true and false) or one of an enumerate value or indicator (e.g., "high," "medium," or "low"), among others.

The aggregation model 3214 may have one or more parameters to determine the classification result for the biomedical image 3232. The aggregation model 3214 may include a set of transform layers (e.g., input layer, context layer, state layer, and hidden layer). The aggregation model 3214 may have any number of transform layers. Each transform layer may include at least one of the one or more parameters to determine the classification result for the biomedical image 3232. Each transform layer may include at least one of the one or more parameters to convert the set of tiles 3238 to a set of feature maps and to determine the classification result for the entire biomedical image 3232. Each transform layer may be of a predefined size to generate the feature maps of a predefined size. In some embodiments, the aggregation model 3214 may be a recurrent neural network (RNN), an echo state network (ESN), a long/short term memory (LSTM) network, a deep residual network (DRN), and gated recurrent units (GRU), among others, with the set of transform layers. For example, the aggregation model 3214 may be the recurrent neural network detailed herein in Section B. In contrast to the inference model 3212, the aggregation model 3214 may have internal state memory, and may exhibit temporally or sequentially dynamic behavior. In this manner, information may be integrated across the selected tiles 3238 from the inference model 3212 to determine the classification result for the overall biomedical image 3232.

In initializing the aggregation model 3214 under training mode, the model applier 3218 may set the parameters of the aggregation model 3214. In some embodiments, the model applier 3218 may commence training of the aggregation model 3214, responsive to determining that the inference model 3212 has reached convergence. In some embodiments, the one or more parameters of the aggregation model 3214 may be set to random values. The random values may be generated using a pseudo-random number generator. In some embodiments, one or more parameters of the aggregation model 3214 may be set to a predefined value. The predefined value may be maintained on the training database 3224. In some embodiments, the model applier 3218 may set a number of the set of transform layers of the aggregation model 3214. In some embodiments, the model applier 3218 may set a size of the set of transform layers of the aggregation model 3214. In some embodiments, the model applier 3218 may set connections between transform layers in the aggregation model 3214 in initializing.

The model applier 3218 may apply the aggregation model 3214 to the subset of tiles 3238 from the inference model 3212. In some embodiments, the model applier 3218 may identify the subset 3238 outputted by the inference model 3212. In some embodiments, the model applier 3218 may identify the subsets 3238 outputted by the inference model 3212 using the application of different magnification factors on the biomedical image 3232. For example, the input to the aggregation model 3214 may include selected tiles 3238 from the inference model 3212 applied to the biomedical image 3232 at the magnification factors of 5×, 10×, and 20×. In some embodiments, prior to feeding the subset 3238 from the different magnification factors, the model applier 3218 may generate an aggregate subset using a combination of the selected tiles 3238. The combination may be, for example, an average, a weighted average, or a predefined function, among others. The combination may be among tiles 3238 with similar center points (e.g., within 10%) or overlapping coordinates on the biomedical image 3232. Once generated, the model applier 3218 may feed the aggregate subset to the aggregation model 3214.

In applying the aggregation, the model applier 3218 may feed the selected tiles 3238 into the aggregation model 3214. In some embodiments, the model applier 3218 may apply the aggregation model 3214 to the subset of tiles 3238 in sequential order. The sequential order may arrange the tiles 3238 from the lowest coordinates to the highest coordinates relative to a starting point (e.g., top left point defined as (0,0)) on the biomedical image 3232. In some embodiments, the model applier 3218 may apply the aggregation model 3214 to the subset of tiles 3238 in random order. The random order may be generated by the model applier 3218 using a pseudo-random number generator.

The model applier 3218 may feed the output generated from one transform layer as an input of the subsequent transform layer in the aggregation model 3214. The output from the first transform layer and onward may include a feature map. The input of the first transform layer may be the set of tiles 3238 from the inference model 3212. The input of the second transform layer and onward in the aggregation model 3214 may include the feature map generated from the previous transform layer. The model applier 3218 may repeat the feeding of the output of one transform layer into the input of the subsequent transform layer in the aggregation model 3214 until the last transform layer. The model applier 3218 may identify the classification result for the condition from the last transform layer of the aggregation model 3214. The identification of the classification result may be repeated for multiple conditions (e.g., prostate tumor, breast lesion, and bruised tissue).

Under runtime mode, the model applier 3218 may provide the classification result generated by the aggregation model 3214. In some embodiments, the model applier 3218 may display the classification result onto the display 3206. The display 3206 may include any monitor, such as a liquid crystal display (LCD), an organic light-emitting diode (OLED) monitor, and a cathode ray tube (CRT), among others. The display 3206 may be communicatively coupled with the image classification system 3202, and may render the classification result. In addition, the model applier 3218 may display the biomedical image 3232 for which the classification result was generated on the display 3206. Furthermore, the model applier 3218 may indicate a location in the biomedical image 3232 corresponding to the selected tiles 3238 on the display 3206.

Under training mode, the error calculator 3220 may compare the classification result determined by the aggregation model 3214 with the label 3234 for the biomedical image 3232. As discussed above, the label 3234 may indicate the presence or the lack of the condition on the biomedical image 3232. Moreover, the classification result may indicate the presence or the lack of the condition on the biomedical image 3232. In comparing, the error calculator 3220 may determine whether the classification result from the aggregation model 3214 matches the indication of the label 3234. Whether to modify the aggregation model 3214 may be based on the determination. When the classification result does not match the indication, the error calculator 3220 may determine to modify the aggregation model 3214. In some embodiments, the error calculator 3220 may set, adjust, or otherwise change the one or more parameters of the aggregation model 314 based on the mismatch between the classification result and the indication. Conversely, when the classification matches the indication, the error calculator 3220 may determine not to modify and maintain the aggregation model 3214. For example, the error calculator 3220 may maintain the parameters of the aggregation model 3214.

In some embodiments, the error calculator 3220 may calculate or determine an error measure between the classification result from the aggregation model 3214 and the indication of the label 3234. The determination of the error measure may be performed responsive to determination of the mismatch between the classification result and the indication on the label 3234. The error measure may indicate one or more deviations from the anticipated classification result as indicated by the label 3234 for the biomedical image 3232, and may be used to modify the aggregation model 3214. In some embodiments, the determination of the error measure may be over multiple classification results from the aggregation model 3214 compared against the indications of the corresponding labels 3234. In some embodiments, the multiple classification results may be from the same biomedical image 3232 with the tiles 3236 generated using different magnification factors. The error measure calculated by the error calculator 3220 may be in accordance with a loss function, such as mean square error (MSE), root mean square error (rMSE), an entropy loss (e.g., cross-entropy or relative entropy), a quadratic loss, and mean integrated square error, among others.

The model corrector 3222 may update or modify the aggregation model 3214. The modification of the aggregation model 3214 may be responsive to the determination to modify. In some embodiments, the model corrector 3222 may modify the one or more parameters of the aggregation model 3214 using the determined error measures between the classification results and the corresponding indications on the labels 3234. The modification of the aggregation model 3214 using the calculated error measures may be responsive to the determination to modify or independent of the determination of the modify. The model corrector 3222 may set, adjust, or otherwise change the one or more parameters of the aggregation model 3214 based on the error measures. In some embodiments, the model corrector 3222 may change the parameters of the aggregation model 3214 based on the whether error measures are positive or negative. In some embodiments, the model corrector 3222 may change the size of one or more of the transform layers in the aggregation model 3214 using the error measure. In some embodiments, the model corrector 3222 may change the number of transform layers in the aggregation model 3214 using the error measure. In modifying the parameters, the model corrector 3222 may perform regularization on the set of transform layers in the inference model 3212. The regularization may include, for example, dropout, drop connect, stochastic pooling, or max pooling, among others. In some embodiments, the model corrector 3222 may modify the aggregation model 3214 using the error measures in accordance with an iterative optimization algorithm, such as a gradient descent or stochastic gradient descent.

In some embodiments, model corrector 3222 may determine whether the one or more parameters of the aggregation model 3214 have converged. The determination of whether the aggregation model 3214 has converged may be responsive to the modification of the aggregation model 3214. The model corrector 3222 may identify the one or more parameters of the aggregation model 3214 prior to the modification. The model corrector 3222 may identify the one or more parameters of the aggregation model 3214 with the modification. With these identifications, the model corrector 3222 may compare the parameters prior to the modification with the parameters subsequent to the modification. Based on the comparison, the model corrector 3222 may calculate or determine a difference between the parameters prior to the modification and the parameters with the modification. The model corrector 3222 may compare the determined difference to a convergence threshold value. The convergence threshold value may indicate the point in which to terminate further training of the aggregation model 3214. If the difference of the parameters is less than or equal to the convergence threshold value, the model corrector 3222 may determine that the aggregation model 3214 has reached convergence. Furthermore, the model corrector 3222 may terminate the training mode for the aggregation model 3214. In contrast, if the difference of the parameters is greater than the convergence threshold value, the model corrector 3222 may determine that the aggregation model 3214 has not reached convergence. Additionally, the model corrector 3222 may continue the training mode for the aggregation model 3214.

In addition to the reasons discussed in Sections A and B, the inference model 3212 and the aggregation model 3214 may identify pathological features on biomedical images 3232 with higher accuracy. Furthermore, by eliminating the manual inspection of biomedical images for diagnosis, the recognition of such features on biomedical images 3232 may be performed faster.

Figure 33A:
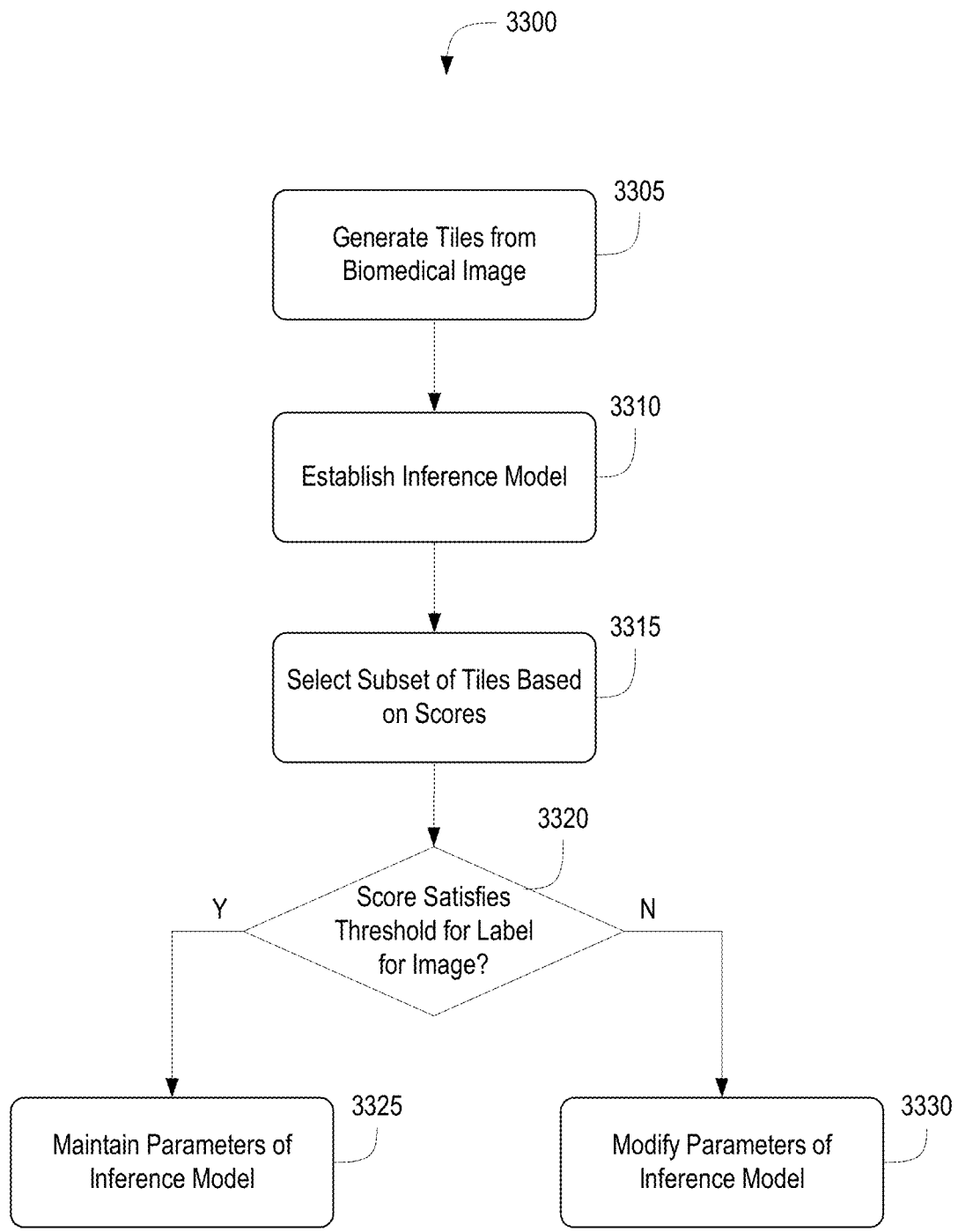
FIG. 33A depicts a flow diagram of a method of training models for classifying biomedical images using multiple-instance learning.

Referring now to FIG. 33A, depicted is a flow diagram of a method of training models for classifying biomedical images using multiple-instance learning. The method 3300 may be implemented using any of the schemata detailed herein in Sections A and B, the system 3200 detailed herein, or the computing system 3400 described below in conjunction with FIGS. 34A-D. The method 3300 may be performed in conjunction with methods 3335 or 3370. In brief overview, the image classifier may generate tiles from a biomedical image (3305). The image classifier may establish an inference model (3310). The image classifier may select a subset of tiles based on scores (3315). The image classifier may determine whether the score satisfies a threshold for a label of the biomedical image (3320). If the score satisfies the threshold for the label, the image classifier may maintain parameters of the inference model (3325). Otherwise, if the score does not satisfy the threshold for the label, the image classifier may modify the parameters of the inference model (3330).

In further detail, the image classifier (e.g., the image classification system 3202) may generate tiles (e.g., the set of tiles 3236) from a biomedical image (e.g., the biomedical image 3232) (3305). The biomedical image may be retrieved from an imaging device or from a training dataset, and may be of a histological section with a hematoxylin and eosin (H&E) stain. The biomedical image from the training dataset may be associate with a label. The label may indicate a presence or a lack of a pathological condition non the biomedical image. The image classifier may generate the tiles at various magnification factor applied to the biomedical image. The image classifier may also generate the tiles to overlap with one another at a set ratio.

The image classifier may establish an inference model (e.g., the inference model 3212) (3310). The inference model may have one or more parameters in a set of transform layers for calculating or determining a score for each tile. The inference model may be a convolutional neural network. The score may indicate a likelihood that a feature on the tile correlates with the presence of the condition. The parameters of the inference model may be initially set to random values. The image classifier may select a subset of tiles (e.g., selected tile 3238)) based on scores (3315). The selection of the subset of tiles from the initial set may be based on the scores determined by the inference model. The image classifier may select a predefined number of tiles with the highest scores. The tiles of the subset may represent the corresponding portion on the biomedical image most likely to contain the pathological condition.

The image classifier may determine whether the score satisfies a threshold for a label of the biomedical image (3320). The threshold for the label may indicate a score at which to modify the parameters of the inference model. Whether the score satisfies the threshold may depend on the indication of the label for the biomedical image. When the label specifies the presence of the condition, the image classifier may determine whether the scores of the selected tiles are less than the threshold for the condition. If the scores are greater than the threshold, the image classifier may determine that the score satisfies the threshold. Conversely, the if the scores are less than or equal to the threshold, the image classifier may determine that the score does not satisfy the threshold. When the label specifies the lack of the condition, the image classifier may determine whether the scores of the selected tiles are greater than the threshold for the condition. If the scores are greater than the threshold, the image classifier may determine that the score does not satisfy the threshold. Conversely, the if the scores are less than or equal to the threshold, the image classifier may determine that the score satisfies the threshold If the score satisfies the threshold for the label, the image classifier may maintain parameters of the inference model (3325). Otherwise, if the score does not satisfy the threshold for the label, the image classifier may modify the parameters of the inference model (3330). The image classifier may also determine an error measure between the scores of the selected tiles and a baseline value for the condition. The baseline value may indicate a score at which the inference model is expected to output. Using the error measure, the image classifier may change the parameters of the inference model.

Figure 33B:
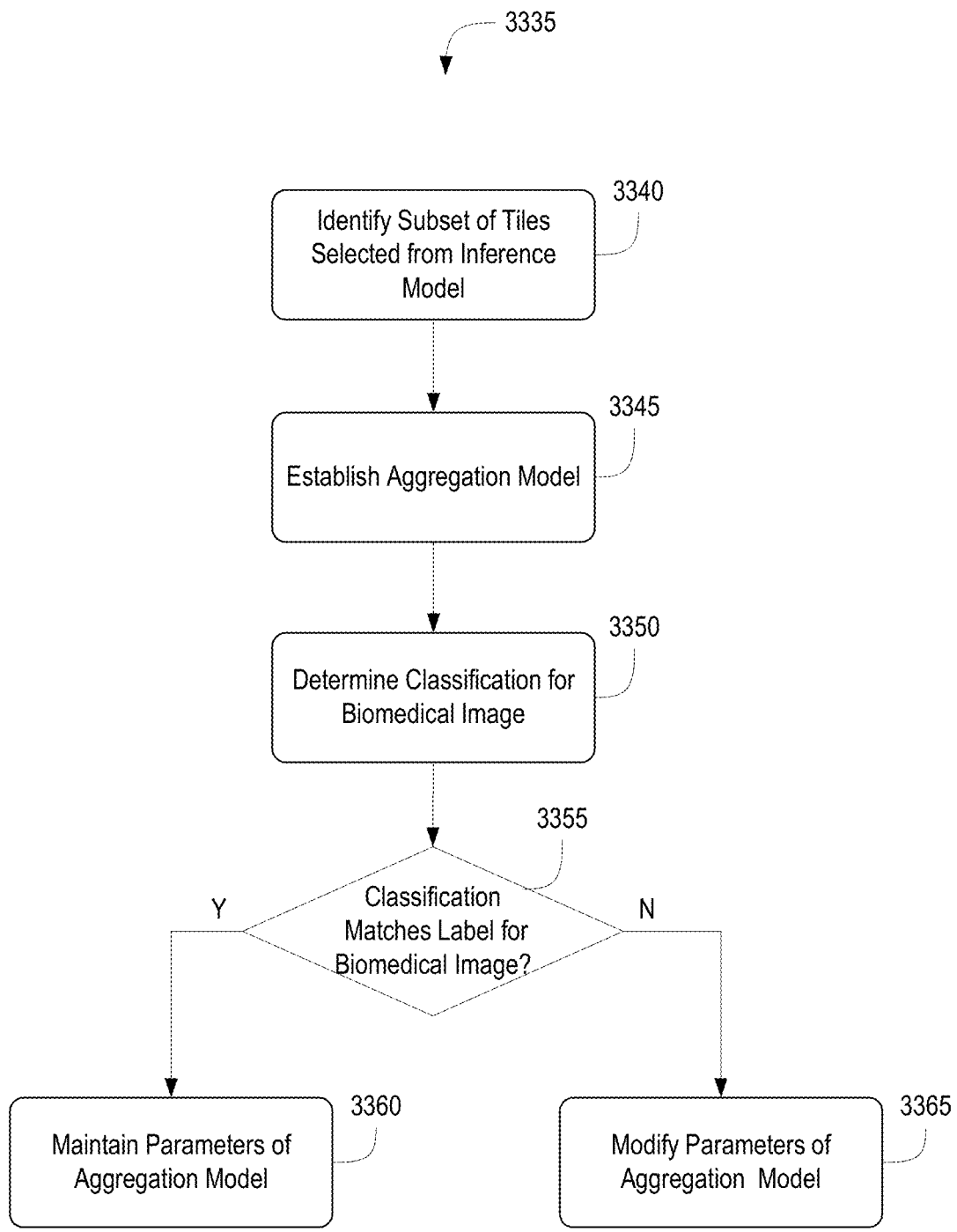
FIG. 33B depicts a flow diagram of a method of training models for classifying biomedical images using multiple-instance learning.

Referring now to FIG. 33B, depicted is a flow diagram of a method 3335 of training models for classifying biomedical images using multiple-instance learning. The method 3335 may be implemented using any of the schemata detailed herein in Sections A and B, the system 3200 detailed herein, or the computing system 3400 described below in conjunction with FIGS. 34A-D. The method 3335 may be performed in conjunction with methods 3300 or 3370. In brief overview, an image classifier may identify a subset of tiles selected from an inference model (3340). The image classifier may establish an aggregation model (3345). The image classifier may determine a classification for the biomedical image (3350). The image classifier may determine whether the classification matches a label for the biomedical image (3355). If the classification matches the label, the image classifier may maintain parameters of the aggregation model (3360). On the other hand, if the classification does not match the label, the image classifier may modify the parameters of the aggregation model (3365).

In further detail, an image classifier may identify a subset of tiles (e.g., selected tiles 3238) selected from an inference model (e.g., the inference model 3212) (3340). The image classifier may retrieve the subset of tiles from the output of the inference model. The image classifier may also aggregate the subset of tiles from the inference model for the same biomedical image at different magnification factors. The image classifier may combine the tiles from the inference model with similar center coordinates (e.g., within 10% difference).

The image classifier may establish an aggregation model (e.g., the aggregation model 3214) (3345). The aggregation model may have one or more parameters in a set of transform layers to determine a classification result for the biomedical image using the selected subset of tiles. The aggregation model may be a recurrent neural network. The classification result may indicate the presence or the lack of the pathological condition on the biomedical image. The image classifier may determine a classification for the biomedical image (e.g., the biomedical image 3232) (3350). The image classifier may apply the aggregation model onto the selected subset of tiles. The image classifier may feed the selected subset of tiles in sequential order or random order into the aggregation model. By applying the aggregation model, the image classifier may generate the classification result for the biomedical image.

The image classifier may determine whether the classification matches a label (e.g., the label 3234) for the biomedical image (3355). The image classifier may identify the indication from the label for the biomedical image. The label may indicate the presence or the lack of the pathological on the biomedical image. If the classification matches the label, the image classifier may maintain parameters of the aggregation model (3360). On the other hand, if the classification does not match the label, the image classifier may modify the parameters of the aggregation model (3365). The image classifier may calculate an error measure over the classification results of multiple subsets of tiles for the same biomedical image at different magnification factors. The error measure may include cross-entropy loss. Using the error measure, the image classifier may change the parameters of the aggregation model.

Figure 33C:
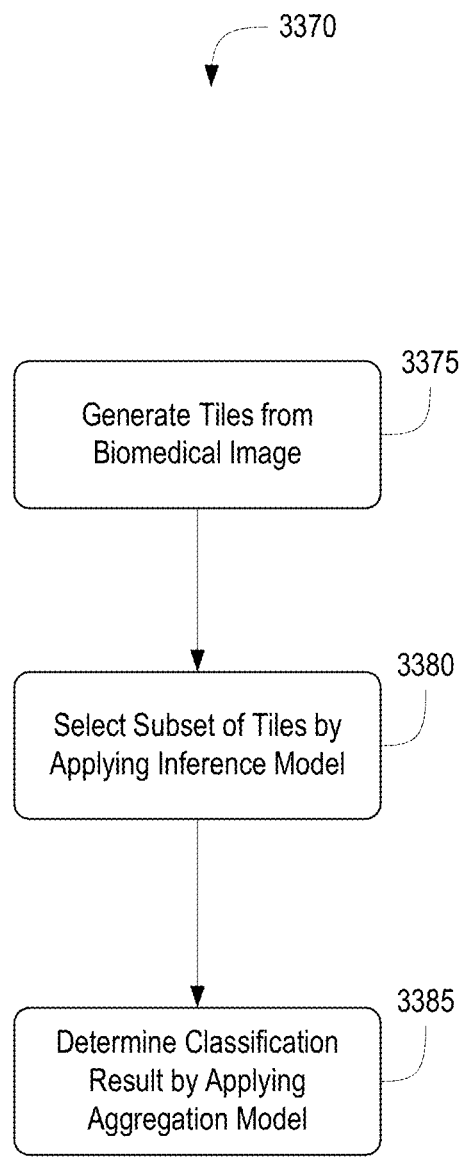
FIG. 33C depicts a flow diagram of a method of classifying biomedical images.

Referring now to FIG. 33C, a flow diagram of a method 3370 of classifying biomedical images. The method 3370 may be implemented using any of the schemata detailed herein in Sections A and B, the system 3200 detailed herein, or the computing system 3400 described below in conjunction with FIGS. 34A-D. The method 3370 may be performed in conjunction with methods 3300 or 3335. In brief overview, an image classifier may generate tiles from a biomedical image (3375). The image classifier may select a subset of tiles by applying an inference model (3380). The image classifier may determine a classification result by applying an aggregation model (3385).

In further detail, an image classifier may generate tiles (e.g., the set of tiles 3236) from a biomedical image (e.g., the biomedical image 3232) (3375). The biomedical image may be retrieved from an imaging device or from a training dataset, and may be of a histological section with a hematoxylin and eosin (H&E) stain. The biomedical image from the training dataset may be associate with a label. The label may indicate a presence or a lack of a pathological condition non the biomedical image. The image classifier may generate the tiles at various magnification factor applied to the biomedical image. The image classifier may also generate the tiles to overlap with one another at a set ratio.

The image classifier may select a subset of tiles (e.g., the selected tiles 3238) by applying an inference model (e.g., the inference model 3212) (3380). The inference model may have one or more parameters in a set of transform layers for calculating or determining a score for each tile. The inference model may be a convolutional neural network. The score may indicate a likelihood that a feature on the tile correlates with the presence of the condition. The selection of the subset of tiles from the initial set may be based on the scores determined by the inference model. The image classifier may select a predefined number of tiles with the highest scores. The tiles of the subset may represent the corresponding portion on the biomedical image most likely to contain the pathological condition.

The image classifier may determine a classification result by applying an aggregation model (e.g., the aggregation model 3214) (3385). The aggregation model may have one or more parameters in a set of transform layers to determine a classification result for the biomedical image using the selected subset of tiles from the inference model. The aggregation model may be a recurrent neural network. The classification result may indicate the presence or the lack of the pathological condition on the biomedical image. The image classifier may apply the aggregation model onto the selected subset of tiles. The image classifier may feed the selected subset of tiles in sequential order or random order into the aggregation model. By applying the aggregation model, the image classifier may generate the classification result for the biomedical image.

D. Computing and Network Environment

Figure 34A:
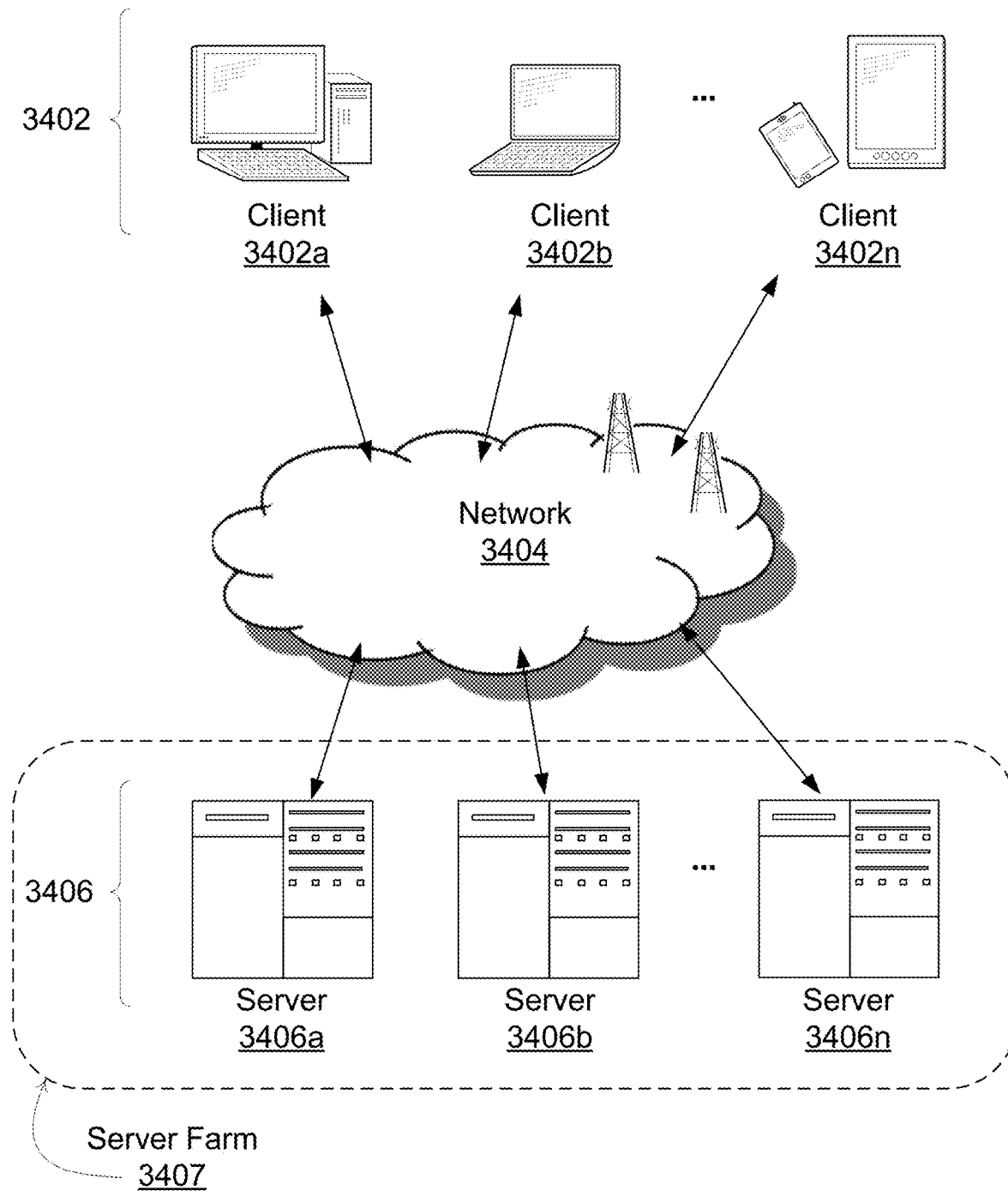
FIG. 34A is a block diagram depicting an embodiment of a network environment comprising client devices in communication with server devices.

It may be helpful to describe aspects of the operating environment as well as associated system components (e.g., hardware elements) in connection with the methods and systems described in Sections A, B, and C. Referring to FIG. 34A, an embodiment of a network environment is depicted. In brief overview, the illustrated exploring network environment includes one or more clients 3402a-1602n (also generally referred to as local machine(s) 3402, client(s) 3402, client node(s) 3402, client machine(s) 3402, client computer(s) 3402, client device(s) 3402, endpoint(s) 3402, or endpoint node(s) 3402) in communication with one or more servers 3406*a*-1506*n* (also generally referred to as server(s) 3406, node 3406, or remote machine(s) 3406) via one or more networks 3404. In some embodiments, a client 3402 has the capacity to function as both a client node seeking access to resources provided by a server and as a server providing access to hosted resources for other clients 3402*a*-3402*n*.

Although FIG. 34A shows a network 3404 between the clients 3402 and the servers 3406, the clients 3402 and the servers 3406 may be on the same network 3404. In some embodiments, there are multiple networks 3404 between the clients 3402 and the servers 3406. In one of these embodiments, a network 3404' (not shown) may be a private network and a network 3404 may be a public network. In another of these embodiments, a network 3404 may be a private network and a network 3404' a public network. In still another of these embodiments, networks 3404 and 3404' may both be private networks.

The network 3404 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 3404 may be any type and/or form of network. The geographical scope of the network 3404 may vary widely and the network 3404 can be a body area network (BAN), a personal area network (PAN), a local-area network (LAN), e.g. Intranet, a metropolitan area network (MAN), a wide area network (WAN), or the Internet. The topology of the network 3404 may be of any form and may include, e.g., any of the following: point-to-point, bus, star, ring, mesh, or tree. The network 3404 may be an overlay network, which is virtual and sits on top of one or more layers of other networks 3404'. The network 3404 may be of any such network topology as known to those ordinarily skilled in the art capable of supporting the operations described herein. The network 3404 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 3404 may be a type of a broadcast network, a telecommunications network, a data communication network, or a computer network.

In some embodiments, the system may include multiple, logically-grouped servers 3406. In one of these embodiments, the logical group of servers may be referred to as a server farm 3407 or a machine farm 3407. In another of these embodiments, the servers 3406 may be geographically dispersed. In other embodiments, a machine farm 3407 may be administered as a single entity. In still other embodiments, the machine farm 3407 includes a plurality of machine farms 38. The servers 3406 within each machine farm 3407 can be heterogeneous—one or more of the servers 3406 or machines 3406 can operate according to one type of operating system platform (e.g., WINDOWS NT, manufactured by Microsoft Corp. of Redmond, Wash.), while one or more of the other servers 3406 can operate on according to another type of operating system platform (e.g., Unix, Linux, or Mac OS X).

In one embodiment, servers 3406 in the machine farm 3407 may be stored in high-density rack systems, along with associated storage systems, and located in an enterprise data center. In this embodiment, consolidating the servers 3406 in this way may improve system manageability, data security, the physical security of the system, and system performance by locating servers 3406 and high performance storage systems on localized high performance networks. Centralizing the servers 3406 and storage systems and coupling them with advanced system management tools allows more efficient use of server resources.

The servers 3406 of each machine farm 3407 do not need to be physically proximate to another server 3406 in the same machine farm 3407. Thus, the group of servers 3406 logically grouped as a machine farm 3407 may be interconnected using a wide-area network (WAN) connection or a metropolitan-area network (MAN) connection. For example, a machine farm 3407 may include servers 3406 physically located in different continents or different regions of a continent, country, state, city, campus, or room. Data transmission speeds between servers 3406 in the machine farm 3407 can be increased if the servers 3406 are connected using a local-area network (LAN) connection or some form of direct connection. Additionally, a heterogeneous machine farm 3407 may include one or more servers 3406 operating according to a type of operating system, while one or more other servers 3406 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 3407 may be decentralized. For example, one or more servers 3406 may comprise components, subsystems and modules to support one or more management services for the machine farm 3407. In one of these embodiments, one or more servers 3406 provide functionality for management of dynamic data, including techniques for handling failover, data replication, and increasing the robustness of the machine farm 3407. Each server 3406 may communicate with a persistent store and, in some embodiments, with a dynamic store.

Server 3406 may be a file server, application server, web server, proxy server, appliance, network appliance, gateway, gateway server, virtualization server, deployment server, SSL VPN server, or firewall. In one embodiment, the server 3406 may be referred to as a remote machine or a node. In another embodiment, a plurality of nodes may be in the path between any two communicating servers.

Figure 34B:
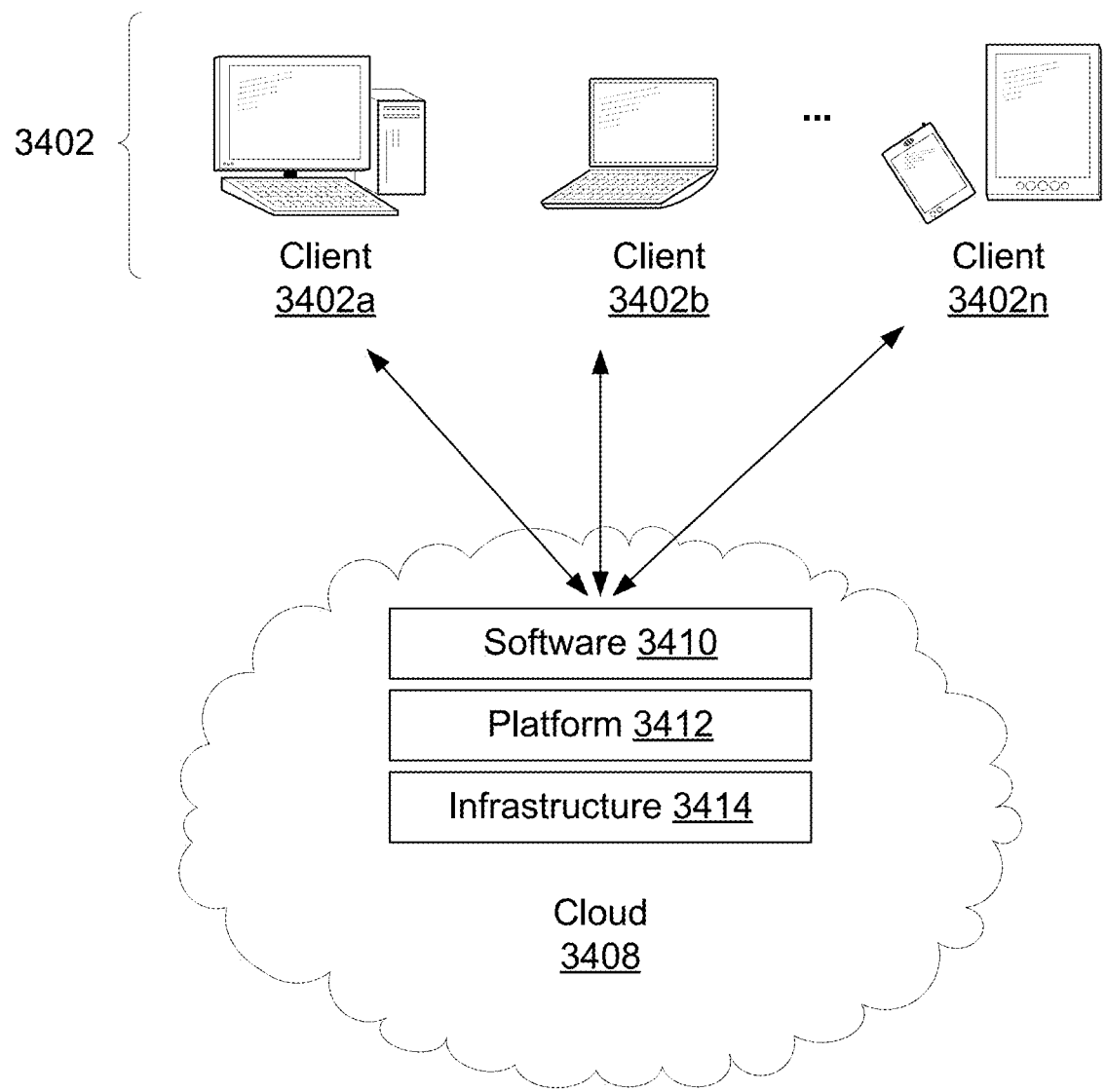
FIG. 34B is a block diagram depicting a cloud computing environment comprising client devices in communication with a cloud service provider.

Referring to FIG. 34B, a cloud computing environment is depicted. A cloud computing environment may provide client 3402 with one or more resources provided by a network environment. The cloud computing environment may include one or more clients 3402a-3402n, in communication with the cloud 3408 over one or more networks 3404. Clients 3402 may include, e.g., thick clients, thin clients, and zero clients. A thick client may provide at least some functionality even when disconnected from the cloud 3408 or servers 3406. A thin client or a zero client may depend on the connection to the cloud 3408 or server 3406 to provide functionality. A zero client may depend on the cloud 3408 or other networks 3404 or servers 3406 to retrieve operating system data for the client device. The cloud 3408 may include back end platforms, e.g., servers 3406, storage, server farms or data centers.

The cloud 3408 may be public, private, or hybrid. Public clouds may include public servers 3406 that are maintained by third parties to the clients 3402 or the owners of the clients. The servers 3406 may be located off-site in remote geographical locations as disclosed above or otherwise. Public clouds may be connected to the servers 3406 over a public network. Private clouds may include private servers 3406 that are physically maintained by clients 3402 or owners of clients. Private clouds may be connected to the servers 3406 over a private network 3404. Hybrid clouds 3408 may include both the private and public networks 3404 and servers 3406.

The cloud 3408 may also include a cloud based delivery, e.g. Software as a Service (SaaS) 3410, Platform as a Service (PaaS) 3412, and Infrastructure as a Service (IaaS) 3414. IaaS may refer to a user renting the use of infrastructure resources that are needed during a specified time period. IaaS providers may offer storage, networking, servers or virtualization resources from large pools, allowing the users to quickly scale up by accessing more resources as needed. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources.

Clients 3402 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 3402 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 3402 may access SaaS resources through the use of web-based user interfaces, provided by a web browser. Clients 3402 may also access SaaS resources through smartphone or tablet applications, including. Clients 3402 may also access SaaS resources through the client operating system.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 34C:
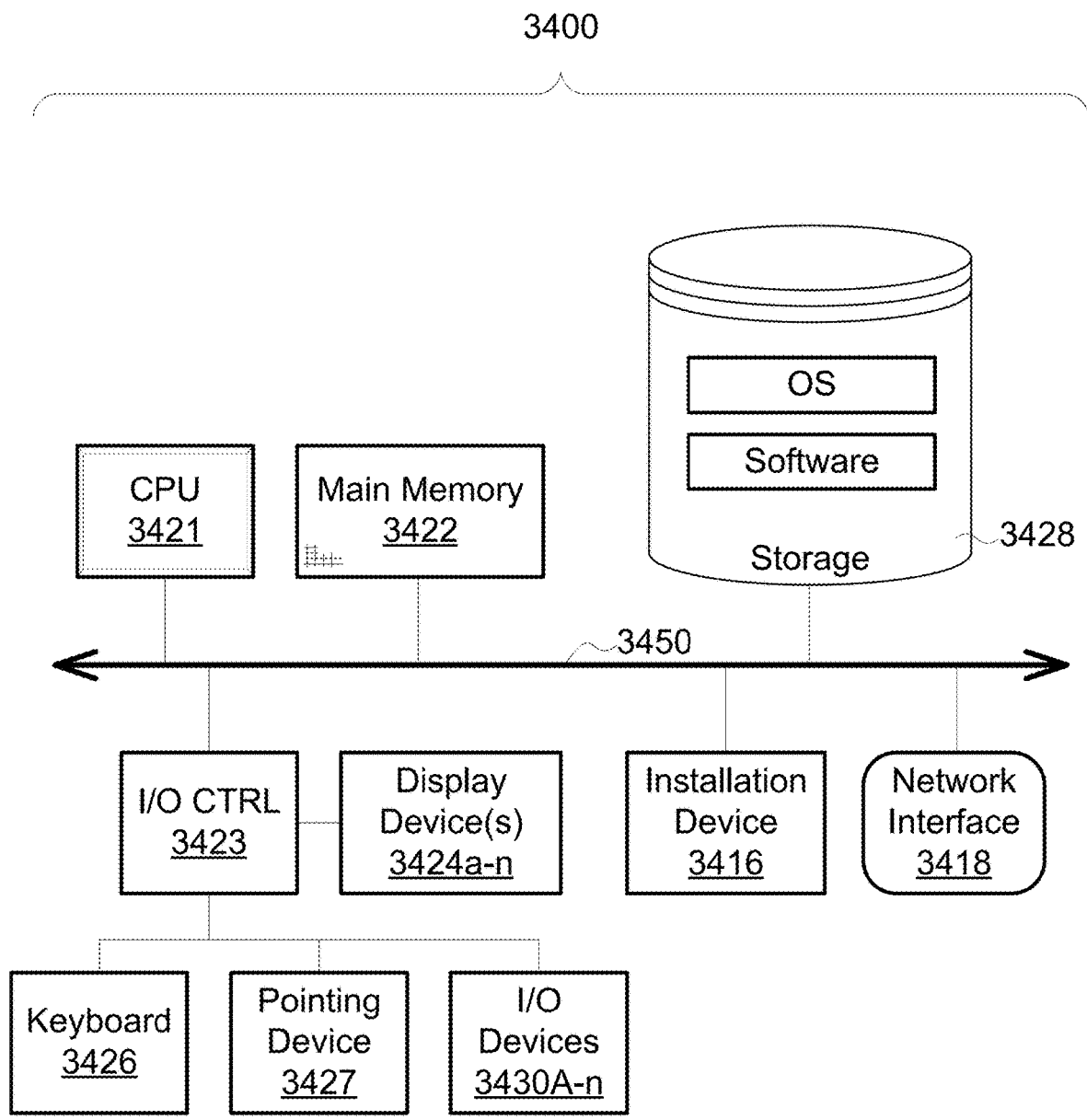
FIGS. 34C and 34D are block diagrams depicting embodiments of computing devices useful in connection with the methods and systems described herein
Figure 34D:
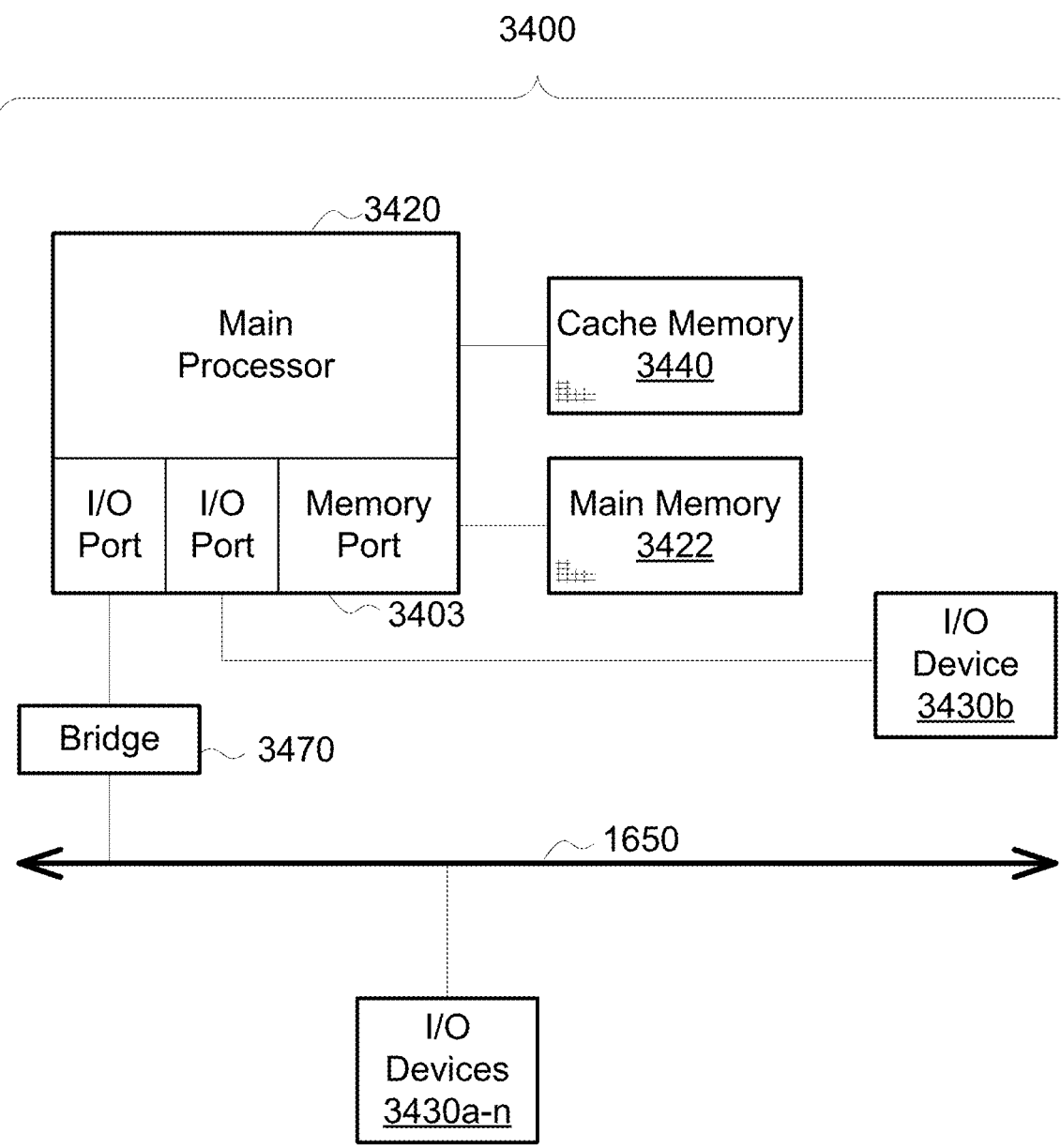

The client 3402 and server 3406 may be deployed as and/or executed on any type and form of computing device, e.g. a computer, network device or appliance capable of communicating on any type and form of network and performing the operations described herein. FIGS. 34C and 34D depict block diagrams of a computing device 3400 useful for practicing an embodiment of the client 3402 or a server 3406. As shown in FIGS. 34C and 34D, each computing device 3400 includes a central processing unit 3421, and a main memory unit 3422. As shown in FIG. 34C, a computing device 3400 may include a storage device 3428, an installation device 3416, a network interface 3418, an I/O controller 3423, display devices 3424a-3424n, a keyboard 3426 and a pointing device 3427, e.g. a mouse. The storage device 3428 may include, without limitation, an operating system, and/or software 3420. As shown in FIG. 34D, each computing device 3400 may also include additional optional elements, e.g. a memory port 3403, a bridge 3470, one or more input/output devices 3430a-3430n (generally referred to using reference numeral 3430), and a cache memory 3440 in communication with the central processing unit 3421.

The central processing unit 3421 is any logic circuitry that responds to and processes instructions fetched from the main memory unit 3422. In many embodiments, the central processing unit 3421 is provided by a microprocessor unit. The computing device 3400 may be based on any of these processors, or any other processor capable of operating as described herein. The central processing unit 3421 may utilize instruction level parallelism, thread level parallelism, different levels of cache, and multi-core processors. A multi-core processor may include two or more processing units on a single computing component.

Main memory unit 3422 may include one or more memory chips capable of storing data and allowing any storage location to be directly accessed by the microprocessor 3421. Main memory unit 3422 may be volatile and faster than storage 3428 memory. Main memory units 3422 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 3422 or the storage 3428 may be non-volatile; e.g., non-volatile read access memory (NVRAM), flash memory non-volatile static RAM (nvSRAM), Ferroelectric RANI (FeRAM), Magnetoresistive RANI (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 3422 may be based on any of the above described memory chips, or any other available memory chips capable of operating as described herein. In the embodiment shown in FIG. 34C, the processor 3421 communicates with main memory 3422 via a system bus 3450 (described in more detail below). FIG. 34D depicts an embodiment of a computing device 3400 in which the processor communicates directly with main memory 3422 via a memory port 3403. For example, in FIG. 34D the main memory 3422 may be DRDRAM.

FIG. 34D depicts an embodiment in which the main processor 3421 communicates directly with cache memory 3440 via a secondary bus, sometimes referred to as a backside bus. In other embodiments, the main processor 3421 communicates with cache memory 3440 using the system bus 3450. Cache memory 3440 typically has a faster response time than main memory 3422 and is typically provided by SRAM, BSRAM, or EDRAM. In the embodiment shown in FIG. 34D, the processor 3421 communicates with various I/O devices 3430 via a local system bus 3450. Various buses may be used to connect the central processing unit 3421 to any of the I/O devices 3430, including a PCI bus, a PCI-X bus, or a PCI-Express bus, or a NuBus. For embodiments in which the I/O device is a video display 3424, the processor 3421 may use an Advanced Graphics Port (AGP) to communicate with the display 3424 or the I/O controller 3423 for the display 3424. FIG. 34D depicts an embodiment of a computer 3400 in which the main processor 3421 communicates directly with I/O device 3430b or other processors 3421' via HYPERTRANSPORT, RAPIDIO, or INFINIBAND communications technology. FIG. 34D also depicts an embodiment in which local busses and direct communication are mixed: the processor 3421 communicates with I/O device 3430a using a local interconnect bus while communicating with I/O device 3430b directly.

A wide variety of I/O devices 3430a-3430n may be present in the computing device 3400. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 3430a-3430n may include a combination of multiple input or output devices, including. Some devices 3430a-3430n allow gesture recognition inputs through combining some of the inputs and outputs. Some devices 3430a-3430n provides for facial recognition which may be utilized as an input for different purposes including authentication and other commands. Some devices 3430a-3430n provides for voice recognition and inputs. Additional devices 3430a-3430n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, such as on a table-top or on a wall, and may also interact with other electronic devices. Some I/O devices 3430a-3430n, display devices 3424a-3424n or group of devices may be augment reality devices. The I/O devices may be controlled by an I/O controller 3423 as shown in FIG. 34C. The I/O controller may control one or more I/O devices, such as, e.g., a keyboard 3426 and a pointing device 3427, e.g., a mouse or optical pen. Furthermore, an I/O device may also provide storage and/or an installation medium 3416 for the computing device 3400. In still other embodiments, the computing device 3400 may provide USB connections (not shown) to receive handheld USB storage devices. In further embodiments, an I/O device 3430 may be a bridge between the system bus 3450 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 3424a-3424n may be connected to I/O controller 3423. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 3424a-3424n may also be a head-mounted display (HMD). In some embodiments, display devices 3424a-3424n or the corresponding I/O controllers 3423 may be controlled through or have hardware support for OPENGL or DIRECTX API or other graphics libraries.

In some embodiments, the computing device 3400 may include or connect to multiple display devices 3424a-3424n, which each may be of the same or different type and/or form. As such, any of the I/O devices 3430a-3430n and/or the I/O controller 3423 may include any type and/or form of suitable hardware, software, or combination of hardware and software to support, enable or provide for the connection and use of multiple display devices 3424a-3424n by the computing device 3400. For example, the computing device 3400 may include any type and/or form of video adapter, video card, driver, and/or library to interface, communicate, connect or otherwise use the display devices 3424a-3424n. In one embodiment, a video adapter may include multiple connectors to interface to multiple display devices 3424a-3424n. In other embodiments, the computing device 3400 may include multiple video adapters, with each video adapter connected to one or more of the display devices 3424a-3424n. In some embodiments, any portion of the operating system of the computing device 3400 may be configured for using multiple displays 3424a-3424n. In other embodiments, one or more of the display devices 3424a-3424n may be provided by one or more other computing devices 3400a or 3400b connected to the computing device 3400, via the network 3404. In some embodiments software may be designed and constructed to use another computer's display device as a second display device 3424a for the computing device 3400.

Referring again to FIG. 34C, the computing device 3400 may comprise a storage device 3428 (e.g. one or more hard disk drives or redundant arrays of independent disks) for storing an operating system or other related software, and for storing application software programs such as any program related to the software 3420. Examples of storage device 3428 include, e.g., hard disk drive (HDD); optical drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 3428 may be non-volatile, mutable, or read-only. Some storage device 3428 may be internal and connect to the computing device 3400 via a bus 3450. Some storage device 3428 may be external and connect to the computing device 3400 via an I/O device 3430 that provides an external bus. Some storage device 3428 may connect to the computing device 3400 via the network interface 3418 over a network 3404. Some client devices 3400 may not require a non-volatile storage device 3428 and may be thin clients or zero clients 3402. Some storage device 3428 may also be used as an installation device 3416, and may be suitable for installing software and programs.

Client device 3400 may also install software or application from an application distribution platform. An application distribution platform may facilitate installation of software on a client device 3402. An application distribution platform may include a repository of applications on a server 3406 or a cloud 3408, which the clients 3402*a*-3402*n* may access over a network 3404. An application distribution platform may include application developed and provided by various developers. A user of a client device 3402 may select, purchase and/or download an application via the application distribution platform.

Furthermore, the computing device 3400 may include a network interface 3418 to interface to the network 3404 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 3400 communicates with other computing devices 3400' via any type and/or form of gateway or tunneling protocol e.g. Secure Socket Layer (SSL) or Transport Layer Security (TLS). The network interface 3418 may comprise a built-in network adapter, network interface card, PCMCIA network card, EXPRESSCARD network card, card bus network adapter, wireless network adapter, USB network adapter, modem or any other device suitable for interfacing the computing device 3400 to any type of network capable of communication and performing the operations described herein.

A computing device 3400 of the sort depicted in FIGS. 34B and 34C may operate under the control of an operating system, which controls scheduling of tasks and access to system resources. The computing device 3400 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 3400 can be any workstation, telephone, desktop computer, laptop or notebook computer, netbook, tablet, server, handheld computer, mobile telephone, smartphone or other portable telecommunications device, media playing device, a gaming system, mobile computing device, or any other type and/or form of computing, telecommunications or media device that is capable of communication. The computer system 3400 has sufficient processor power and memory capacity to perform the operations described herein. In some embodiments, the computing device 3400 may have different processors, operating systems, and input devices consistent with the device.

In some embodiments, the computing device 3400 is a gaming system. In some embodiments, the computing device 3400 is a digital audio player. Some digital audio players may have other functionality, including, e.g., a gaming system or any functionality made available by an application from a digital application distribution platform. In some embodiments, the computing device 3400 is a portable media player or digital audio player supporting file formats including. In some embodiments, the computing device 3400 is a tablet. In other embodiments, the computing device 3400 is an eBook reader. In some embodiments, the communications device 3402 includes a combination of devices, e.g. a smartphone combined with a digital audio player or portable media player. For example, one of these embodiments is a smartphone. In yet another embodiment, the communications device 3402 is a laptop or desktop computer equipped with a web browser and a microphone and speaker system, e.g. a telephony headset. In these embodiments, the communications devices 3402 are web-enabled and can receive and initiate phone calls. In some embodiments, a laptop or desktop computer is also equipped with a webcam or other video capture device that enables video chat and video call. In some embodiments, the communication device 3402 is a wearable mobile computing device.

In some embodiments, the status of one or more machines 3402, 3406 in the network 3404 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

The description herein including modules emphasizes the structural independence of the aspects of the image classifier, and illustrates one grouping of operations and responsibilities of the image classifier. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method of training models for classifying images, comprising:
    identifying, by an image classifier executing on one or more processors, a plurality of tiles from an image, the image associated with a label indicating one of a presence or an absence of a condition within the image;
    applying, by the image classifier, an inference model having a plurality of parameters to the plurality of tiles to determine a tile-specific score for each tile of the plurality of tiles from the image, the tile-specific score indicating a likelihood of one of the presence or the absence of the condition within the tile;
    selecting, by the image classifier, a subset of tiles from the plurality of tiles based on the determined tile-specific score for each tile;
    comparing, by the image classifier, the tile-specific score determined for each tile of the subset of tiles to a threshold value for the image associated with the label indicating one of the presence or the absence of the condition; and
    modifying, by the image classifier, at least one parameter of the inference model based on comparing the tile-specific score of each tile to the threshold value.

2. The method of claim 1, wherein comparing the tile-specific score further comprises determining an error metric for each tile of the subset of tiles between the tile-specific score for the tile and a baseline metric for the presence or the absence of the condition; and
    wherein modifying the at least one parameter further comprises modifying the at least one parameter based on the error metric determined for each tile of the subset of tiles.

3. The method of claim 1, wherein selecting the subset of tiles further comprises selecting a predefined number of tiles from the plurality of tiles, the predefined number of tiles having highest corresponding tile-specific scores among tile-specific scores determined for the plurality of tiles.

4. The method of claim 1, wherein comparing the tile-specific score further comprises comparing the tile-specific score to the threshold value and an inequality operand, the inequality operand including a greater than for the presence of the condition and a less than or equal to for the absence of the condition.

5. The method of claim 1, wherein comparing the tile-specific score further comprises comparing the tile-specific score to the threshold value corresponding to one of a plurality of threshold values, the plurality of threshold values including a first threshold value for the presence of the condition and a second threshold value for the absence of the condition.

6. The method of claim 1, wherein applying the inference model further comprises applying the inference model to the plurality of tiles, the inference model lacking an internal state memory to process the plurality of tiles without any sequential dependence between processing of the tiles.

7. The method of claim 1, further comprising providing, by the image classifier, the subset of tiles selected from the plurality of tiles to apply an aggregation model to determine a classification result for the image, the classification result indicating one of the image having at least one feature corresponding to the presence of the condition or the image lacking any feature corresponding to the absence of the condition.

8. A method of training models for classifying images, comprising:
    identifying, by an image classifier executing on one or more processors, a subset of tiles from a plurality of tiles of an image, the image associated with a label indicating one of a presence or an absence of a condition within the image;
    applying, by the image classifier, an aggregation model having a plurality of parameters to the subset of tiles in a sequence to determine a classification result for the image from which the subset of tiles are identified, the classification result indicating one of the image having at least one feature corresponding to the presence of the condition or the image lacking any feature corresponding to the absence of the condition;
    comparing, by the image classifier, the classification result determined by the aggregation model to the label indicating one of the presence or the absence of the condition;
    modifying, by the image classifier, at least one parameter of the aggregation model based on comparing the classification result to the label.

9. The method of claim 8, wherein identifying the subset of tiles further comprises identifying the subset of tiles from the plurality of tiles, the plurality of tiles including sets of tiles at one of a corresponding plurality of magnification factors.

10. The method of claim 8, wherein applying the aggregation model further comprises applying the aggregation model to the subset of tiles in accordance with the sequence, the sequence specifying an order of feeding the subset of tiles based on a coordinate for each tile in the subset of tiles.

11. The method of claim 8, wherein comparing the classification result further comprises determining an error metric between the classification result and the label indicating one of the presence or the absence of the condition; and wherein modifying the at least one parameter further comprises modifying the at least one parameter based on the error metric determined between the classification and the label.

12. The method of claim 8, wherein identifying the subset of tiles further comprises identifying the subset of tiles selected by an inference model based on a tile-specific score for each tile of the plurality of tiles from the image, the tile-specific score indicating a likelihood of one of the presence or the absence of the condition.

13. The method of claim 8, wherein applying the aggregation model further comprises applying the aggregation model to the subset of tiles, the aggregation model having internal state memory to process the subset of tiles with a sequential dependence between tiles of the subset.

14. A system for training models for classifying images, comprising:

an image classifier executable on one or more processors, configured to:

identify a plurality of tiles from an image, the image associated with a label indicating one of a presence or an absence of a condition within the image;

establish an inference model having a first plurality of parameters to the plurality of tiles to determine a tile-specific score for each tile of the plurality of tiles indicating a likelihood of one of the presence or the absence of the condition and to a subset of tiles from the plurality of tiles based on the determined tile-specific score for each tile; and modify at least one parameter of the inference model based on comparison between the tile-specific score determined for each tile of the subset of tiles to a threshold value for the label indicating one of the presence or the absence of the condition;

establish an aggregation model having a second plurality of parameters to the subset of tiles in a sequence to determine a classification result for the image from which the subset of tiles are identified, the classification result indicating one of the image having at least one feature corresponding to the presence of the condition or the image lacking any feature corresponding to the absence of the condition; and modify at least one parameter of the aggregation model based on a comparison between the classification result determined by the aggregation model to the label indicating one of the presence or the absence of the condition.

15. The system of claim 14, wherein the image classifier is further configured to:

determine an error metric for each tile of the subset of tiles between the tile-specific score for the tile and a baseline metric for the presence or the absence of the condition; and modify the at least one parameter based on the error metric determined for each tile of the subset of tiles.

16. The system of claim 14, wherein the image classifier is further configured to:

determine an error metric between the classification result and the label indicating one of the presence or the absence of the condition; and modify the at least one parameter based on the error metric determined between the classification and the label.

17. The system of claim 14, wherein the image classifier is further configured to:

determine whether the tile-specific score is greater than the threshold value in response to the label indicating the presence of the condition; and determine whether the tile-specific score is less than or equal to the threshold value in response to the label indicating the absence of the condition.

18. The system of claim 14, wherein the image classifier is further configured to identify the plurality of tiles from the image, the plurality of tiles including sets of tiles at one of a corresponding plurality of magnification factors.

19. The system of claim 14, wherein the image classifier is further configured to apply the aggregation model to the subset of tiles in accordance with the sequence, the sequence specifying an order of feeding the subset of tiles based on a coordinate for each tile in the subset of tiles.

20. The system of claim 14, wherein the inference model lacks an internal state memory to process the plurality of tiles without any sequential dependence between processing of the tiles; and wherein the aggregation model has internal state memory to process the subset of tiles with a sequential dependence between tiles of the subset.

* * * * *